united States Patent
Vogels et al.

(10) Patent No.: US 7,250,293 B2
(45) Date of Patent: *Jul. 31, 2007

(54) COMPLEMENTING CELL LINES

(75) Inventors: Ronald Vogels, Linschoten (NL);
Menzo Havenga, Alphen aan den Rijn (NL); Majid Mehtali, Plobsheim (FR)

(73) Assignee: Crucell Holland B.V., Leiden (NL)

(*) Notice: Subject to any disclaimer, the term of this patent is extended or adjusted under 35 U.S.C. 154(b) by 211 days.

This patent is subject to a terminal disclaimer.

(21) Appl. No.: 10/272,041

(22) Filed: Oct. 15, 2002

(65) Prior Publication Data

US 2003/0119192 A1 Jun. 26, 2003

Related U.S. Application Data

(63) Continuation of application No. 09/713,678, filed on Nov. 15, 2000, now Pat. No. 6,492,169, which is a continuation-in-part of application No. 09/573,740, filed on May 18, 2000, now Pat. No. 6,913,922.

(60) Provisional application No. 60/134,764, filed on May 18, 1999.

(51) Int. Cl.
*C12N 5/10* (2006.01)
*C12N 5/08* (2006.01)
*C12N 15/63* (2006.01)
*C12N 15/861* (2006.01)
*C12N 15/87* (2006.01)
*A61K 48/00* (2006.01)

(52) U.S. Cl. ............ 435/325; 435/366; 435/455; 435/463; 435/465; 424/93.21

(58) Field of Classification Search ........... 435/456, 435/366, 235.1
See application file for complete search history.

(56) References Cited

U.S. PATENT DOCUMENTS

| | | | |
|---|---|---|---|
| 4,487,829 A | 12/1984 | Sharp et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |
| 4,792,525 A | 12/1988 | Ruoslahti et al. |
| 4,797,368 A | 1/1989 | Carter et al. |
| 4,956,281 A | 9/1990 | Wallner et al. |
| 5,024,939 A | 6/1991 | Gorman |
| 5,096,815 A | 3/1992 | Ladner et al. |
| 5,166,320 A | 11/1992 | Wu et al. |
| 5,198,346 A | 3/1993 | Ladner et al. |
| 5,204,445 A | 4/1993 | Plow et al. |
| 5,223,394 A | 6/1993 | Wallner |
| 5,223,409 A | 6/1993 | Ladner et al. |
| 5,240,846 A | 8/1993 | Collins et al. |
| 5,246,921 A | 9/1993 | Reddy et al. |
| 5,332,567 A | 7/1994 | Goldenberg |
| 5,349,053 A | 9/1994 | Landolfi |
| 5,403,484 A | 4/1995 | Ladner et al. |
| 5,436,146 A | 7/1995 | Shenk et al. |
| 5,443,953 A | 8/1995 | Hansen et al. |
| 5,474,935 A | 12/1995 | Chatterjee et al. |
| 5,521,291 A | 5/1996 | Curiel et al. |
| 5,534,423 A | 7/1996 | Plasson et al. |
| 5,543,328 A | 8/1996 | McClelland et al. |
| 5,547,932 A | 8/1996 | Curiel et al. |
| 5,552,311 A | 9/1996 | Sorscher et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,712,136 A | 1/1998 | Wickham et al. |
| 5,731,190 A | 3/1998 | Wickham et al. |
| 5,756,086 A | 5/1998 | McClelland et al. |
| 5,770,442 A | 6/1998 | Wickham et al. |

(Continued)

FOREIGN PATENT DOCUMENTS

| | | |
|---|---|---|
| EP | 259212 | 8/1987 |
| EP | 1016726 | 12/1998 |
| EP | 99201545.3 | 5/1999 |
| EP | 1067188 | 7/1999 |
| EP | 1020529 | 11/1999 |

(Continued)

OTHER PUBLICATIONS

Imler, J-L et al. "Novel complementation cell lines derived from human lung carcinoma A549 cells suport the growth of E1-deleted adenovirus vectors", Gene Therapy, vol. 3: p. 75-84, 1996.*
Babiss, L.E. et al., "Expression of Adenovirus E1a and E1b Gene Products and the *Escherichia coli* XGPRT Gene in KB Cells", 1983, J. Virol., vol. 46: pp. 454-465.*
Anderson, Nature, "Human gene therapy," Apr. 1998, vol. 392, pp. 25-30.

(Continued)

*Primary Examiner*—Scott D. Priebe
*Assistant Examiner*—Michael Burkhart
(74) *Attorney, Agent, or Firm*—TraskBritt

(57) ABSTRACT

A packaging cell line capable of complementing recombinant adenoviruses based on serotypes from subgroup B, preferably adenovirus type 35. The cell line is preferably derived from primary diploid human cells transformed by adenovirus E1 sequences either operatively linked on one or two DNA molecules, the sequences operatively linked to regulatory sequences enabling transcription and translation of encoded proteins. Also, a cell line derived from PER.C6 that expresses functional Ad35-E1B sequences. The Ad35-E1B sequences are driven by the E1B promoter and terminated by a heterologous poly-adenylation signal. The new cell lines are useful for producing recombinant adenoviruses. The cell lines can be used to produce human recombinant therapeutic proteins such as human antibodies. In addition, the cell lines are useful for producing human viruses other than adenovirus such as influenza, herpes simplex, rotavirus, and measles.

17 Claims, 27 Drawing Sheets

U.S. PATENT DOCUMENTS

| | | | |
|---|---|---|---|
| 5,837,511 A | 11/1998 | Flack-Pedersen et al. | |
| 5,846,782 A | 12/1998 | Wickham et al. | |
| 5,849,561 A | 12/1998 | Falck-Pedersen | |
| 5,856,152 A | 1/1999 | Wilson et al. | |
| 5,871,727 A | 2/1999 | Curiel | |
| 5,871,982 A | 2/1999 | Wilson et al. | |
| 5,877,011 A | 3/1999 | Armentano et al. | |
| 5,922,315 A | 7/1999 | Roy | |
| 5,994,128 A | 11/1999 | Fallaux et al. | |
| 6,033,908 A | 3/2000 | Bout et al. | |
| 6,057,155 A | 5/2000 | Wickham et al. | |
| 6,100,086 A | 8/2000 | Kaplan et al. | |
| 6,127,525 A | 10/2000 | Crystal et al. | |
| 6,287,857 B1 | 9/2001 | O'riordan et al. | |
| 6,306,652 B1 | 10/2001 | Fallaux et al. | |
| 6,486,133 B1 | 11/2002 | Herlyn et al. | |
| 6,492,169 B1 * | 12/2002 | Vogels et al. | 435/325 |
| 6,669,942 B2 | 12/2003 | Perricaudet et al. | |
| 6,869,794 B2 * | 3/2005 | Vogels et al. | 435/325 |
| 6,913,922 B1 * | 7/2005 | Bout et al. | 435/320.1 |
| 2005/0084480 A1 * | 4/2005 | Bout et al. | 424/93.2 |

FOREIGN PATENT DOCUMENTS

| | | |
|---|---|---|
| EP | 0 978 566 A2 | 2/2000 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/15644 | 7/1994 |
| WO | WO 94/17832 | 8/1994 |
| WO | WO 94/24299 | 10/1994 |
| WO | WO 94/26915 | 11/1994 |
| WO | WO 95/05201 | 2/1995 |
| WO | WO 95/06745 | 3/1995 |
| WO | WO 95/14785 | 6/1995 |
| WO | WO 95/16037 | 6/1995 |
| WO | WO 95/21259 | 8/1995 |
| WO | WO 95/26412 | 10/1995 |
| WO | WO 95/27071 | 10/1995 |
| WO | WO 95/31187 | 11/1995 |
| WO | WO 95/31566 | 11/1995 |
| WO | WO 96/00326 | 1/1996 |
| WO | WO 96/00790 | 1/1996 |
| WO | WO 96/07739 | 3/1996 |
| WO | WO 96/10087 | 4/1996 |
| WO | WO 96/12030 | 4/1996 |
| WO | WO 96/13597 | 5/1996 |
| WO | WO 96/13598 | 5/1996 |
| WO | WO 96/14837 | 5/1996 |
| WO | WO 96/17073 | 6/1996 |
| WO | WO 96/ 18740 | 6/1996 |
| WO | WO 96/24453 | 8/1996 |
| WO | WO 96/26281 | 8/1996 |
| WO | WO 96/35798 | 11/1996 |
| WO | WO 97/00326 | 1/1997 |
| WO | WO 97/12986 | 4/1997 |
| WO | WO 97/20575 | 6/1997 |
| WO | WO 97/38723 | 10/1997 |
| WO | WO 98/07865 | 2/1998 |
| WO | WO 98/11221 | 3/1998 |
| WO | WO 98/13499 | 4/1998 |
| WO | WO 98/22609 | 5/1998 |
| WO | WO 98/ 32842 | 7/1998 |
| WO | WO 98/40509 | 9/1998 |
| WO | WO 98/49300 | 11/1998 |
| WO | WO 98/50053 A1 | 11/1998 |
| WO | WO 99/32647 | 7/1999 |
| WO | WO 99/47180 A1 | 9/1999 |
| WO | WO 99/55132 | 11/1999 |
| WO | WO 99/58646 | 11/1999 |
| WO | WO 00/03029 | 1/2000 |
| WO | WO 00/24730 A2 | 5/2000 |
| WO | WO 00/31285 | 6/2000 |
| WO | WO 00/52186 | 9/2000 |
| WO | WO 00/70071 A1 | 11/2000 |
| WO | WO 01/04334 | 1/2001 |
| WO | WO 01/90158 A1 | 11/2001 |
| WO | WO 02/24730 | 3/2002 |
| WO | WO 02/27006 | 4/2002 |

OTHER PUBLICATIONS

Basler et al., Sequence of the immunoregulatory early region 3 and flanking sequences of adenovirus type 35, 1996, Gene 170, pp. 249-254.

Chiu et al., Folding & Design, "Optimizing energy potentials for success in protein tertiary structure prediction," May 1998, vol. 3, pp. 223-228.

Gurunathan et al., American Association of Immunologists, "CD40 Ligand Trimer DNA Enhances Both Humoral and Cellular Immune Responses and Induces Protective Immunity to Infectious and Tumor Challenge," 1998, vol. 161, pp. 4563-4571.

Jolly, Viral vector systems for gene therapy, 1994, Cancer Gene Therapy, vol. 1, No. 1, pp. 51-64.

Merriam-Webster Dictionary (on line) retrieved from the internet URL:http://www.m-w.com.cgi-bin.dictionary, "derive," 2002.

Ngo et al., The Protein Folding Problem and Tertiary Structure Prediction, "Computational Complexity, Protein Structure Prediction, and the Levinthal Paradox," 1994, Merz et al. (editors), Birkhauser, Boston, MA, pp. 433 and 492-495.

Stevenson et al., Selective Targeting of Human Cells by a Chimeric Adenovirus Vector Containing a Modified Fiber Protein, 1997, Journal of Virology, vol. 71, pp. 4782-4790.

Verma et al., Nature, "Gene therapy-promises, problems and prospects," Sep. 1997, vol. 389, pp. 239-242.

Abrahamsen et al., Construction of an Adenovirus Type 7a E1A-Vector, Journal of Virology, 1997, pp. 8946-8951, vol. 71, No. 11.

Caillet-Boudin et al., "Functional and Structural Effects of an Ala to Val Mutation in the Adenovirus Serotype 2 Fibre," J. Mol. Biol., 217, 477-486 (1991).

Chroboczek et al., "The Sequence of the Genome of Adenovirus Type 5 and Its Comparison with the Genome of Adenovirus Type 2," Virology, 186, 280-285 (1992).

Chroboczek et al., Adenovirus Fiber, Current Topics in Microbiology and Immunology 1995;199 (Pt 1) pp. 163-200.

Chu et al., "Cell targeting with retroviral vector particles containing antibodyBenvelope fusion proteins," Gene Therapy, 1, 292-299 (1994).

Cotten et al., "TransferrinBpolycation-mediated introduction of DNA into human leukemic cells: Stimulation by agents that affect the survival of transfected DNA or modulate transferrin receptor levels," Proc. Natl. Acad. Sci. USA, 87, 4033-4037 (1990).

Cotten et al., "High-efficiency receptor-mediated delivery of small and large (48 kilobase gene constructs using the endosome-disruption activity of defective or chemically inactivated adenovirus particles," Proc. Natl. Acad. Sci. USA, 89, 6094-6098 (1992).

Crawford-Miksza et al., "Adenovirus Serotype Evolution Is Driven by Illegitimate Recombination in the Hypervariable Regions of the Hexon Protein," Virology, 224, 357-367 (1996).

Crawford-Miksza et al., "Analysis of 15 Adenovirus Hexon Proteins Reveals the Location and Structure of Seven Hypervariable Regions Containing Serotype-Specific Residues," Journal of Virology, Mar. 1996, p. 1836-1844.

Crompton et al., "Expression of a foreign epitope on the surface of the adenovirus hexon," J. Gen. Virol., 75(1), 133-139 (1994).

Crystal, Ronald G., "Transfer of Genes to Humans: Early Lessons and Obstacles to Success," Science, 270, 404-410 (1995).
Curiel et al., "High-Efficiency Gene Transfer Mediated by Adenovirus Coupled to DNABPolylysine Complexes," Human Gene Therapy, 3, 147-154 (1992).
Curiel et al., "Adenovirus enhancement of transferrinBpolylysine-mediated gene delivery," Proc. Natl. Acad. Sci. USA, 88, 8850-8854 (1991).
De Jong et al., "Adenovirus Isolates From Urine of Patients with Acquired Immunodeficiency Syndrome," The Lancet, Jun. 11, 1983 pp. 1293-1296.
De Jong et al., Adenoviruses from Human Immunodeficiency Virus-Infected Individuals, Including Two Strains That Represent New Candidate Serotypes Ad50 and Ad51 of Species B1 and D, Respectively, Journal of Clinical Microbiology, Dec. 1999, p. 3940-3945, vol. 37, No. 12, American Society for Microbiology.
Defer et al., "Human Adenovirus-Host Cell Interactions: Comparative Study with Members of Subgroups B and C," Journal of Virology, 64(8), 3661-3673 (1990).
Deonarain, "Ligand-targeted receptor-mediated vectors for gene delivery," (1998) Expert Opin. Ther. Pat. 8: 53-69.
Dijkema et al., "Transformation of Primary Rat Kidney Cells by DNA Fragments of Weakly Oncogenic Adenoviruses," Journal of Virology, Dec. 1979, p. 943-950.
Douglas J T et al.: "Strategies to accomplish targeted gene delivery to muscle cells employing tropism-modified adenoviral vectors" Neuromusclar Disorders, Pergamon Press, GB, vol. 7, Jul. 1997, pp. 284-298, XP002079944 ISSN: 0960-8966.
Dupuit et al., "Regenerating Cells in Human Airway Surface Epithelium Represent Preferential Targets for Recombinant Adenovirus," Human Gene Therapy, 6, 1185-1193 (1995).
Eck et al., "Gene-Based Therapy," (1996) Goodman & Gillman's The Pharmacological Basis of Therapeutics, Mc-Graw-Hill, New York, N.Y., pp. 77-101.
Etienne-Julan et al., "The efficiency of cell targeting by recombinant retroviruses depends on the nature of the receptor and the composition of the artificial cellBvirus linker," Journal of General Virology, 73, 3251-3255 (1992).
Falgout et al., "Characterization of Adenovirus Particles Made by Deletion Mutants Lacking the Fiber Gene," Journal of Virology, 62(2), 622-625 (1988).
Henry et al., "Characterization of the Knob Domain of the Adenovirus Type 5 Fiber Protein Expressed in *Escherichia coli*," Journal of Virology, 68(8), 5239-5246 (1994).
Hidaka, Chisa, et al., "CAR-dependent and CAR-independent pathways of adenovirus vector-mediated gene transfer and expression in human fibroblasts," 103(4) The Journal of Clinical Investigation 579-87 (Feb. 1999).
Hierholzer et al., "Adenoviruses from Patients with AIDS: A Plethora of Serotypes and A Description of Five New Serotypes of Subgenus D (Types 43-47)," The Journal Of Infectious Diseases vol. 158, No. 4 Oct. 1988.
Hong et al., "The Amino Terminus of the Adenovirus Fiber Protein Encodes the Nuclear Localization Signal," Virology, 185(2), 758-767 (1991).
Horvath et al., "Nonpermissivity of Human Peripheral Blood Lymphocytes to Adenovirus Type 2 Infection," Journal of Virology, 62(1), 341-345 (1988).
Huang et al., "Upregulation of Integrins γ3 and γ5 on Human Monocytes and T Lymphocytes Facilitates Adenovirus-Mediated Gene Delivery," Journal of Virology, 69(4), 2257-2263 (1995).
Imler et al., "Novel complementation cell lines derived from human lung carcinoma A549 cells support the growth of E1-deleted adenovirus vectors," Gene Therapy, vol. 3: p. 75-84, 1996.
Kang et al., "Molecular Cloning And Physical Mapping Of The Dna Of Human Adenovirus Type 35," Acta Microbiologica Hungarica 36 (1), pp. 67-75 (1989).
Kang et al., "Relationship Of E1 And E3 Regions Of Human Adenovirus 35 To Those Of Human Adenovirus Subgroups A, C And D," Acta Microbiologica Hungarica 36 (4), pp. 445-457 (1989).

Karayan et al., "Oligomerization of Recombinant Penton Base of Adenovirus Type 2 and Its Assembly with Fiber in Baculovirus-Infected Cells," Virology, 202, 782-795 (1994).
Kass-Eisler et al., "Quantitative determination of adenovirus-mediated gene delivery to rat cardiac myocytes in vitro and in vivo," Proc. Natl. Acad. Sci. USA, 90, 11498-11502 (1993).
Maunter et al., "Recombinant in Adenovirus: Analysis of Crossover Sites in Intertypic Overlap Recombinants," Virology, 139, 43-52, (1984).
Michael et al., "Addition of a short peptide ligand to the adenovirus fiber protein," Gene Therapy, 2, 660-668 (1995).
Michael et al., "Binding-incompetent Adenovirus Facilitates Molecular Conjugate-mediated Gene Transfer by the Receptor-mediated Endocytosis Pathway," Journal of Biological Chemistry, 268(10),6866-6869 (1993).
Miller et al., "Targeted vectors for gene therapy," FASEB Journal, 9, 190-199 (1995).
Neda et al., "Chemical Modification of an Ecotropic Murine Leukemia Virus Results in Redirection of Its Target Cell Specificity," Journal of Biological Chemistry, 266(22), 14143-14146 (1991).
Nemerow et al., "The Role of v Integrins Adenovirus Infection," Biology of Vitronectins and their Receptors, 177-184 (1993).
Nemerow et al., "Adenovirus entry into host cells: a role for $_v$ integrins," Trends In Cell Biology, 4, 52-55 (1994).
Novelli et al., "Deletion Analysis of Functional Domains in Baculovirus-Expressed Adenovirus Type 2 Fiber," Virology, 185, 365-376 (1991).
Orkin et al., "Report and Recommendations of the Panel to Assess the NIH Investment in Research on Gene Therapy," (1995), file:///F/NIHrec.htm ¼/01 1:37 pm.
Peteranderl et al., "Trimerization of the Heat Shock Transcription Factor by a Triple-Stranded -Helical Coiled-Coil," Biochemistry, 31, 12272-12276 (1992).
Prince, "Gene Transfer: A Review Of Methods And Applications," Pathology (1998), 30, pp. 335-347.
Watson et al., "An Antigenic Analysis of the Adenovirus Type 2 Fibre Polypeptide," Journal of Virology, 69, 525-535 (1988).
Wickham et al., "Integrins $_{v3}$ and $_{v5}$ Promote Adenovirus Internalization but Not Virus Attachment," Cell, 73, 309-319 (1993).
Wickham et al., "Integrin γ5 Selectively Promotes Adenovirus Mediated Cell Membrane Permeabilization," Journal of Cell Biology, 127(1), 257-264 (1994).
Wickham et al.: "Increased In Vitro and In Vivo Gene Transfer by Adenovirus Vectors Containing Chimeric Fiber Proteins," Journal of Virology, Nov. 1997, p. 8221-8229.
Zhong et al.: "Recombinant Adenovirus Is An Efficient And Non-Pertubing Genetic Vector For Human Dendritic Cells" European Journal Of Immunology, Weinheim, DE, vol. 29, No. 3, 1999, pp. 964-972, XP000938797 ISSN: 0014-2980.
Flomenberg et al., "Sequence and genetic Organization of Adenovirus Type 35 Early Region 3," Journal of Virology, Nov. 1988, pp. 4431-4437, vol. 62, No. 11.
Gahery-Segard et al., "Immune response to recombinant Capsid Proteins of Adenovirus in Humans: Antifiber and Anti-Penton Base Antibodies Have a Synergistic Effect on Neutralizing Activity," Journal of Virology, Mar. 1998, pp. 2388-2397, vol. 72, No. 3.
Notice of Opposition to a European Patent, Patent No. 1054064, by Cell Genesys Inc., dated Jul. 5, 2005.
Rosenfeld et al., Adenovirus-Mediated Transfer of a recombinant alpha-1-Antitrypsin Gene to the Lung Epithelium in Vivo, Science, Apr. 19, 1991, pp. 431-434, vol. 252.
Roy et al., "Circumvention of Immunity to the Adenovirus major Coat Protein Hexon," Journal of Virology, Aug. 1998, pp. 6875-6879, vol. 72, No. 8.
Stevenson et al., "Human Adenovirus Serotypes 3 and 5 Bind to Two Different Cellular receptors via the Fiber Head Domain," Journal of Virology, May 1995, pp. 2850-2857, vol. 69, No. 5.
Stratford-Perricaudet et al., "Evaluation of the Transfer and Expression in Mice of an Enzyme-Encoding Gene Using a Human Adenovirus Vector," Human Gene Therapy, 1990, pp. 241-256, vol. 1.

Flomenberg et al., "Molecular Epidemiology of Adenovirus Type 35 Infections in Immunocompromised Hosts," The Journal Of Infectious Diseases vol. 155, No. 6, Jun. 1987.

Francki et al., "Classification and Nomenclature of Viruses," Fifth Report of the International Committee on Taxonomy of Viruses; Virology Division of the International Union of Microbiology Societies pp. 140-143, 1991.

Gall et al., "Construction and characterization of Hexon-Chimeric Adenoviruses: Specification of adenovirus serotype," 72(12) Journal of Virology 10260-64 (1998).

Gall et al., "Adenovirus Type 5 and 7 Capsid Chimera: Fiber Replacement Alters Receptor Tropism without Affecting Primary Immune Neutralization Epitopes," Journal Of Virology, Apr. 1996, p. 2116-2123.

George et al., "Gene therapy progress and prospects: adenoviral vectors," Gene Therapy (2003) 10, 1135-1141.

Gorecki, "Prospects and problems of gene therapy: an update," (2001) Expert Opin. Emerging Drugs 6(2): 187-98.

Greber et al., "Stepwise Dismantling of Adenovirus 2 during Entry into Cells," Cell, 75, 477-486 (1993).

Green et al., "Evidence for a repeating cross-sheet structure in the adenovirus fibre," EMBO Journal, 2(8), 1357-1365 (1983).

Grubb et al., Inefficient gene transfer by adenovirus vector to cystic fibrosis airway epithelia of mice and humans, Nature, 371, 802-806 (1994).

Han et al., "Ligand-directed retroviral targeting of human breast cancer cells," Proc. Natl. Acad. Sci. USA, 92, 9747-9751 (1995).

He et al., "A simplified system for generating recombinant adenoviruses," Proc. Natl. Acad. Sci. USA vol. 95, pp. 2509-2514, Mar. 1998.

Kmiec, "Gene Therapy," American Scientist, vol. 87, pp. 240, 1999.

Komoriya et al., The Minimal Essential Sequence for a Major Cell Type-specific Adhesion Site (CS1) within the Alternatively Spliced Type III Connecting Segment Domain of Fibronectin Is Leucine-Aspartic Acid-Valine,: Journal of Biological Chemistry, 266(23), 15075-15079 (1991).

Krasnykh et al.: "Generation Of Recombinant Adenovirus Vectors With Modified Fibers For Altering Viral Tropism" Journal Of Virology, The American Society For Microbiology, US, vol. 70, No. 10, Oct. 1996, pp. 6839-6846, XP002067518 ISSN: 0022-538X.

Lattanzi, Laura, et al., "High Efficiency Myogenic Conversion of Human Fibroblasts by Adenoviral Vector-mediated *MyoD* Gene Transfer," 101(10) J. Clin. Invest. 2119-28 (May 1998).

Lee et al., "The constitutive of the immunomodulatory gp 19k protein in E1, E3 adenoviral vectors strongly reduces the host cytotoxic T cell response against the vector," Gene Therapy (1995) 2, 256-262.

Levrero et al., "Defective and nondefective adenovirus vectors for expressing foreign genes in vitro and in vivo," Gene, 101 (1991) 195-202.

Li et al., "Genetic Relationship between Thirteen Genome Types of Adenovirus 11, 34, and 35 with Different Tropisms," Intervirology 1991;32:338-350.

Liu et al., Molecular Basis of the inflammatory response to adenovirus vectors. Gene Therapy (Oct. 2003, 935-40.

Maraveyas et al., "Targeted Immunotherapy B An update with special emphasis on ovarian cancer," Acta Oncologica, 32(7/8), 741-746 (1993).

Mastrangeli et al., "ASero-Switch@ Adenovirus-Mediated In Vivo Gene Transfer: Circumvention of Anti-Adenovirus Humoral Immune Defenses Against Repeat Adenovirus Vector Administration by Changing the Adenovirus Serotype," Human Gene Therapy, 7, 79-87 (1996).

Mathias et al., "Multiple Adenovirus Serotypes Use v Integrins for Infection," Journal of Virology, 68(10), 6811-6814 (1994).

Maunter et al., "Recombinant in Adenovirus: DNA Sequence Analysis of Crossover Sites in Intertypic Recombinants," Virology, 131, 1-10 (1983).

Pring-Åkerblom et al., "Sequence Characterization and Comparison of Human Adenovirus Subgenus B and E Hexons," Virology, 212, 232-36 (1995).

Ragot et al.,: "Efficient adenovirus-mediated transfer of a human minidystrophin gene to skeletal muscle of mdx mice" Nature, Macmillan Journals Ltd. London, GB, vol. 361, No. 6413, 1993, pp. 647-650, XP002162515 ISSN: 0028-0836.

Rea et al., "Highly efficient transduction of human monocyte-derived dendritic cells with subgroup B fiber-modified adenovirus vectors enhances transgene-encoded antigen presentation to cytotoxic T cells." Journal Of Immunology, (Apr. 15, 2000) 166 (8) 5236-44.,—Apr. 15, 2001 XP002192775.

Robbins et al., "Viral Vectors for Gene Therapy," Pharmacol. Ther. vol. 80, No. 1, pp. 35-47, 1998.

Roberts et al., "Three-Dimensional Structure of the Adenovirus Major Coat Protein Hexon," Science, 232, 1148-51 (1986).

Roelvink et al., The Coxsackievirus-Adenovirus Receptor Protein Can Function as a Cellular Attachment Protein for Adenovirus Serotypes from Subgroups A, C, D, E, and F, Journal Of Virology, Oct. 1998, p. 7909-7915, vol. 72, No. 10.

Romano, "Gene Transfer in Experimental Medicine," Drug & News Perspectives, vol. 16, No. 5, 2003, 13 pages.

Russell et al., "Retroviral vectors displaying functional antibody fragments," Nucleic Acids Research, 21(5), 1081-1085 (1993).

Russell, "Replicating Vectors for Gene Therapy of Cancer: Risks, Limitations and Prospects," European Journal of Cancer, vol. 30A, No. 8, pp. 1165 (1994).

Sabourin et al., "The molecular regulation of myogenesis," (2000) Clin.' Genet. 57(1): 16-25.

Schnurr et al., "Two New Candidate Adenovirus Serotypes," Intervirology 1993;36:79-83.

Schulick et al., "Established Immunity Precludes Adenovirus-mediated Gene Transfer in Rat Cartoid Arteries," The Journal of Clinical Investigation vol. 99, No. 2, Jan. 1997, 209-219.

Segerman et al.: "Adenovirus types 11p and 35p show high binding efficiencies for committed hematopoietic cell lines and are infective to these cell lines" Journal of Virology, The American Society for Microbiology, US, vol. 74, No. 3, Feb. 2000, pp. 1457-1467, XP002161682 ISSN: 0022-538X.

Shayakhmetov et al., "Efficient Gene Transfer into Human CD34[+] Cells by a Retargeted Adenovirus Vector," Journal Of Virology, Mar. 2000, p. 2567-2583.

Signäs et al., "Adenovirus 3 Fiber Polypeptide Gene: Implications for the Structure of the Fiber Protein," Journal of Virology, 53(2), 672-678 (1985).

Silver et al., "Interaction of Human Adenovirus Serotype 2 with Human Lymphoid Cells," Virology, 165, 377-387 (1988).

Stewart et al., "Difference imaging of adenovirus: bringing the resolution gap between X-ray crystallography and electron microscopy," EMBO Journal, 12(7), 2589-2599 (1993).

Stratford-Perricaudet LD et al al.: "Widespread Long-Term Gene Transfer To Mouse Skeletal Muscles And Heart" Journal Of Clinical Investigation, New York, NY, US, vol. 90 No. 2, Aug. 1992, ISSN: 0021-9738.

Toogood et al., "The Adenovirus Type 40 Hexon: Sequence, Predicated Structure and Relationship to Other Adenovirus Hexons," J. gen. Virol (1989), 70, 3203-3214.

Valderrama-Leon et al., "Restriction Endonuclease Mapping of Adenovirus 35, a Type Isolated from Immunocompromised Hosts," Journal Of Virology, Nov. 1985, p. 647-650.

Wadell, "Molecular Epidemiology of Human Adenoviruses," Microbiology and Immunology, vol. 110 pp. 191-220 (1984).

Wagner et al., "Coupling of adenovirus to transferrinBpolylysine/ DNA complexes greatly enhances receptor-mediated gene delivery and expression of transfected genes," Proc. Natl. Acad. Sci. USA, 89, 6099-6103 (1992).

Albiges-Rizo et al., "Human Adenovirus Serotype 3 Fiber Protein," Journal of Biological Chemistry, 266(6), 3961-3967 (1991).

Athappilly et al., "The Refined Crystal Structure of Hexon, the Major Coat Protein of Adenovirus Type 2, at 2•9 A Resolution," J. Mol. Biol. (1994) 242, 430-455.

Bai et al., "Mutations That After an Arg-Gly-Asp (RGD) Sequence in the Adenovirus Type 2 Penton Base Protein Abolish Its Cell-Rounding Activity and Delay Virus Reproduction in Flat Cells," Journal of Virology, 67(9), 5198-5205 (1993).

Bailey et al., "Phylogenetic Relationships among Adenovirus Serotypes," Virology, 205, 439-452 (1994).

Ball-Goodrich et al., "Parvoviral Target Cell Specificity: Acquisition of Fibrotropism by a Mutant of the Lymphotropic Strain of Murine Virus of Mice Involves Multiple Amino Acid Substitutions within the Caspid," Virology, 184, 175-186 (1991).

Basler et al., "Subgroup B Adenovirus Type 35 Early Region 3 mRNAs Differ from Those of the Subgroup C Adenoviruses," Virology 215, 165-177 (1996).

Batra et al., "Receptor-mediated gene delivery employing lectin-binding specificity," Gene Therapy, 1, 255-260 (1994).

Berendsen, Herman J. C., A Glimpse of the Holy Grail, Science, 1998, vol. 282, pp. 642-643.

Boursnell et al., "In vitro construction of a recombinant adenovirus Ad2:Ad5," Gene, 13, 311-317 (1981).

Bridge et al., "Adenovirus Early Region 4 and Viral DNA Synthesis," Virology 193, 794-801 (1993).

Brody et al., "Adenovirus-Mediated in Vivo Gene Transfer," Annals New York Academy of Sciences pp. 90-100 (1994).

\* cited by examiner

% of human sera with neutralising capacity for human adenovirus (n=100)

COMPLEMENTING CELL LINES

CROSS-REFERENCE TO RELATED APPLICATIONS

This application is a continuation of application Ser. No. 09/713,678, filed Nov. 15, 2000, (the contents of the entirety of which are incorporated by this reference), now U.S. Pat. No. 6,492,169, which is a continuation-in-part of application Ser. No. 09/573,740, filed May 18, 2000, now U.S. Pat. No. 6,913,922, which claims benefit, under 35 U.S.C. § 119(e), of the filing date of U.S. Provisional Application Ser. No. 60/134,764, filed May 18, 1999.

TECHNICAL FIELD

The invention relates to the field of biotechnology generally and, more specifically, to adenoviral-based complementing cell lines.

BACKGROUND

Typically, vector and packaging cells are adapted to one another so that they have all the necessary elements, but they do not have overlapping elements which lead to replication-competent virus by recombination. Therefore, the sequences necessary for proper transcription of the packaging construct may be heterologous regulatory sequences derived from, for example, other human adenovirus ("Ad") serotypes, nonhuman adenoviruses, other viruses including, but not limited to, SV40, hepatitis B virus ("HBV"), Rous Sarcoma Virus ("RSV"), cytomegalovirus ("CMV"), etc. or from higher eukaryotes such as mammals. In general, these sequences include a promoter, enhancer and polyadenylation sequences.

PER.C6 (ECACC deposit number 96022940) is an example of a cell line devoid of sequence overlap between the packaging construct and the adenoviral vector (Fallaux et al., 1998). Recombinant viruses based on subgroup C adenoviruses, such as Ad5 and Ad2, can be propagated efficiently on these packaging cells. Generation and propagation of adenoviruses from other serotypes, like subgroup B viruses, has proven to be more difficult on PER.C6 cells. However, as described in European Patent Application 00201738.2, recombinant viruses based on subgroup B virus Ad35 can be made by cotransfection of an expression construct containing the Ad35 early region-1 sequences (Ad35-E1). Furthermore, Ad35-based viruses that are deleted for E1A sequences were shown to replicate efficiently on PER.C6 cells. Thus, the E1A proteins of Ad5 complement Ad35-E1A functions, whereas, at least part of the E1B functions of Ad35 are necessary. This serotype specificity in E1B functions was recently also described for Ad7 recombinant viruses. In an attempt to generate recombinant adenoviruses derived from subgroup B virus Ad7, Abrahamsen et al. (1997) were not able to generate E1-deleted viruses on 293 cells without contamination of wild-type (wt) Ad7. Viruses that were picked after plaque purification on 293-ORF6 cells (Brough et al., 1996) were shown to have incorporated Ad7-E1B sequences by nonhomologous recombination. Thus, efficient propagation of Ad7 recombinant viruses proved possible only in the presence of Ad7-E1B expression and Ad5-E4-ORF6 expression. The E1B proteins are known to interact with cellular, as well as viral, proteins (Bridge et al., 1993; White, 1995). Possibly, the complex formed between the E1B-55K protein and E4-ORF6 which is necessary to increase mRNA export of viral proteins and to inhibit export of most cellular mRNAs, is critical and in some way serotype-specific.

SUMMARY OF THE INVENTION

The present invention provides new packaging cell lines capable of complementing recombinant adenoviruses based on serotypes other than subgroup C viruses, such as serotypes from subgroup B like adenovirus type 35.

The new packaging cells are derived from PER.C6 (ECACC deposit number 96022940; Fallaux et al., 1998) and contain Ad35-E1 sequences integrated into their genome. These Ad35-E1 sequences are present in a functional expression cassette, but preferably do not contain sequences overlapping with sequences present in the recombinant viral vector. Preferably, the functional expression cassette consists of a heterologous promoter and polyadenylation signal functionally linked to Ad35-E1 sequences. More specifically, the Ad35-E1 sequences are functionally linked to the human phosphoglycerate gene promoter (hPGK) and hepatitis B virus poly-adenylation signal (HBV-pA). Preferably, Ad35-E1 sequences comprise the coding regions of the E1A proteins and the E1B promoter sequences linked to E1B coding sequences up to and including the stop codon of the E1B-55K protein. More preferably, the Ad35-E1 sequences comprise nucleotide 468 to nucleotide 3400 of the Ad35 wt sequence. To be able to select for transfected cells, a dominant selection marker like, but not limited to, the neo$^r$ gene has to be incorporated on the expression vector or the Ad35 expression vector is cotransfected with a separate expression vector mediating expression of the selection marker. In both cases, the selection marker becomes integrated in the cellular genome.

The new packaging cells are derived from primary diploid human cells such as, but not limited to, primary human retinoblasts, primary human embryonic kidney cells or primary human amniocytes. Transfection of primary cells with the adenovirus E1A gene alone can induce unlimited proliferation (immortalization), but does not result in complete transformation. However, expression of E1A in most cases results in induction of programmed cell death (apoptosis) and occasionally immortalization is obtained (Jochemsen et al., 1987). Co-expression of the E1B gene is required to prevent induction of apoptosis and for complete morphological transformation to occur (reviewed in White, 1995). Therefore, in one aspect of the invention, primary human cells are transformed by expression of adenovirus E1 proteins of a subgroup other than subgroup C, preferably subgroup B, more preferably adenovirus type 35. The combined activity of the E1A and E1B proteins establishes indefinite growth of the cells and enables complementation of recombinant adenoviruses.

In another aspect of the invention, the transforming E1 sequences are derived from different serotypes. As disclosed in European Patent Application 00201738.2, Ad35-E1 sequences are capable of transforming baby rat kidney ("BRK") cells, albeit with a lower efficiency than that seen with Ad5-E1 sequences. This was also observed for E1 sequences from Ad12 (Bernards et al., 1982). Therefore, in this aspect of the invention, primary diploid human cells are transformed with chimeric E1 constructs that consist of part of the E1 sequences of a serotype that enables efficient transformation of primary human cells and part of the E1 sequences of another serotype, which E1 sequences provide the serotype-specific E1B function(s) that enable(s) efficient propagation of E1-deleted viruses of that serotype. In a preferred embodiment of this aspect of the invention, the E1A region is derived from a subgroup C adenovirus like, but not limited to, Ad5, and the E1B sequences are derived from an alternative adenovirus, more particularly from an adenovirus of subgroup B, even more particularly from adenovirus type 35. In a more preferred embodiment, the E1A sequences and the E1B-21K sequences are derived from a subgroup C adenovirus like, but not limited to, Ad5, and the E1B-55k sequences, as far as not overlapping with the 21K sequences, are derived from an adenovirus of subgroup B, more particularly from adenovirus type 35. In an even more preferred embodiment, all E1 sequences are derived from a subgroup C adenovirus like, but not limited to, Ad5, except for at least the part of the E1B-55K sequences that are necessary for serotype-specific complementation of an alternative adenovirus subgroup, more particularly, adenovirus subgroup B, even more particularly adenovirus type 35, the sequences being derived from the adenovirus.

The primary diploid human cells are transformed by adenovirus E1 sequences, either operatively linked on one DNA molecule or located on two separate DNA molecules. In the latter case, one DNA molecule carries at least part of the E1 sequences of the serotype-enabling efficient transformation and the second DNA molecule carries at least part of the sequences necessary for serotype-specific complementation. In all aspects, the sequences are operatively linked to regulatory sequences enabling transcription and translation of the encoded proteins.

In another aspect of the invention, PER.C6-derived cells are described that express functional Ad35-E1B sequences. In one embodiment, the Ad35-E1B sequences are driven by the E1B promoter and terminated by a heterologous polyadenylation signal like, but not limited to, the HBVpA. In a preferred embodiment, the Ad35-E1B sequences are driven by a heterologous promoter like, but not limited to, the hPGK promoter or Elongation Factor-1α (EF-1α) promoter and terminated by a heterologous pA signal like, but not limited to, the HBVpA. These Ad35-E1B sequences preferably comprise the coding regions of the E1B-21K and the E1B-55K proteins located between nucleotides 1611 and 3400 of the wild-type (wt) Ad35 sequence. More preferably, the Ad35-E1B sequences comprise nucleotides 1550 to 3400 of the wt Ad35 sequence. In an even more preferred embodiment, the E1B sequences comprise the coding sequences of the E1B-55K gene located between nucleotides 1916 and 3400 of the wt Ad35 sequence.

Cell lines the subject of this invention are useful for, among other things, the production of recombinant adenoviruses designed for gene therapy and vaccination. The cell lines, being derived from cells of human origin, are also useful for the production of human recombinant therapeutic proteins like, but not limited to, human growth factors and human antibodies. In addition, the cell lines are useful for the production of human viruses other than adenovirus like, but not limited to, influenza virus, herpes simplex virus, rotavirus, and measles virus.

DETAILED DESCRIPTION OF THE INVENTION

Figure 1:
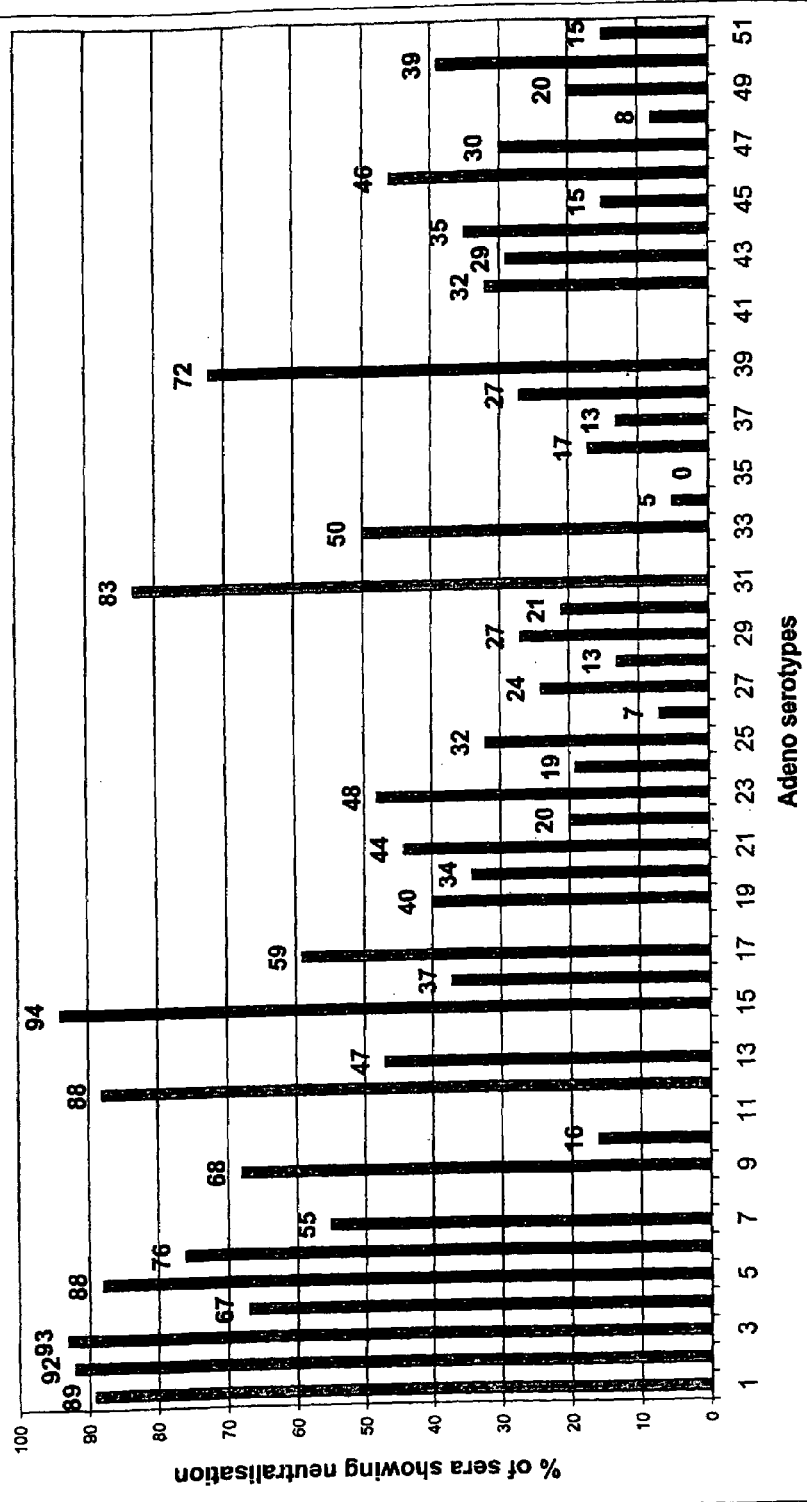
FIG. 1: Bar graph showing the percentage of serum samples positive for neutralization for each human wt adenovirus tested (see, Example 1 for description of the neutralization assay).

The invention is further explained by the use of the following illustrative examples.

EXAMPLES

Example 1

To enable screening of a large amount of human sera for the presence of neutralizing antibodies against all adenovirus serotypes, an automated 96-well assay was developed.

Human Sera

A panel of 100 individuals was selected. Volunteers (50% male, 50% female) were healthy individuals between ages 20 and 60 years old with no restriction for race. All volunteers signed an informed consent form. People professionally involved in adenovirus research were excluded.

Approximately 60 ml blood was drawn in dry tubes. Within two hours after sampling, the blood was centrifuged at 2500 rpm for 10 minutes. Approximately 30 ml serum was transferred to polypropylene tubes and stored frozen at −20° C. until further use.

Serum was thawed and heat-inactivated at 56° for 10 minutes and then aliquoted to prevent repeated cycles of freeze/thawing. Part was used to make five steps of twofold dilutions in medium (DMEM, Gibco BRL) in a quantity large enough to fill out approximately 70 96-well plates. Aliquots of undiluted and diluted sera were pipetted in deep well plates (96-well format) and using a programmed platemate dispensed in 100 µl aliquots into 96-well plates. The plates were loaded with eight different sera in duplo (100 µl/well) according to the scheme below:

| | | | | | | | | | | | |
|---|---|---|---|---|---|---|---|---|---|---|---|
| S1/2 | S1/4 | S1/8 | S1/16 | S1/32 | S5/2 | S5/4 | S5/8 | S5/16 | S5/32 | — | — |
| S1/2 | S1/4 | S1/8 | S1/16 | S1/32 | S5/2 | S5/4 | S5/8 | S5/16 | S5/32 | — | — |
| S2/2 | S2/4 | S2/8 | S2/16 | S2/32 | S6/2 | S6/4 | S6/8 | S6/16 | S6/32 | — | — |
| S2/2 | S2/4 | S2/8 | S2/16 | S2/32 | S6/2 | S6/4 | S6/8 | S6/16 | S6/32 | — | — |
| S3/2 | S3/4 | S3/8 | S3/16 | S3/32 | S7/2 | S7/4 | S7/8 | S7/16 | S7/32 | — | — |
| S3/2 | S3/4 | S3/8 | S3/16 | S3/32 | S7/2 | S7/4 | S7/8 | S7/16 | S7/32 | — | — |
| S4/2 | S4/4 | S3/8 | S3/16 | S3/32 | S8/2 | S8/4 | S8/8 | S8/16 | S8/32 | — | — |
| S4/2 | S4/4 | S3/8 | S3/16 | S3/32 | S8/2 | S8/4 | S8/8 | S8/16 | S8/32 | — | — |

Where S1/2 to S8/2 in columns 1 and 6 represent 1×diluted sera and Sx/4, Sx/8, Sx/16 and Sx/32 the twofold serial dilutions. The last plates also contained four wells filled with 100 µl fetal calf serum as a negative control. Plates were kept at −20° C. until further use.

Preparation of Human Adenovirus Stocks

Prototypes of all known human adenoviruses were inoculated on T25 flasks seeded with PER.C6 cells (Fallaux et al., 1998) and harvested upon full CPE. After freeze/thawing, 1-2 ml of the crude lysates were used to inoculate a T80 flask with PER.C6 and virus was harvested at full CPE. The timeframe between inoculation and occurrence of CPE, as well as the amount of virus needed to re-infect a new culture, differed between serotypes. Adenovirus stocks were prepared by freeze/thawing and used to inoculate 3-4 T175 cm² three-layer flasks with PER.C6 cells. Upon occurrence of CPE, cells were harvested by tapping the flask, pelleted and virus was isolated and purified by a two-step CsCl gradient as follows. Cell pellets were dissolved in 50 ml 10 mM $NaPO_4$ buffer (pH 7.2) and frozen at −20° C. After thawing at 37° C., 5.6 ml sodium deoxycholate (5% w/v) was added. The solution was mixed gently and incubated for 5-15 minutes at 37° C. to completely lyse the cells. After homogenizing the solution, 1875 µl 1M $MgCl_2$ was added. After the addition of 375 µl DNAse (10 mg/ml), the solution was incubated for 30 minutes at 37° C. Cell debris was removed by centrifugation at 1880×g for 30 minutes at RT without brake. The supernatant was subsequently purified from proteins by extraction with FREON (3×). The cleared supernatant was loaded on a 1M Tris/HCl buffered cesium chloride block gradient (range: 1.2/1.4 g/ml) and centrifuged at 21000 rpm for 2.5 hours at 10° C. The virus band is isolated after which a second purification using a 1M Tris/HCl buffered continues gradient of 1.33 g/ml of cesium chloride was performed. The virus was then centrifuged for 17 hours at 55000 rpm at 10° C. The virus band is isolated and sucrose (50% w/v) is added to a final concentration of 1%. Excess cesium chloride is removed by dialysis (three times 1 hr at RT) in dialysis slides (Slide-a-lizer, cut off 10000 kDa, Pierce, USA) against 1.5 liter PBS supplemented with $CaCl_2$ (0.9 mM), $MgCl_2$ (0.5 mM) and an increasing concentration of sucrose (1, 2, 5%). After dialysis, the virus is removed from the slide-a-lizer after which it is aliquoted in portions of 25 and 100 µl upon which the virus is stored at −85° C.

To determine the number of virus particles per milliliter, 50 µl of the virus batch is run on a high-pressure liquid chromatograph (HPLC) as described by Shabram et al (1997). Viruses were eluted using a NaCl gradient ranging from 0 to 600 mM. As depicted in table I, the NaCl concentration by which the viruses were eluted differed significantly among serotypes.

Most human adenoviruses replicated well on PER.C6 cells with a few exceptions. Adenovirus type 8 and 40 were grown on 911-E4 cells (He et al., 1998). Purified stocks contained between $5×10^{10}$ and $5×10^{12}$ virus particles/ml (VP/ml; see Table I).

Titration of Purified Human Adenovirus Stocks

Adenoviruses were titrated on PER.C6 cells to determine the amount of virus necessary to obtain full CPE in five days, the length of the neutralization assay. Hereto, 100 µl medium was dispensed into each well of 96-well plates. 25 µl of adenovirus stocks pre-diluted $10^4$, $10^5$, $10^6$ or $10^7$ times were added to column 2 of a 96-well plate and mixed by pipetting up and down 10 times. Then 25 µl was brought from column 2 to column 3 and again mixed. This was repeated until column 11, after which 25 µl from column 11 was discarded. This way, serial dilutions in steps of 5 were obtained starting off from a pre-diluted stock. Then $3×10^4$ PER.C6 cells (ECACC deposit number 96022940) were added in a 100 µl volume and the plates were incubated at 37° C., 5% $CO_2$ for five or six days. CPE was monitored microscopically. The method of Reed and Muensch was used to calculate the cell culture-inhibiting dose 50% (CCID50).

In parallel, identical plates were set up that were analyzed using the MTT assay (Promega). In this assay, living cells are quantified by colorimetric staining. Hereto, 20 µl MTT (7.5 mgr/ml in PBS) was added to the wells and incubated at 37° C., 5% $CO_2$ for two hours. The supernatant was removed and 100 µl of a 20:1 isopropanol/triton-X100 solution was added to the wells. The plates were put on a 96-well shaker for 3-5 minutes to solubilize the precipitated staining. Absorbance was measured at 540 nm and at 690 nm (background). By this assay, wells with proceeding CPE or full CPE can be distinguished.

Neutralization Assay 96-well plates with diluted human serum samples were thawed at 37° C., 5% $CO_2$. Adenovirus stocks diluted to 200 CCID50 per 50 µl were prepared and 50 µl aliquots were added to columns 1-11 of the plates with serum. Plates were incubated for 1 hour at 37° C., 5% $CO_2$. Then, 50 µl PER.C6 cells at $6×10^5$/ml were dispensed in all wells and incubated for 1 day at 37° C., 5% $CO_2$. Supernatant was removed using fresh pipette tips for each row and 200 µl fresh medium was added to all wells to avoid toxic effects of the serum. Plates were incubated for another 4 days at 37° C., 5% $CO_2$. In addition, parallel control plates were set up in duplo, with diluted positive control sera generated in rabbits and specific for each serotype to be tested in rows A and B and with negative control serum (FCS) in rows C and D. Also, in each of the rows E-H, a titration was performed as described above with steps of five times dilutions starting with 200 CCID50 of each virus to be tested. On day 5, one of the control plates was analyzed microscopically and with the MTT assay. The experimental titer was calculated from the control titration plate observed microscopically. If CPE was found to be complete, i.e., the first dilution in the control titration experiment analyzed by MTT shows clear cell death, all assay plates were processed. If not, the assay was allowed to proceed for one or more days until full CPE was apparent, after which all plates were processed. In most cases, the assay was terminated at day 5. For Ad1, 5, 33, 39, 42 and 43 the assay was left for six days and for Ad2 for eight days.

A serum sample is regarded as "non-neutralizing" when, at the highest serum concentration, a maximum protection of 40% is seen compared to controls without serum.

The results of the analysis of 44 prototype adenoviruses against serum from 100 healthy volunteers are shown in FIG. 1. As expected, the percentage of serum samples that contained neutralizing antibodies to Ad2 and Ad5 was very high. This was also true for most of the lower numbered adenoviruses. Surprisingly, none of the serum samples contained neutralizing antibodies to Ad35. Also, the number of individuals with neutralizing antibody titers to the serotypes 26, 34 and 48 was very low. Therefore, recombinant E1-deleted adenoviruses based on Ad35 or one of the other above-mentioned serotypes have an important advantage compared to recombinant vectors based on Ad5 with respect to clearance of the viruses by neutralizing antibodies.

Also, Ad5-based vectors that have parts of the capsid proteins involved in immunogenic response of the host replaced by the corresponding parts of the capsid proteins of Ad35 or one of the other serotypes will be less, or even not, neutralized by the vast majority of human sera.

Figure 2:
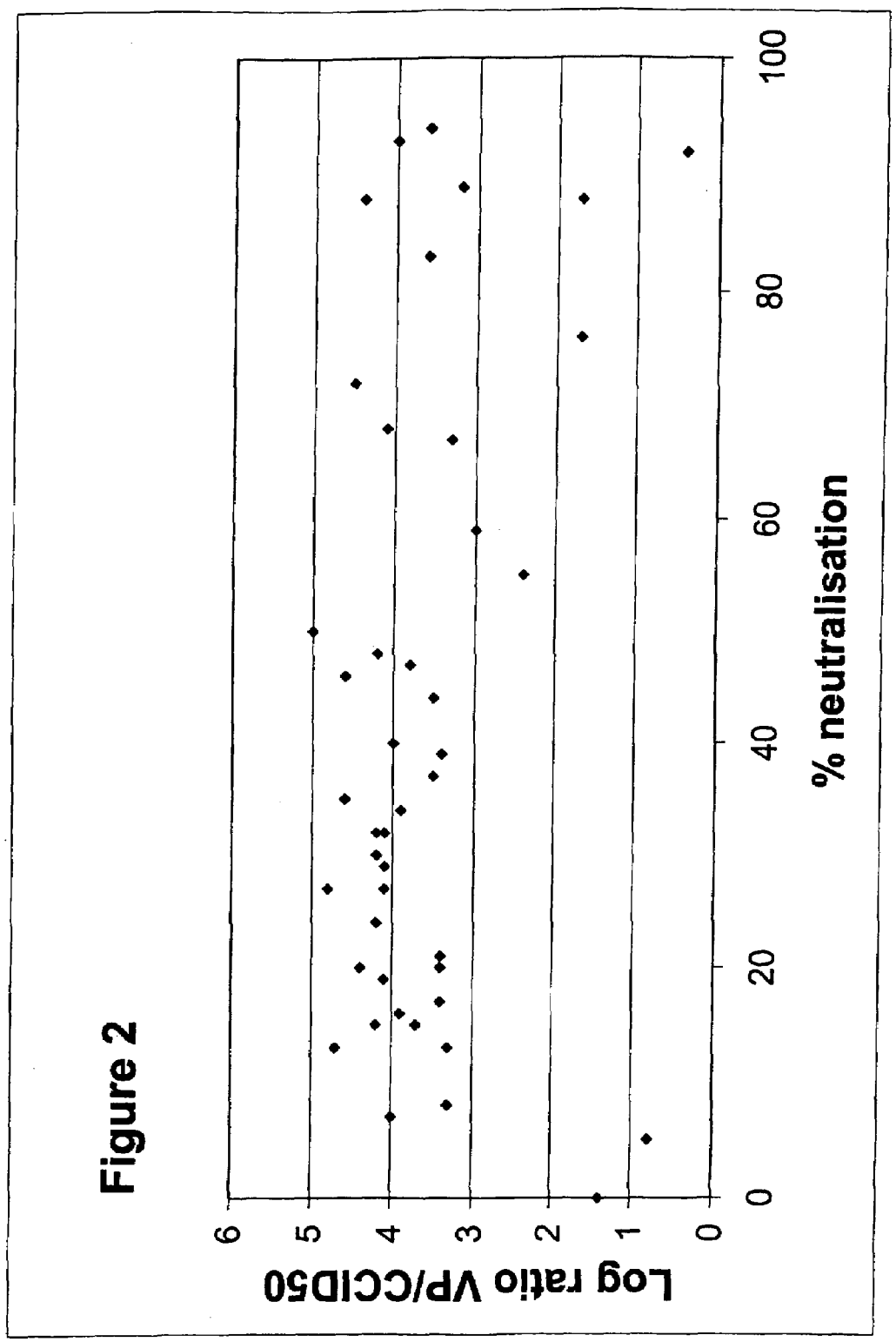
FIG. 2: Graph showing absence of correlation between the VP/CCID50 ratio and the percentage of neutralization.

As can be seen in Table I, the VP/CCID50 ratio calculated from the virus particles per ml and the CCID50 obtained for each virus in the experiments was highly variable and ranged from 0.4 to 5 log. This is probably caused by different infection efficiencies of PER.C6 cells and by differences in replication efficiency of the viruses. Furthermore, differences in batch qualities may play a role. A high VP/CCID50 ratio means that more viruses were put in the wells to obtain CPE in 5 days. As a consequence, the outcome of the neutralization study might be biased since more inactive virus particles could shield the antibodies. To check whether this phenomenon had taken place, the VP/CCID50 ratio was plotted against the percentage of serum samples found positive in the assay (FIG. 2). The graph clearly shows that there is no negative correlation between the amount of viruses in the assay and neutralization in serum.

Example 2

The Prevalence of Neutralizing Activity (NA) to Ad35 is Low in Human Sera from Different Geographic Locations In Example 1, the analysis of neutralizing activity ("NA") in human sera from one location in Belgium was described. Strikingly, of a panel of 44 adenovirus serotypes tested, one serotype, Ad35, was not neutralized in any of the 100 sera assayed. In addition, a few serotypes, Ad26, Ad34 and Ad48 were found to be neutralized in 8%, or less, of the sera tested. This analysis was further extended to other serotypes of adenovirus not previously tested and, using a selection of serotypes from the first screen, was also extended to sera from different geographic locations.

Hereto, adenoviruses were propagated, purified and tested for neutralization in the CPE-inhibition assay as described in Example 1. Using the sera from the same batch as in Example 1, adenovirus serotypes 7B, 11, 14, 18 and 44/1876 were tested for neutralization. These viruses were found to be neutralized in, respectively, 59, 13, 30, 98 and 54% of the sera. Thus, of this series, Ad11 is neutralized with a relatively low frequency.

Figure 3:
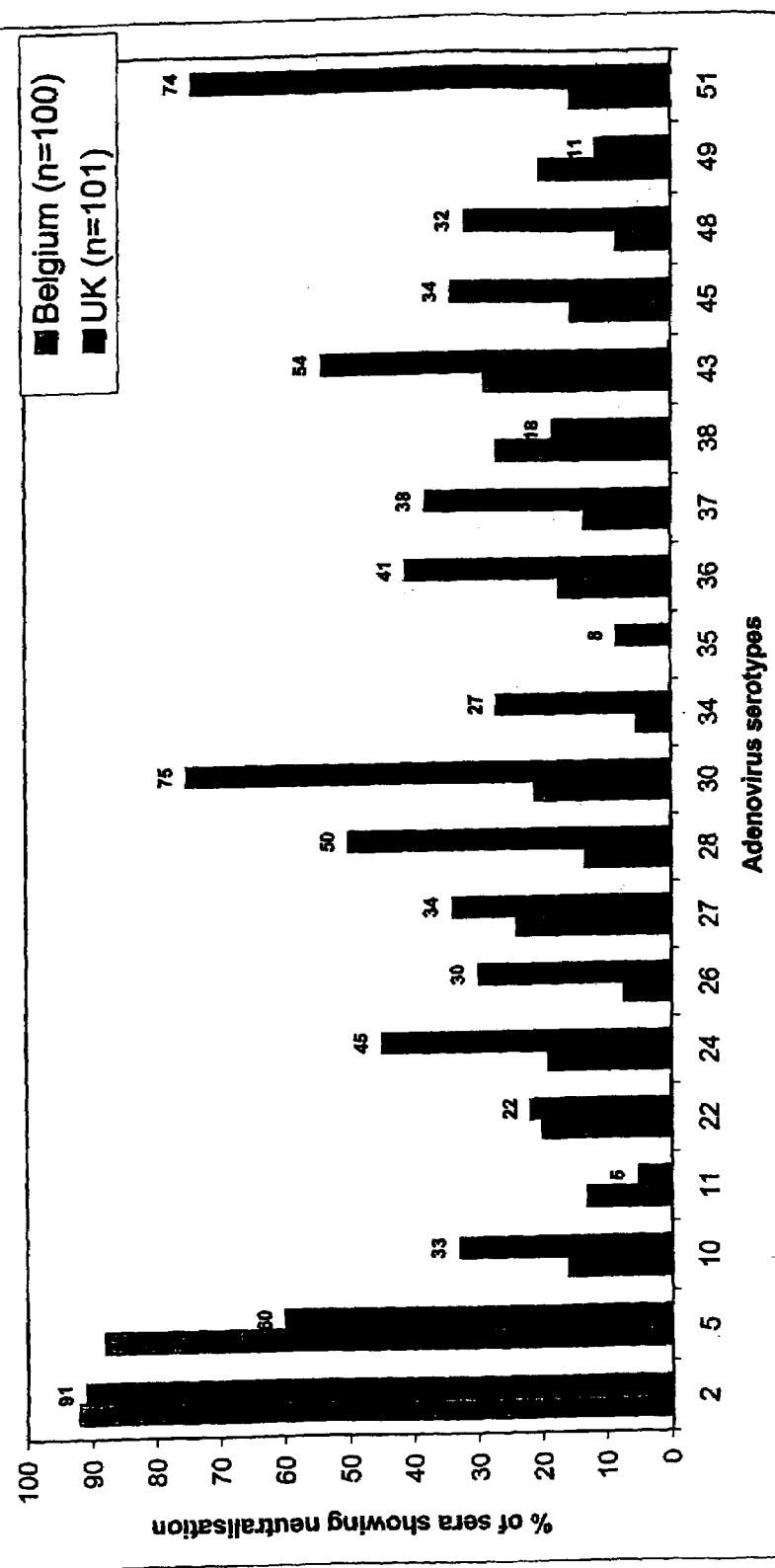
FIG. 3: Bar graph presenting the percentage sera samples that show neutralizing activity to a selection of adenovirus serotypes. Sera were derived from healthy volunteers from Belgium and the UK.

Since it is known that the frequency of isolation of adenovirus serotypes from human tissue, as well as the prevalence of NA to adenovirus serotypes, may differ on different geographic locations, we further tested a selection of the adenovirus serotypes against sera from different places. Human sera were obtained from two additional places in Europe (Bristol, UK and Leiden, NL) and from two places in the United States (Stanford, Calif. and Great Neck, N.Y.). Adenoviruses that were found to be neutralized in 20% or less of the sera in the first screen, as well as Ad2, Ad5, Ad27, Ad30, Ad38, Ad43, were tested for neutralization in sera from the UK. The results of these experiments are presented in FIG. 3. Adenovirus serotypes 2 and 5 were again neutralized in a high percentage of human sera. Furthermore, some of the serotypes that were neutralized in a low percentage of sera in the first screen are neutralized in a higher percentage of sera from the UK, for example, Ad26 (7% vs. 30%), Ad28 (13% vs. 50%), Ad34 (5% vs. 27%) a Ad48 (8% vs. 32%). Neutralizing activity against Ad11 and Ad49 that were found in a relatively low percentage of sera in the first screen, are found in an even lower percentage of sera in this second screen (13% vs. 5% and 20% vs. 11%, respectively). Serotype Ad35 that was not neutralized in any of the sera in the first screen, was now found to be neutralized in a low percentage (8%) of sera from the UK. The prevalence of NA in human sera from the UK is the lowest to serotypes Ad11 and Ad35.

Figure 4:
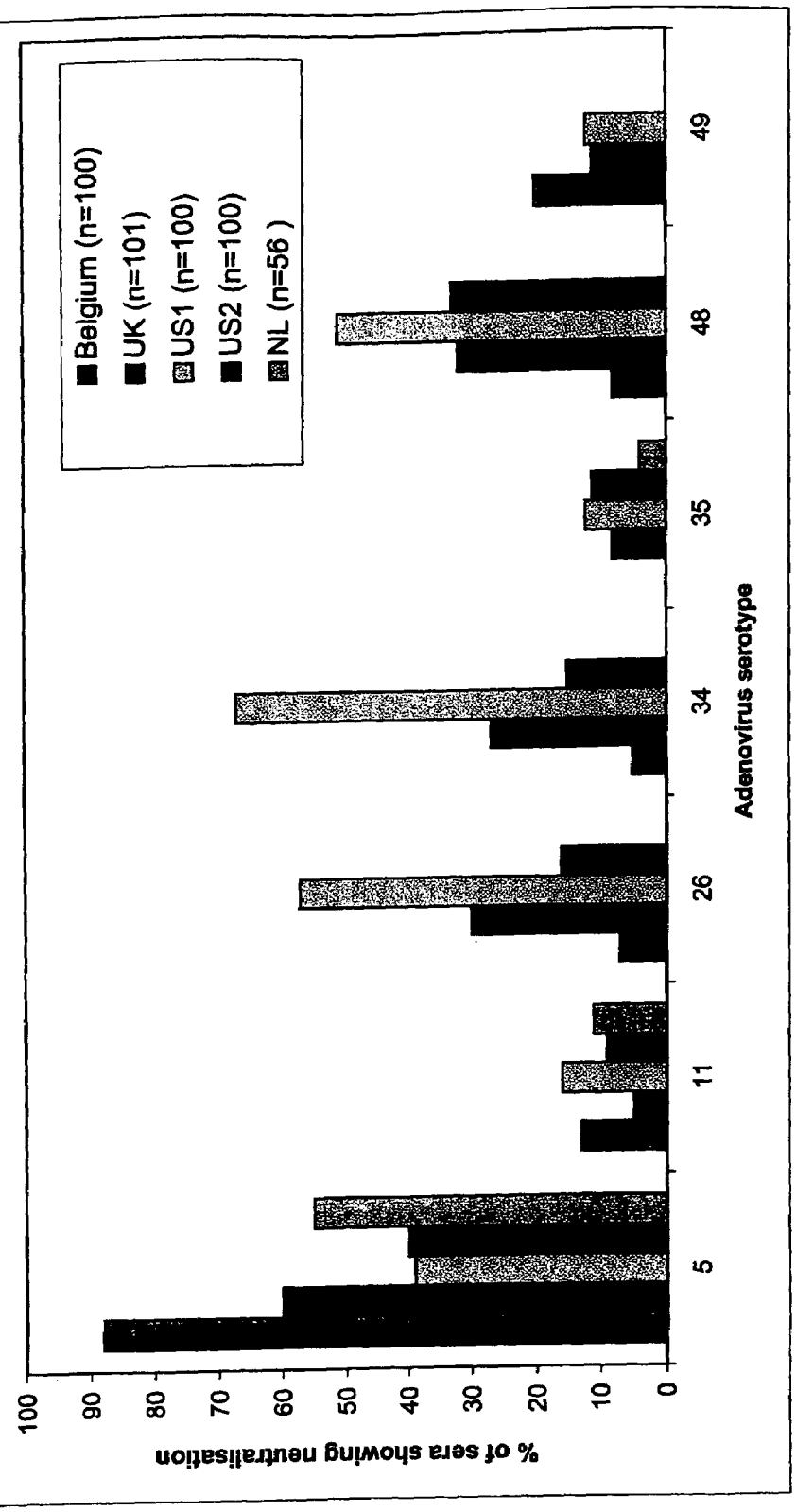
FIG. 4: Bar graph presenting the percentage sera samples that show neutralizing activity to adenovirus serotypes 5, 11, 26, 34, 35, 48 and 49. Sera were derived from five different locations in Europe and the United States.

For further analysis, sera was obtained from two locations in the US (Stanford, Calif. and Great Neck, N.Y.) and from The Netherlands (Leiden). FIG. 4 presents an overview of data obtained with these sera and the previous data. Not all viruses were tested in all sera, except for Ad5, Ad11 and Ad35. The overall conclusion from this comprehensive screen of human sera is that the prevalence of neutralizing activity to Ad35 is the lowest of all serotypes throughout the western countries: on average 7% of the human sera contain neutralizing activity (5 different locations). Another B-group adenovirus, Ad11 is also neutralized in a low percentage of human sera (average 11% in sera from 5 different locations). Adenovirus type 5 is neutralized in 56% of the human sera obtained from 5 different locations. Although not tested in all sera, D-group serotype 49 is also neutralized with relatively low frequency in samples from Europe and from one location of the US (average 14%).

In the herein described neutralization experiments, a serum is judged non-neutralizing when, in the well with the highest serum concentration, the maximum protection of CPE is 40% compared to the controls without serum. The protection is calculated as follows:

$$\% \text{ protection} = \frac{OD \text{ corresponding well} - OD \text{ virus control}}{OD \text{ non-infected control} - OD \text{ virus control}} \times 100\%$$

As described in Example 1, the serum is plated in five different dilutions ranging from 4× to 64×diluted. Therefore, it is possible to distinguish between low titers (i.e., neutralization only in the highest serum concentrations) and high titers of NA (i.e., also neutralization in wells with the lowest serum concentration). Of the human sera used in our screen that were found to contain neutralizing activity to Ad5, 70% turned out to have high titers, whereas, of the sera that contained NA to Ad35, only 15% had high titers. Of the sera that were positive for NA to Ad11, only 8% had high titers. For Ad49, this was 5%. Therefore, not only is the frequency of NA to Ad35, Ad11 and Ad49 much lower as compared to Ad5, but of the sera that do contain NA to these viruses, the vast majority have low titers. Adenoviral vectors based on Ad11, Ad35 or Ad49 have, therefore, a clear advantage over Ad5-based vectors when used as gene therapy vehicles or vaccination vectors in vivo or in any application where infection efficiency is hampered by neutralizing activity.

In the following examples, the construction of a vector system for the generation of safe, RCA-free Ad35-based vectors is described.

Example 3

Sequence of the Human Adenovirus Type 35

Ad35 viruses were propagated on PER.C6 cells and DNA was isolated as follows: To 100 µl of virus stock (Ad35: 3.26×10$^{12}$ VP/ml), 10 µl 10×DNAse buffer (130 mM Tris-HCl pH7.5; 1,2 M CaCl$_2$; 50 mM MgCl$_2$) was added. After addition of 10 µl 10 mgr/ml DNAse I (Roche Diagnostics), the mixture was incubated for 1 hr. at 37° C. Following addition of 2.5 µl 0.5M EDTA, 3.2 µl 20% SDS and 1.5 µl ProteinaseK (Roche Diagnostics; 20 mgr/ml), samples were incubated at 50° C. for 1 hr. Next, the viral DNA was isolated using the GENECLEAN spin kit (Bio101 Inc.) according to the manufacturer's instructions. DNA was eluted from the spin column with 25 µl sterile MilliQ water. The total sequence was generated by Qiagen Sequence Services (Qiagen GmbH, Germany). Total viral DNA was sheared by sonication and the ends of the DNA were made blunt by T4 DNA polymerase. Sheared blunt fragments were size fractionated on agarose gels and gel slices corresponding to DNA fragments of 1.8 to 2.2 kb were obtained. DNA was purified from the gel slices by the QIAquick gel extraction protocol and subcloned into a shotgun library of pUC19 plasmid cloning vectors. An array of clones in 96-well plates covering the target DNA 8 (+/−2) times was used to generate the total sequence. Sequencing was performed on Perkin-Elmer 9700 thermocyclers using Big Dye Terminator chemistry and AmpliTaq FS DNA polymerase followed by purification of sequencing reactions using QIAGEN DyeEx 96 technology. Sequencing reaction products were then subjected to automated separation and detection of fragments on ABI 377 XL 96 lane sequencers. Initial sequence results were used to generate a contiguous sequence and gaps were filled in by primer walking reads on the target DNA or by direct sequencing of PCR products. The ends of the virus turned out to be absent in the shotgun library, most probably due to cloning difficulties resulting from the amino acids of pTP that remain bound to the ITR sequences after proteinase K digestion of the viral DNA. Additional sequence runs on viral DNA solved most of the sequence in those regions, however, it was difficult to obtain a clear sequence of the most terminal nucleotides. At the 5' end the sequence portion obtained was 5'-CCAATAATATACCT-3' (SEQ ID NO:1) while at the 3' end, the obtained sequence portion was 5'-AGGTATATTAT-TGATGATGGG-3' (SEQ ID NO:2). Most human adenoviruses have a terminal sequence 5'-CATCAT-CAATAATATACC-3' (SEQ ID NO:3). In addition, a clone representing the 3' end of the Ad35 DNA obtained after cloning the terminal 7 kb Ad35 EcoRI fragment into pBr322 also turned out to have the typical CATCATCAATAAT . . . sequence. Therefore, Ad35 may have the typical end sequence and the differences obtained in sequencing directly on the viral DNA are due to artifacts correlated with run-off sequence runs and the presence of residual amino acids of pTP.

The total sequence of Ad35 with corrected terminal sequences is given in SEQ ID NO:39. Based sequence homology with Ad5 (Genbank # M72360) and Ad7 (partial sequence Genbank #X03000) and on the location of open reading frames, the organization of the virus is identical to the general organization of most human adenoviruses, especially the subgroup B viruses. The total length of the genome is 34,794 basepairs.

Example 4

Construction of a Plasmid-Based Vector System to Generate Recombinant Ad35-Based Viruses A functional plasmid-based vector system to generate recombinant adenoviral vectors comprises the following components:

1. An adapter plasmid comprising a left ITR and packaging sequences derived from Ad35 and at least one restriction site for insertion of a heterologous expression cassette and lacking E1 sequences. Furthermore, the adapter plasmid contains Ad35 sequences 3' from the E1B coding region including the pIX promoter and coding sequences enough to mediate homologous recombination of the adapter plasmid with a second nucleic acid molecule.
2. A second nucleic acid molecule, comprising sequences homologous to the adapter plasmid, and Ad35 sequences necessary for the replication and packaging of the recombinant virus, that is, early, intermediate and late genes that are not present in the packaging cell.
3. A packaging cell providing at least functional E1 proteins capable of complementing the E1 function of Ad35.

Other methods for generating recombinant adenoviruses on complementing packaging cells are known in the art and may be applied to Ad35 viruses without departing from the invention. As an example, the construction of a plasmid-based system, as outlined above, is described in detail below.

1) Construction of Ad35 Adapter Plasmids

The adapter plasmid pAdApt (described in International Patent Application WO99/55132) was first modified to obtain adapter plasmids that contain extended polylinkers and that have convenient unique restriction sites flanking the left ITR and the adenovirus sequence at the 3' end to enable liberation of the adenovirus insert from plasmid vector sequences. Construction of these plasmids is described below in detail:

Adapter plasmid pAdApt was digested with SalI and treated with Shrimp Alkaline Phosphatase to reduce religation. A linker, composed of the following two phosphorylated and annealed oligos: ExSalPacF 5'-TCG ATG GCA AAC AGC TAT TAT GGG TAT TAT GGG TTC GAA TTA ATT AA-3' (SEQ ID NO:4) and ExSalPacR 5'-TCG ATT AAT TAA TTC GAA CCC ATA ATA CCC ATA ATA GCT GTT TGC CA-3' (SEQ ID NO:5), was directly ligated into the digested construct, thereby replacing the SalI restriction site by Pi-PspI, SwaI and PacI. This construct was designated pADAPT+ExSalPac linker. Furthermore, part of the left ITR of pAdApt was amplified by PCR using the following primers: PCLIPMSF: 5'-CCC CAA TTG GTC GAC CAT CAT CAA TAA TAT ACC TTA TTT TGG-3' (SEQ ID NO:6) and pCLIPBSRGI: 5'-GCG AAA ATT GTC ACT TCC TGT G-3' (SEQ ID NO:7). The amplified fragment was digested with MunI and BsrGI and cloned into pAd5/Clip (described in International Patent Application WO99/55132), which was partially digested with EcoRI and after purification digested with BsrGI, thereby re-inserting the left ITR and packaging signal. After restriction enzyme analysis, the construct was digested with ScaI and SgrAI and an 800 bp fragment was isolated from gel and ligated into ScaI/SgrAI digested pADAPT+ExSalPac linker. The resulting construct, designated pIPspSalAdapt, was digested with SalI, dephosphorylated, and ligated to the phosphorylated ExSalPacF/ExSalPacR double-stranded linker previously mentioned. A clone in which the PacI site was closest to the ITR was identified by restriction analysis and sequences were confirmed by sequence analysis. This novel pAdApt construct, termed pIPspAdapt, thus harbours two ExSalPac linkers containing recognition sequences for PacI, PI-PspI and BstBI, which surround the adenoviral part of the adenoviral adapter construct, and which can be used to linearize the plasmid DNA prior to cotransfection with adenoviral helper fragments.

In order to further increase transgene cloning permutations, a number of polylinker variants were constructed based on pIPspAdapt. For this purpose, pIPspAdapt was first digested with EcoRI and dephosphorylated. A linker composed of the following two phosphorylated and annealed oligos: Ecolinker+: 5'-AAT TCG GCG CGC CGT CGA CGA TAT CGA TAG CGG CCG C-3' (SEQ ID NO:8) and Ecolinker−: 5'-AAT TGC GGC CGC TAT CGA TAT CGT CGA CGG CGC GCC G-3' (SEQ ID NO:9) was ligated into this construct, thereby creating restriction sites for AscI, SalI, EcoRV, ClaI and NotI. Both orientations of this linker were obtained, and sequences were confirmed by restriction analysis and sequence analysis. The plasmid containing the polylinker in the order 5' HindIII, KpnI, AgeI, EcoRI, AscI, SalI, EcoRV, ClaI, NotI, NheI, HpaI, BamHI and XbaI was termed pIPspAdapt1, while the plasmid containing the polylinker in the order HindIII, KpnI, AgeI, NotI, ClaI, EcoRV, SalI, AscI, EcoRI, NheI, HpaI, BamHI and XbaI was termed pIPspAdapt2.

To facilitate the cloning of other sense or antisense constructs, a linker composed of the following two oligonucleotides was designed to reverse the polylinker of pIPspAdapt: HindXba+5'-AGC TCT AGA GGA TCC GTT AAC GCT AGC GAA TTC ACC GGT ACC AAG CTT A-3' (SEQ ID NO:10); HindXba-5'-CTA GTA AGC TTG GTA CCG GTG AAT TCG CTA GCG TTA ACG GAT CCT CTA G-3' (SEQ ID NO:11). This linker was ligated into HindIII/XbaI digested pIPspAdapt and the correct construct was isolated. Confirmation was done by restriction enzyme analysis and sequencing. This new construct, pIPspAdaptA, was digested with EcoRI and the previously mentioned Ecolinker was ligated into this construct. Both orientations of this linker were obtained, resulting in pIPspAdapt3, which contains the polylinker in the order XbaI, BamHI, HpaI, NheI, EcoRI, AscI, SalI, EcoRV, ClaI, NotI, AgeI, KpnI and HindIII. All sequences were confirmed by restriction enzyme analysis and sequencing.

Adapter plasmids based on Ad35 were then constructed as follows: The left ITR and packaging sequence corresponding to Ad35 wt sequences nucleotides 1 to 464 (SEQ ID NO:39) were amplified by PCR on wt Ad35 DNA using the following primers:

```
Primer 35F1:                            (SEQ ID NO:12)
5'-CGG AAT TCT TAA TTA ATC GAC ATC ATC AAT AAT ATA
CCT TAT AG-3'

Primer 35R2:                            (SEQ ID NO:13)
5'-GGT GGT CCT AGG CTG ACA CCT ACG TAA AAA CAG-3'
```

Amplification introduces a PacI site at the 5' end and an AvrII site at the 3' end of the sequence.

For the amplification, Platinum Pfx DNA polymerase enzyme (LTI) was used according to manufacturer's instructions, but with primers at 0.6 μM and with DMSO added to a final concentration of 3%. Amplification program was as follows: 2 min. at 94° C., (30 sec. 94° C., 30 sec. at 56° C., 1 min. at 68° C.) for 30 cycles, followed by 10 min. at 68° C.

The PCR product was purified using a PCR purification kit (LTI) according to the manufacturer's instructions and digested with PacI and AvrII. The digested fragment was then purified from gel using the GENECLEAN kit (Bio 101, Inc.). The Ad5-based adapter plasmid pIPspAdApt-3 was digested with AvrII and then partially with PacI and the 5762 bp fragment was isolated in an LMP agarose gel slice and ligated with the above-mentioned PCR fragment digested with the same enzymes and transformed into electrocompetent DH10B cells (LTI). The resulting clone is designated pIPspAdApt3-Ad35lITR.

In parallel, a second piece of Ad35 DNA was amplified using the following primers:

35F3: 5'-TGG TGG AGA TCT GGT GAG TAT TGG GAA AAC-3' (SEQ ID NO:14)

35R4: 5'-CGG AAT TCT TAA TTA AGG GAA ATG CAA ATC TGT GAG G-3' (SEQ ID NO:15)

Figure 5:
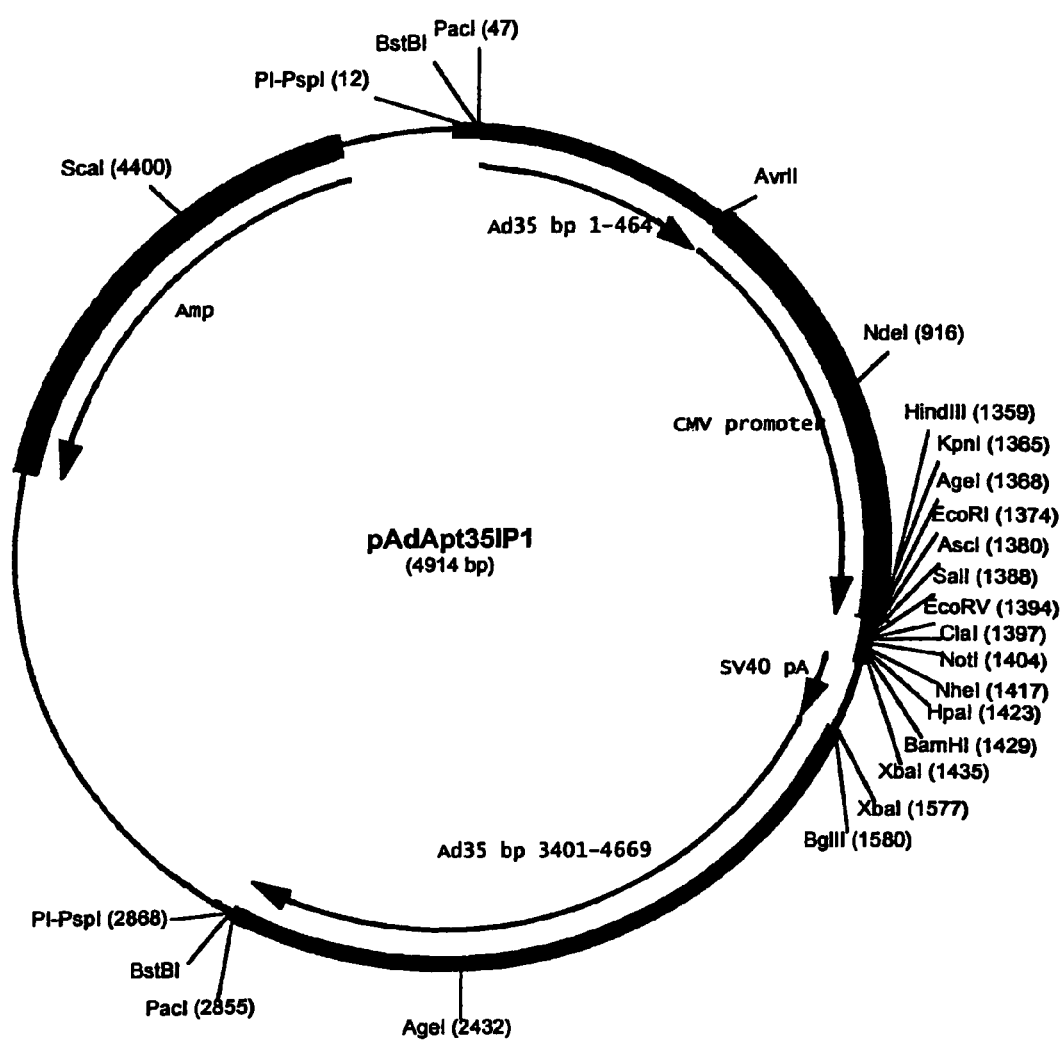
FIG. 5: Map of pAdApt35IP1.

The sequence of this fragment corresponds to nucleotides 3401 to 4669 of wt Ad35 and contains 1.3 kb of sequences starting directly 3' from the E1B-55k coding sequence. Amplification and purification were done as previously described herein for the fragment containing the left ITR and packaging sequence. The PCR fragment was then digested with PacI and subcloned into pNEB193 vector (New England Biolabs) digested with SmaI and PacI. The integrity of the sequence of the resulting clone was checked by sequence analysis. pNEB/Ad35pF3R4 was then digested with BglII and PacI and the Ad35 insert was isolated from gel using the QIAExII kit (Qiagen). pIPspAdApt3-Ad35lITR was digested with BglII and then partially with PacI. The 3624 bp fragment (containing vector sequences, the Ad35 ITR and packaging sequences as well as the CMV promoter, multiple cloning region and polyA signal) was also isolated using the QIAExII kit (Qiagen). Both fragments were ligated and transformed into competent DH10B cells (LTI). The resulting clone, pAdApt35IP3, has the expression cassette from pIPspAdApt3 but contains the Ad35 left ITR and packaging sequences and a second fragment corresponding to nucleotides 3401 to 4669 from Ad35. A second version of the Ad35 adapter plasmid having the multiple cloning site in the opposite orientation was made as follows:

pIPspAdapt1 was digested with NdeI and BglII and the 0.7 kbp band containing part of the CMV promoter, the MCS and SV40 polyA was isolated and inserted in the corresponding sites of pAdApt35IP3 generating pAdApt35IP1 (FIG. 5).

pAdApt35.LacZ and pAdApt35.Luc adapter plasmids were then generated by inserting the transgenes from pcDNA.LacZ (digested with KpnI and BamHI) and pAdApt.Luc (digested with HindIII and BamHI) into the corresponding sites in pAdApt35IP1. The generation of pcDNA.LacZ and pAdApt.Luc is described in International Patent Application WO99/55132.

2) Construction of Cosmid pWE.Ad35.pIX-rITR

Figure 6:
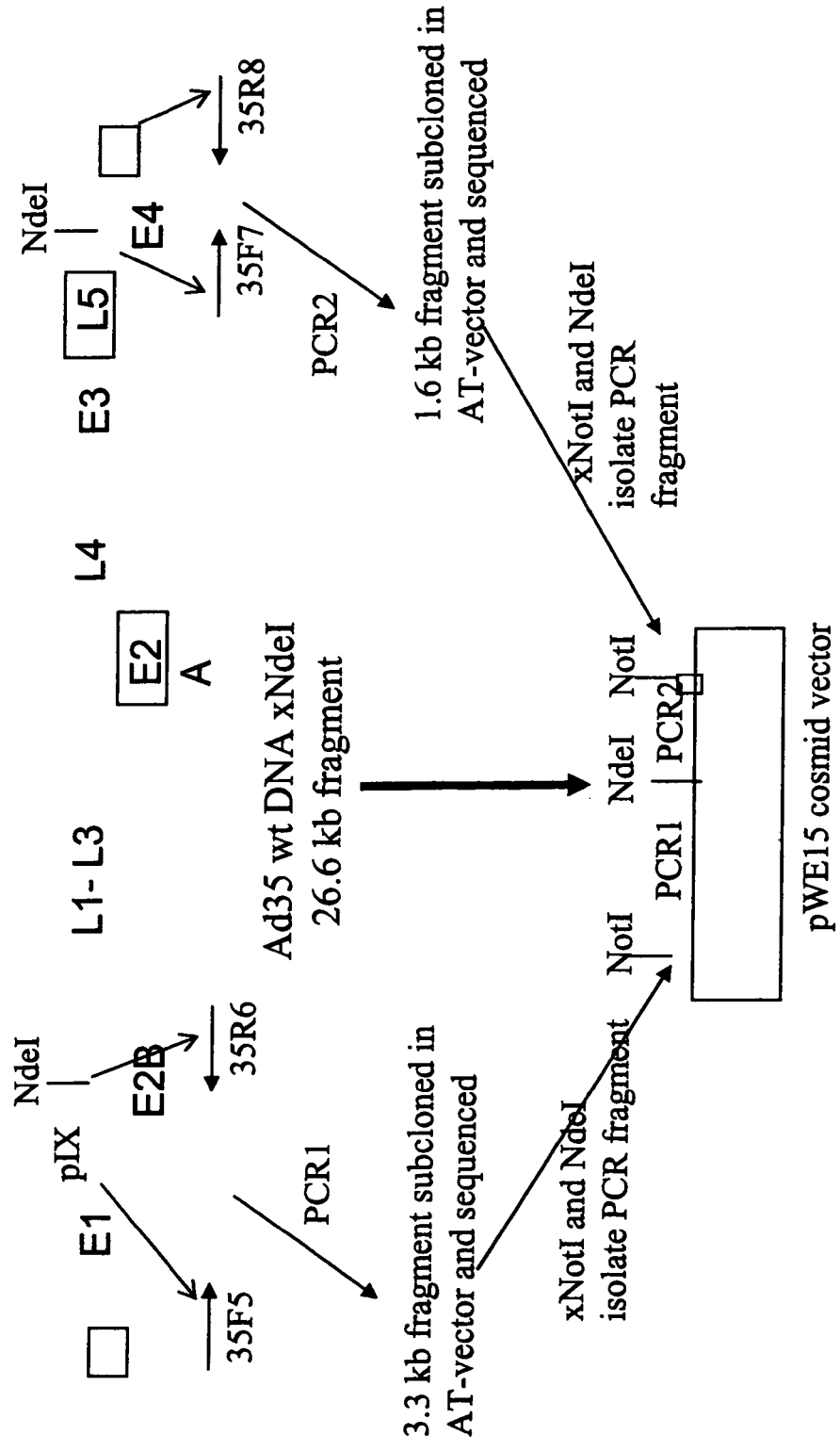
FIG. 6: Schematic representation of the steps undertaken to construct pWE.Ad35.pIX-rITR.

FIG. 6 presents the various steps undertaken to construct the cosmid clone containing Ad35 sequences from bp 3401 to 34794 (end of the right ITR) that are described in detail below.

A first PCR fragment (pIX-NdeI) was generated using the following primer set:

```
35F5:                                               (SEQ ID NO:16)
5'-CGG AAT TCG CGG CCG CGG TGA GTA TTG GGA AAA C-3'

35R6:                                               (SEQ ID NO:17)
5'-CGC CAG ATC GTC TAC AGA ACA G-3'
```

DNA polymerase Pwo (Roche) was used according to manufacturer's instructions, however, with an end concentration of 0.6 µM of both primers and using 50 ngr wt Ad35 DNA as template. Amplification was done as follows: 2 min. at 94° C., 30 cycles of 30 sec. at 94° C., 30 sec. at 65° C. and 1 min. 45 sec. at 72° C., followed by 8 min. at 68° C. To enable cloning in the TA cloning vector PCR2.1, a last incubation with 1 unit superTaq polymerase (HT Biotechnology LTD) for 10 min. at 72° C. was performed.

The 3370 bp amplified fragment contains Ad35 sequences from bp 3401 to 6772 with a NotI site added to the 5' end. Fragments were purified using the PCR purification kit (LTI).

A second PCR fragment (NdeI-rITR) was generated using the following primers:

```
35F7:                                               (SEQ ID NO:18)
5'-GAA TGC TGG CTT CAG TTG TAA TC-3'

35R8:                                               (SEQ ID NO:19)
5'-CGG AAT TCG CGG CCG CAT TTA AAT CAT CAT CAA TAA
TAT ACC-3'
```

Amplification was done with pfx DNA polymerase (LTI) according to manufacturer's instructions but with 0.6 µM of both primers and 3% DMSO using 10 ngr. of wt Ad35 DNA as template. The program was as follows: 3 min. at 94° C. and 5 cycles of 30 sec. at 94° C., 45 sec. at 40° C., 2 min. 45 sec. at 68° C. followed by 25 cycles of 30 sec. at 94° C., 30 sec. at 60° C., 2 min. 45 sec. at 68° C. To enable cloning in the TA-cloning vector PCR2.1, a last incubation with 1 unit superTaq polymerase for 10 min. at 72° C. was performed. The 1.6 kb amplified fragment ranging from nucleotides 33178 to the end of the right ITR of Ad35, was purified using the purification kit (LTI).

Figure 7:
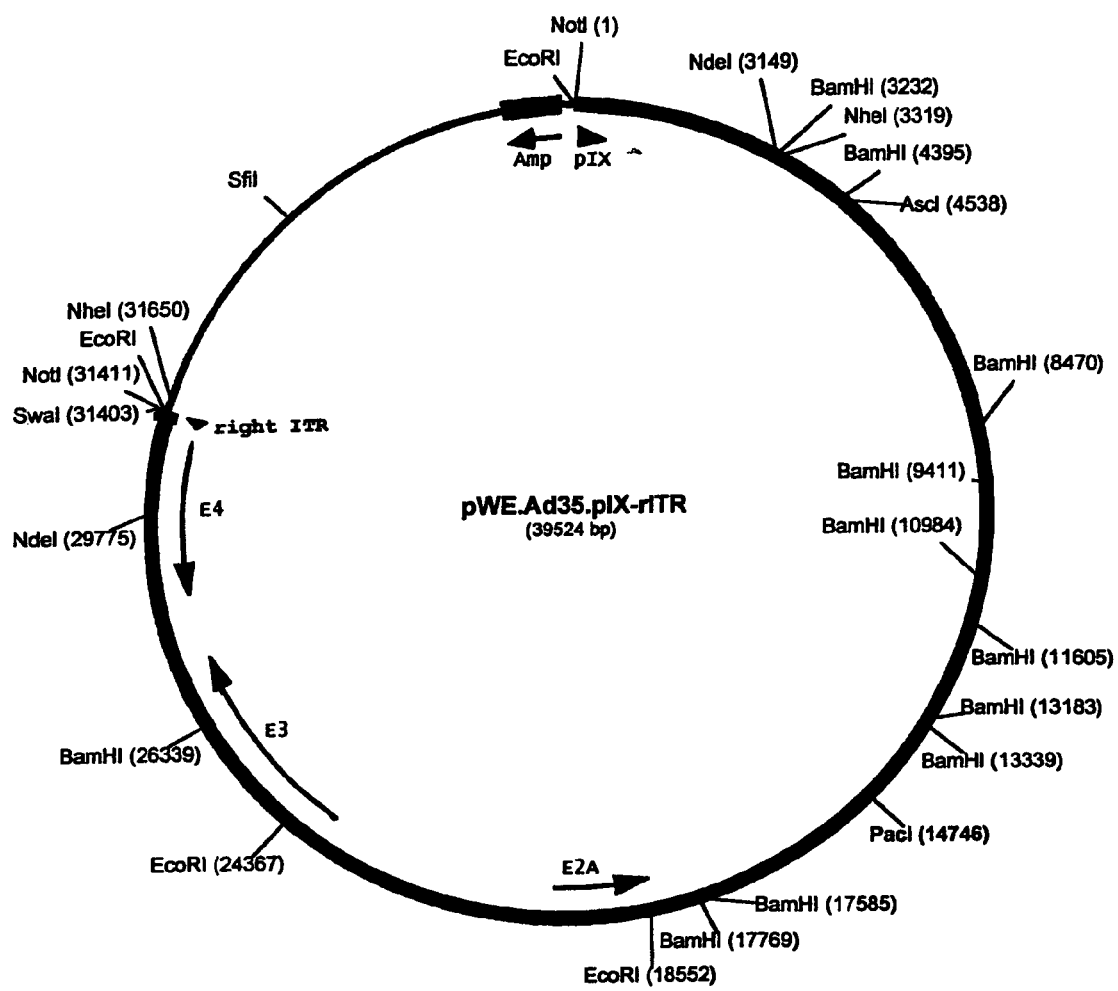
FIG. 7: Map of pWE.Ad35.pIX-rITR.

Both purified PCR fragments were ligated into the PCR2.1 vector of the TA-cloning kit (Invitrogen) and transformed into STBL-2 competent cells (LTI). Clones containing the expected insert were sequenced to confirm correct amplification. Next, both fragments were excised from the vector by digestion with NotI and NdeI and purified from gel using the GENECLEAN kit (BIO 101, Inc.). Cosmid vector pWE15 (Clontech) was digested with NotI, dephosphorylated and also purified from gel. These three fragments were ligated and transformed into STBL2 competent cells (LTI). One of the correct clones that contained both PCR fragments was then digested with NdeI, and the linear fragment was purified from gel using the GENECLEAN kit. Ad35 wt DNA was digested with NdeI and the 26.6 kb fragment was purified from LMP gel using agarase enzyme (Roche) according to the manufacturer's instructions. These fragments were ligated together and packaged using λ1 phage packaging extracts (Stratagene) according to the manufacturer's protocol. After infection into STBL-2 cells, colonies were grown on plates and analyzed for presence of the complete insert. One clone with the large fragment inserted in the correct orientation and having the correct restriction patterns after independent digestions with three enzymes (NcoI, PvuII and ScaI) was selected. This clone is designated pWE.Ad35.pIX-rITR. It contains the Ad35 sequences from bp 3401 to the end and is flanked by NotI sites (FIG. 7).

3) Generation of Ad35-Based Recombinant Viruses on PER.C6.

Wild type Ad35 virus can be grown on PER.C6 packaging cells to very high titers. However, whether the Ad5-E1 region that is present in PER.C6 is able to complement E1-deleted Ad35 recombinant viruses is unknown. To test this, PER.C6 cells were cotransfected with the above-described adapter plasmid pAdApt35.LacZ and the large backbone fragment pWE.Ad35.pIX-rITR. First, pAdApt35.LacZ was digested with PacI and pWE.Ad35.pIX-rITR was digested with NotI. Without further purification, 4 µgr of each construct was mixed with DMEM (LTI) and transfected into PER.C6 cells, seeded at a density of 5×10$^6$ cells in a T25 flask the day before, using Lipofectamin (LTI) according to the manufacturer's instructions. As a positive control, 6 µgr of PacI digested pWE.Ad35.pIX-rITR DNA was cotransfected with a 6.7 kb NheI fragment isolated from Ad35 wt DNA containing the left end of the viral genome including the E1 region. The next day, medium (DMEM with 10% FBS and 10 mM MgCl$_2$) was refreshed and cells were further incubated. At day 2 following the transfection, cells were trypsinized and transferred to T80 flasks. The positive control flask showed CPE at five days following transfection, showing that the pWE.Ad35.pIX-rITR construct is functional, at least in the presence of Ad35-E1 proteins. The transfection with the Ad35 LacZ adapter plasmid and pWE.Ad35.pIX-rITR did not give rise to CPE. These cells were harvested in the medium at day 10 and freeze/thawed once to release virus from the cells. 4 ml of the harvested material was added to a T80 flask with PER.C6 cells (at 80% confluency) and incubated for another five days. This harvest/re-infection was repeated two times but there was no evidence for virus associated CPE.

From this experiment, it seems that the Ad5-E1 proteins are not, or not well enough, capable of complementing Ad35 recombinant viruses. However, it may be that the sequence overlap of the adapter plasmid and the pWE.Ad35.pIX-rITR backbone plasmid is not large enough to efficiently recombine and give rise to a recombinant virus genome. The positive control transfection was done with a 6.7 kb left end fragment and, therefore, the sequence overlap was about 3.5 kb. The adapter plasmid and the pWE.Ad35.pIX-rITR fragment have a sequence overlap of 1.3 kb. To check whether the sequence overlap of 1.3 kb is too small for efficient homologous recombination, a co-transfection was done with PacI digested pWE.Ad35.pIX-rITR and a PCR fragment of Ad35 wt DNA generated with the above-mentioned 35F1 and 35R4 using the same procedures as previously described herein. The PCR fragment thus contains left end sequences up to bp 4669 and, therefore, has the same overlap sequences with pWE.Ad35.pIX-rITR as the adapter plasmid pAdApt35.LacZ, but has Ad35-E1 sequences. Following PCR column purification, the DNA was digested with SalI to remove possible intact template sequences. A transfection with the digested PCR product alone served as a negative control. Four days after the transfection, CPE occurred in the cells transfected with the PCR product and the Ad35 pIX-rITR fragment, and not in the negative control. This result shows that a 1.3 kb overlapping sequence is sufficient to generate viruses in the presence of Ad35-E1 proteins. From these experiments, we conclude that the presence of at least one of the Ad35-E1 proteins is necessary to generate recombinant Ad35 based vectors from plasmid DNA on Ad5 complementing cell lines.

Example 5

1) Construction of Ad35-E1 Expression Plasmids

Since Ad5-E1 proteins in PER.C6 are incapable of complementing Ad35 recombinant viruses efficiently, Ad35-E1 proteins have to be expressed in Ad5 complementing cells (e.g., PER.C6). Alternatively, a new packaging cell line expressing Ad35-E1 proteins has to be made, starting from either diploid primary human cells or established cell lines not expressing adenovirus E1 proteins. To address the first possibility, the Ad35-E1 region was cloned in expression plasmids as described below.

First, the Ad35-E1 region from bp 468 to bp 3400 was amplified from wt Ad35 DNA using the following primer set:

```
35F11:                                    (SEQ ID NO:20)
5'-GGG GTA CCG AAT TCT CGC TAG GGT ATT TAT ACC-3'

35F10:                                    (SEQ ID NO:21)
5'-GCT CTA GAC CTG CAG GTT AGT CAG TTT CTT CTC CAC
TG-3'
```

This PCR introduces a KpnI and EcoRI site at the 5' end and an SbfI and XbaI site at the 3' end.

Amplification on 5 ngr. template DNA was done with Pwo DNA polymerase (Roche) using the manufacturer's instructions, however, with both primers at a final concentration of 0.6 μM. The program was as follows: 2 min. at 94° C., 5 cycles of 30 sec. at 94° C., 30 sec. at 56° C. and 2 min. at 72° C., followed by 25 cycles of 30 sec. at 94° C., 30 sec. at 60° C. and 2 min. at 72° C., followed by 10 min. at 72° C. PCR product was purified by a PCR purification kit (LTI) and digested with KpnI and XbaI. The digested PCR fragment was then ligated to the expression vector pRSVhbvNeo (see below) also digested with KpnI and XbaI. Ligations were transformed into competent STBL-2 cells (LTI) according to manufacturer's instructions and colonies were analyzed for the correct insertion of Ad35-E1 sequences into the polylinker in between the RSV promoter and HBV polyA.

Figure 8:
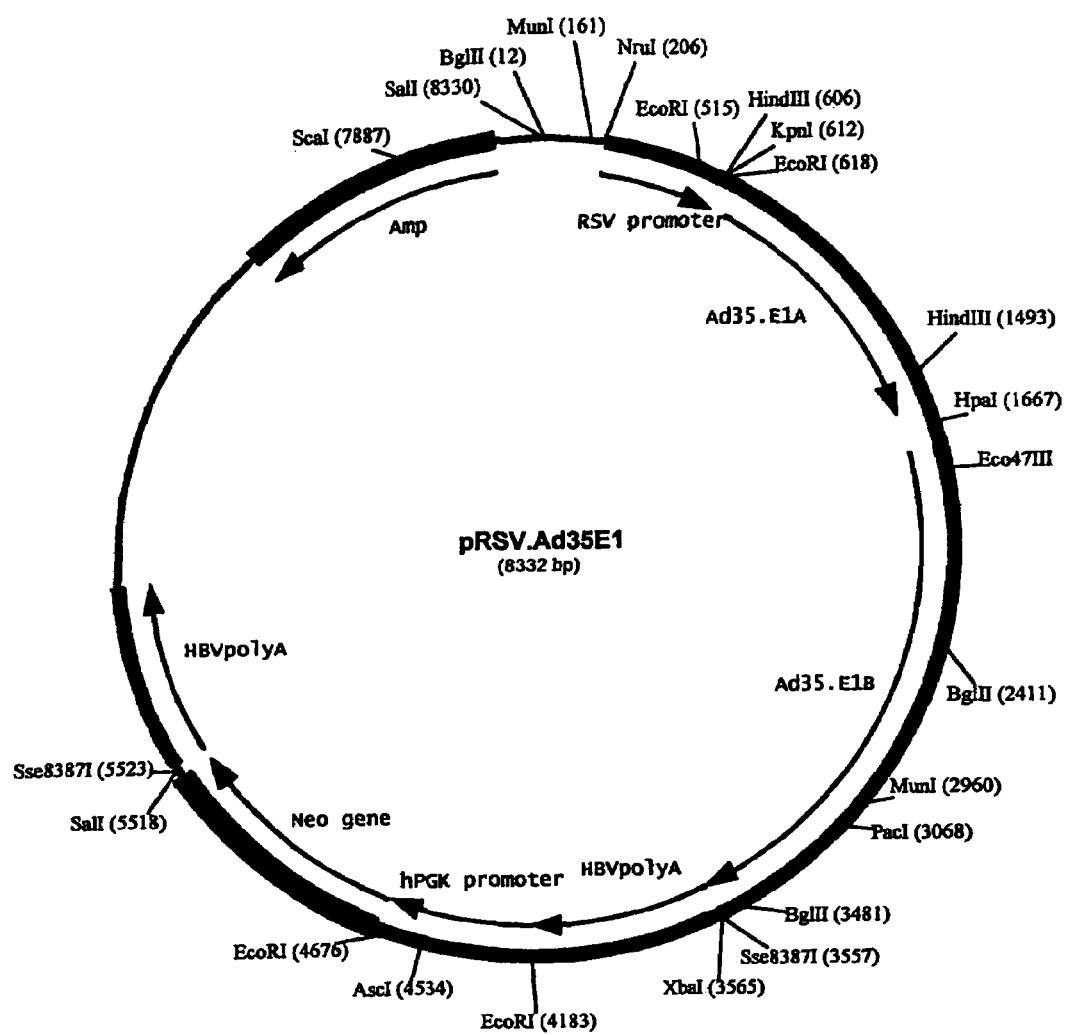
FIG. 8: Map of pRSV.Ad35-E1.
Figure 9:
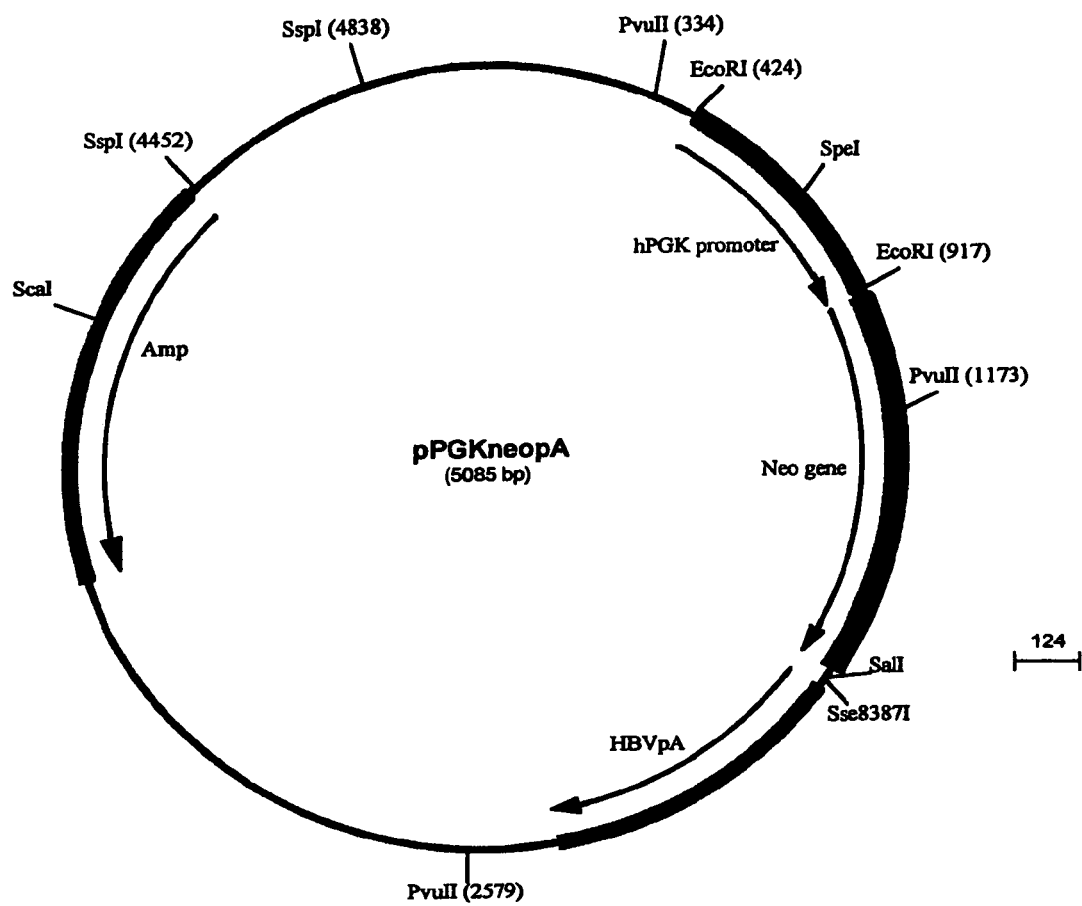
FIG. 9: Map of pPGKneopA.
Figure 10:
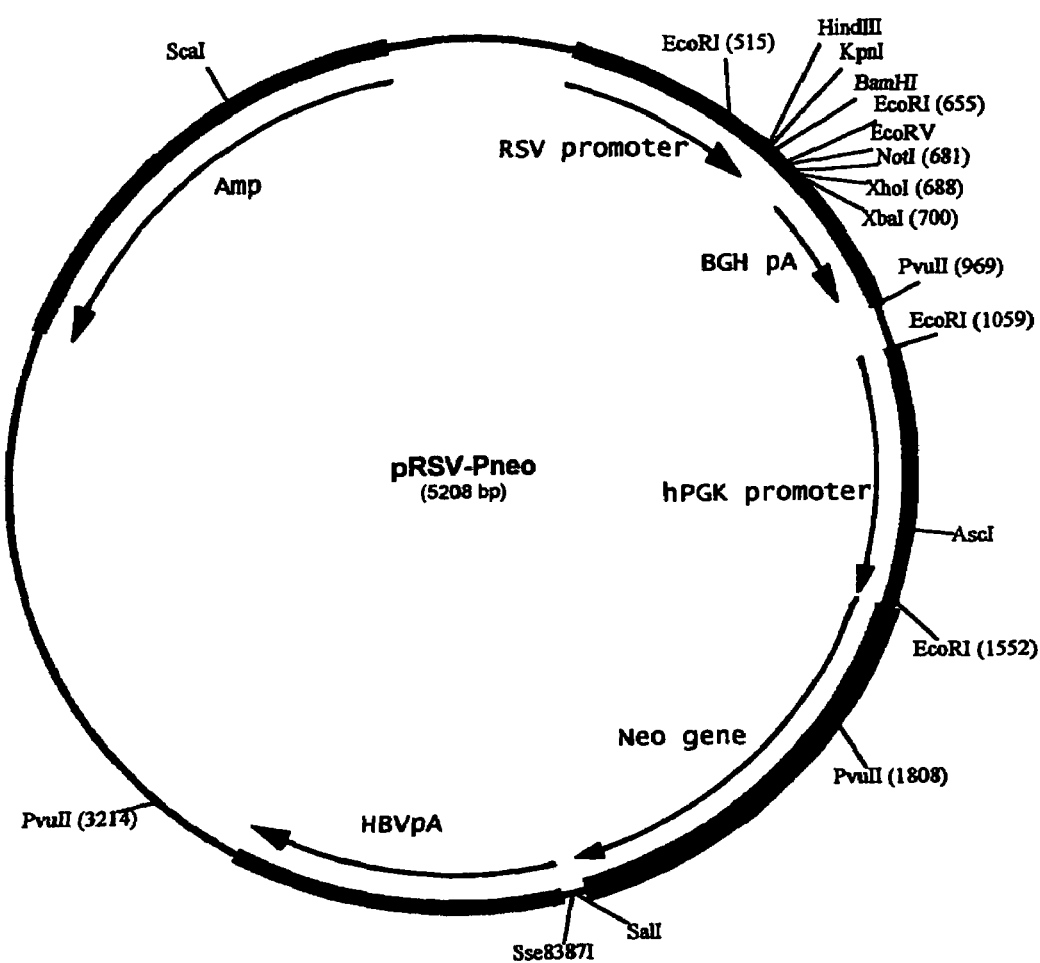
FIG. 10: Map of pRSV-PNeo.

The resulting clone was designated pRSV.Ad35-E1 (FIG. 8). The Ad35 sequences in pRSV.Ad35-E1 were checked by sequence analysis.

pRSVhbvNeo was generated as follows: pRc-RSV (Invitrogen) was digested with PvuII, dephosphorylated with TSAP enzyme (LTI), and the 3 kb vector fragment was isolated in low melting point agarose (LMP). Plasmid pPGKneopA (FIG. 9; described in PCT International Patent Application WO96/35798) was digested with SspI completely to linearize the plasmid and facilitate partial digestion with PvuII. Following the partial digestion with PvuII, the resulting fragments were separated on a LMP agarose gel and the 2245 bp PvuII fragment, containing the PGK promoter, neomycin-resistance gene and HBVpolyA, was isolated. Both isolated fragments were ligated to give the expression vector pRSV-pNeo that now has the original SV40prom-neo-SV40polyA expression cassette replaced by a PGKprom-neo-HBVpolyA cassette (FIG. 10). This plasmid was further modified to replace the BGHpA with the HBVpA as follows: pRSVpNeo was linearized with ScaI and further digested with XbaI. The 1145 bp fragment, containing part of the Amp gene and the RSV promoter sequences and polylinker sequence, was isolated from gel using the GENECLEAN kit (Bio Inc. 101). Next, pRSVpNeo was linearized with ScaI and further digested partially with EcoRI and the 3704 bp fragment containing the PGK-neo cassette and the vector sequences were isolated from gel as above. A third fragment, containing the HBV polyA sequence flanked by XbaI and EcoRI at the 5' and 3' end, respectively, was then generated by PCR amplification on pRSVpNeo using the following primer set:

```
HBV-F:                                    (SEQ ID NO:22)
5'-GGC TCT AGA GAT CCT TCG CGG GAC GTC-3'  and HBV-R:                                    (SEQ ID NO:23)
5'-GGC GAA TTC ACT GCC TTC CAC CAA GC-3'.
```

Figure 11:
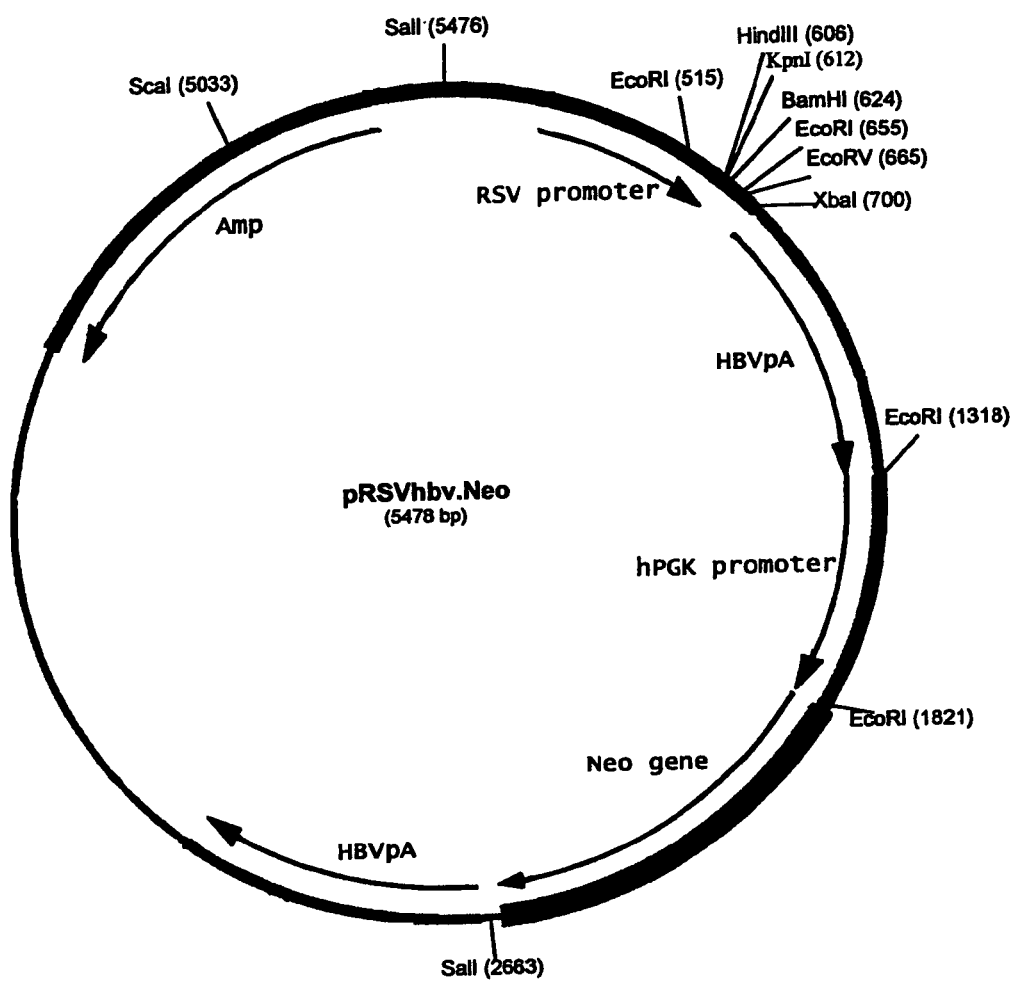
FIG. 11: Map of pRSVhbv.Neo.

Amplification was done with Elongase enzyme (LTI) according to the manufacturer's instructions with the following conditions: 30 seconds at 94° C., then 5 cycles of 45 seconds at 94° C., 1 minute at 42° C. and 1 minute at 68° C., followed by 30 cycles of 45 seconds at 94° C., 1 minute at 65° C. and 1 minute at 68° C., followed by 10 minutes at 68° C. The 625 bp PCR fragment was then purified using the Qiaquick PCR purification kit, digested with EcoRI and XbaI and purified from gel using the GENECLEAN kit. The three isolated fragments were ligated and transformed into DH5α competent cells (LTI) to give the construct pRSVhbvNeo (FIG. 11). In this construct, the transcription regulatory regions of the RSV expression cassette and the neomycin selection marker are modified to reduce overlap with adenoviral vectors that often contain CMV and SV40 transcription regulatory sequences.

2) Generation of Ad35 Recombinant Viruses on PER.C6 Cells Cotransfected with an Ad35-E1 Expression Construct.

PER.C6 cells were seeded at a density of $5 \times 10^6$ cells in a T25 flask and, the next day, transfected with a DNA mixture containing:

1 μg pAdApt35.LacZ digested with PacI
5 μg pRSV.Ad35E1 undigested
2 μg pWE.Ad35.pIX-rITR digested with NotI Transfection was done using Lipofectamine according to the manufacturer's instructions. Five hours after addition of the transfection mixture to the cells, medium was removed and replaced by fresh medium. After two days, cells were transferred to T80 flasks and further cultured. One week post-transfection, 1 ml of the medium was added to A549 cells and, the following day, cells were stained for LacZ expression. Blue cells were clearly visible after two hours of staining indicating that recombinant LacZ expressing viruses were produced. The cells were further cultured, but no clear appearance of CPE was noted. However, after 12 days, clumps of cells appeared in the monolayer and 18 days following transfection, cells were detached. Cells and medium were then harvested, freeze-thawed once, and 1 ml of the crude lysate was used to infect PER.C6 cells in a 6-well plate. Two days after infection, cells were stained for LacZ activity. After two hours, 15% of the cells were stained blue. To test for the presence of wt and/or replicating-competent viruses, A549 cells were infected with these viruses and further cultured. No signs of CPE were found indicating the absence of replication-competent viruses. These experiments show that recombinant AdApt35.LacZ viruses were made on PER.C6 cells co-transfected with an Ad35-E1 expression construct.

Ad35 Recombinant Viruses Escape Neutralization in Human Serum Containing Neutralizing Activity to Ad5 Viruses.

The AdApt35.LacZ viruses were then used to investigate infection in the presence of serum that contains neutralizing activity to Ad5 viruses. Purified Ad5-based LacZ virus served as a positive control for NA. Hereto, PER.C6 cells were seeded in a 24-well plate at a density of 2×10⁵ cells/well. The next day, a human serum sample with high neutralizing activity to Ad5 was diluted in culture medium in five steps of five times dilutions. 0.5 ml of diluted serum was then mixed with 4×10⁶ virus particles AdApt5.LacZ virus in 0.5 ml medium and after 30 minutes of incubation at 37° C., 0.5 ml of the mixture was added to PER.C6 cells in duplicate. For the AdApt35.LacZ viruses, 0.5 ml of the diluted serum samples were mixed with 0.5 ml crude lysate containing AdApt35.LacZ virus and, after incubation, 0.5 ml of this mixture was added to PER.C6 cells in duplo. Virus samples incubated in medium without serum were used as positive controls for infection. After two hours of infection at 37° C., medium was added to reach a final volume of 1 ml and cells were further incubated. Two days after infection, cells were stained for LacZ activity. The results are shown in Table II. From these results, it is clear that whereas AdApt5.LacZ viruses are efficiently neutralized, AdApt35.LacZ viruses remain infectious irrespective of the presence of human serum. This proves that recombinant Ad35-based viruses escape neutralization in human sera that contain NA to Ad5-based viruses.

Example 6

Generation of Cell Lines Capable of Complementing E1-Deleted Ad35 Viruses

Generation of pIG135 and pIG270

Figure 12:
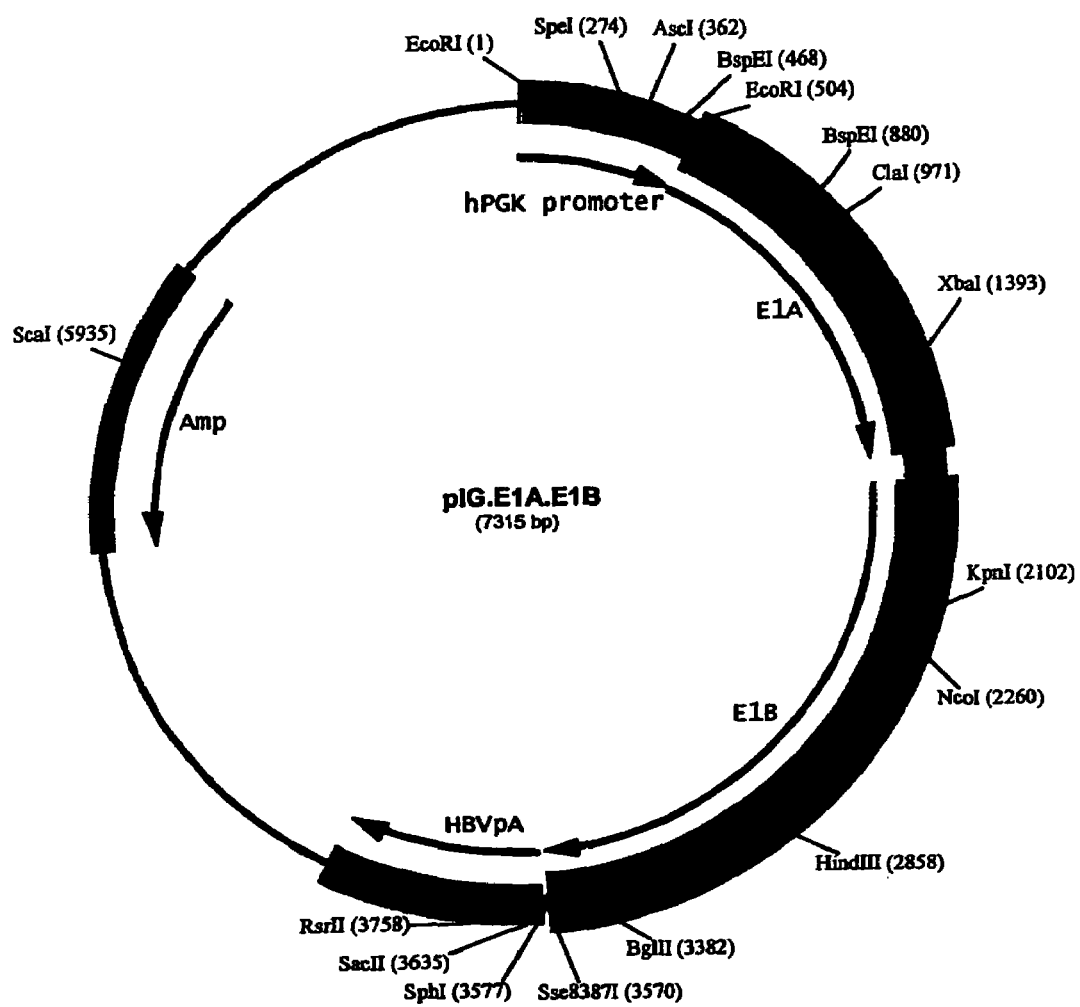
FIG. 12: Map of pIG.E1A.E1B.

Construct pIG.E1A.E1B (FIG. 12) contains E1 region sequences of Ad5 corresponding to nucleotides 459 to 3510 of the wt Ad5 sequence (Genbank accession number M72360) operatively linked to the human phosphoglycerate kinase promoter ("PGK") and the Hepatitis B Virus polyA sequences. The generation of this construct is described in PCT International Patent Application No. WO97/00326. The E1 sequences of Ad5 were replaced by corresponding sequences of Ad35 as follows. pRSV.Ad35-E1 (described in Example 5) was digested with EcoRI and Sse83871 and the 3 kb fragment corresponding to the Ad35 E1 sequences was isolated from gel. Construct pIG.E1A.E1B was digested with Sse83871 completely and partially with EcoRI. The 4.2 kb fragment corresponding to vector sequences without the Ad5-E1 region but retaining the PGK promoter were separated from other fragments on LMP agarose gel and the correct band was excised from gel. Both obtained fragments were ligated resulting in pIG.Ad35-E1.

This vector was further modified to remove the LacZ sequences present in the pUC119 vector backbone. Hereto, the vector was digested with BsaAI and BstXI and the large fragment was isolated from gel. A double stranded oligo was prepared by annealing the following two oligos:

(SEQ ID NO:24)
BB1: 5'-GTG CCT AGG CCA CGG GG-3' and (SEQ ID NO:25)
BB2: 5'-GTG GCC TAG GCA C-3'.

Figure 13:
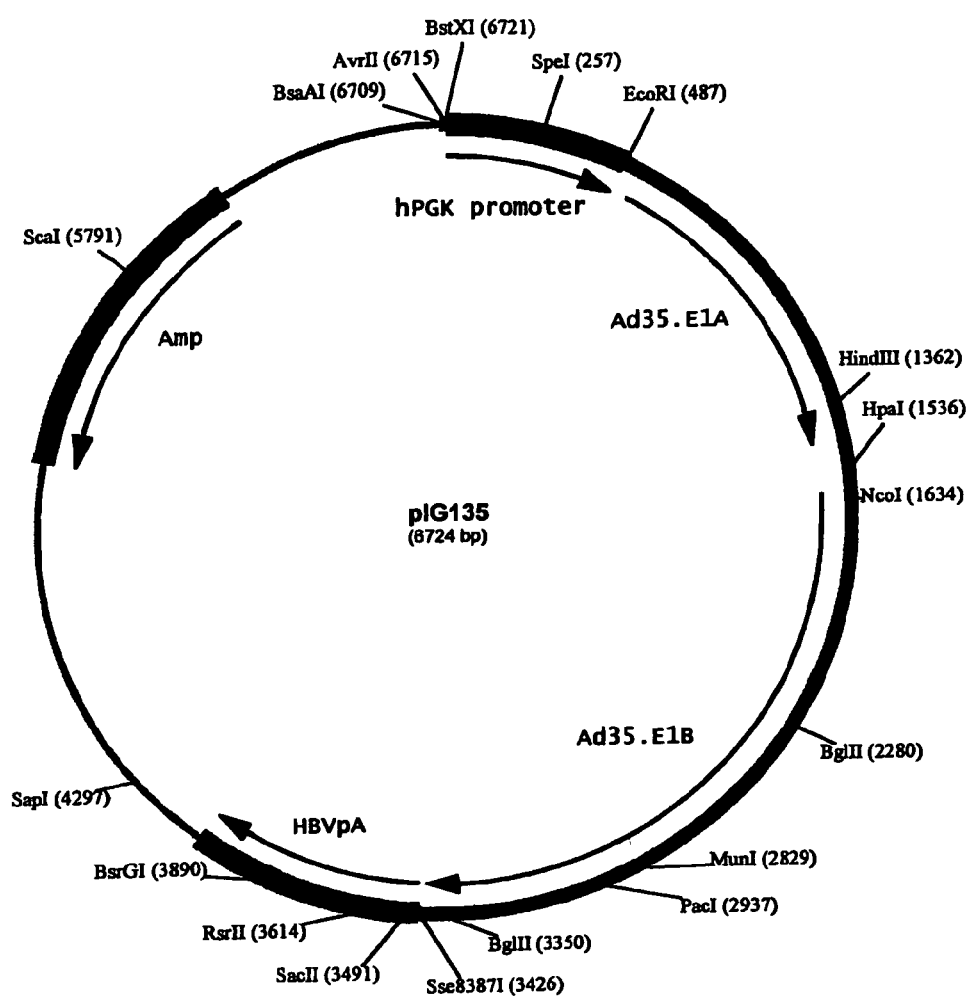
FIG. 13: Map of pIG135.

Ligation of the oligo and the vector fragment resulted in construct pIG135 (FIG. 13). Correct insertion of the oligo restores the BsaAI and BstXI sites and introduces a unique AvrII site. Next, we introduced a unique site at the 3' end of the Ad35-E1 expression cassette in pIG135. Hereto, the construct was digested with SapI and the 3' protruding ends were made blunt by treatment with T4 DNA polymerase. The thus treated linear plasmid was further digested with BsrGI and the large vector-containing fragment was isolated from gel. To restore the 3' end of the HBVpolyA sequence and to introduce a unique site, a PCR fragment was generated using the following primers:

(SEQ ID NO:26)
270F: 5'-CAC CTC TGC CTA ATC ATC TC-3' and (SEQ ID NO:27)
270R: 5'-GCT CTA GAA ATT CCA CTG CCT TCC ACC-3'.

Figure 14:
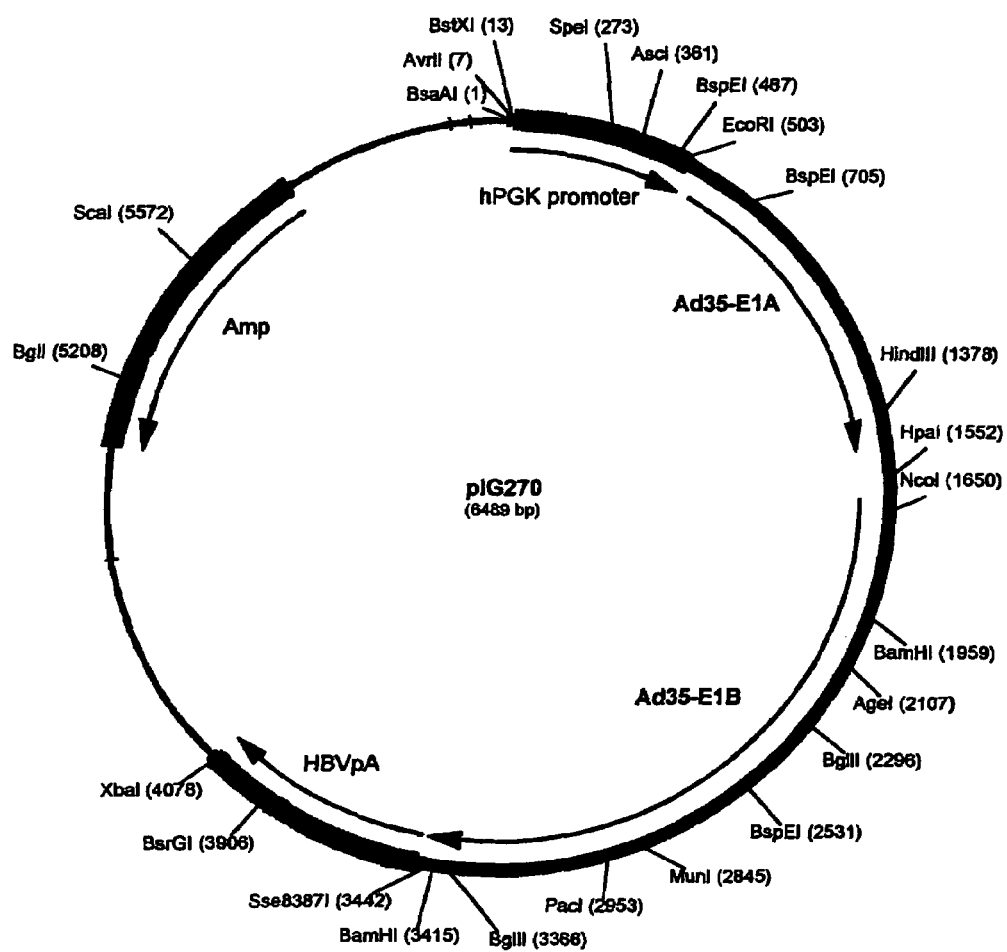
FIG. 14: Map of pIG270.

The PCR was performed on pIG.Ad35.E1 DNA using Pwo polymerase (Roche) according to the manufacturer's instructions. The obtained PCR product was digested with BsrGI and dephosphorylated using Tsap enzyme (LTI), the latter to prevent insert dimerization on the BsrGI site. The PCR fragment and the vector fragment were ligated to yield construct pIG270 (FIG. 14).

Ad35-E1 Sequences are Capable of Transforming Rat Primary Cells

Newborn WAG/RIJ rats were sacrificed at 1 week of gestation and kidneys were isolated. After careful removal of the capsule, kidneys were disintegrated into a single cell suspension by multiple rounds of incubation in trypsin/EDTA (LTI) at 37° C. and collection of floating cells in cold PBS containing 1% FBS. When most of the kidney was trypsinized, all cells were re-suspended in DMEM supplemented with 10% FBS and filtered through a sterile cheesecloth. Baby Rat Kidney (BRK) cells obtained from one kidney were plated in 5 dishes (Greiner, 6 cm). When a confluency of 70-80% was reached, the cells were transfected with 1 or 5 μgr DNA/dish using the $CaPO_4$ precipitation kit (LTI) according to the manufacturer's instructions. The following constructs were used in separate transfections: pIG.E1A.E1B (expressing the Ad5-E1 region), pRSV.Ad35-E1, pIG.Ad35-E1 and pIG270 (expressing the Ad35-E1 region). Cells were incubated at 37° C., 5% $CO_2$ until foci of transformed cells appeared. Table III shows the number of foci that resulted from several transfection experiments using circular or linear DNA. As expected, the Ad5-E1 region efficiently transformed BRK cells. Foci also appeared in the Ad35-E1 transfected cell layer although with lower efficiency. The Ad35 transformed foci appeared at a later time point: ~2 weeks post transfection compared with 7-10 days for Ad5-E1. These experiments clearly show that the E1 genes of the B group virus Ad35 are capable of transforming primary rodent cells. This proves the functionality of the Ad35-E1 expression constructs and confirms earlier findings of the transforming capacity of the B-group viruses Ad3 and Ad7 (Dijkema, 1979). To test whether the cells in the foci were really transformed, a few foci, were picked and expanded. From the 7 picked foci at least 5 turned out to grow as established cell lines.

Generation of New Packaging Cells Derived from Primary Human Amniocytes

Amniotic fluid obtained after amniocentesis was centrifuged and cells were re-suspended in AmnioMax medium (LTI) and cultured in tissue culture flasks at 37° C. and 10% $CO_2$. When cells were growing nicely (approximately one cell division/24 hrs.), the medium was replaced with a 1:1 mixture of AmnioMax complete medium and DMEM low glucose medium (LTI) supplemented with Glutamax I (end concentration 4 mM, LTI) and glucose (end concentration 4.5 gr/L, LTI) and 10% FBS (LTI). For transfection ~5×10⁵ cells were plated in 10 cm tissue culture dishes. The day after, cells were transfected with 20 μgr of circular pIG270/dish using the $CaPO_4$ transfection kit (LTI) according to manufacturer's instructions and cells were incubated overnight with the DNA precipitate. The following day, cells were washed 4 times with PBS to remove the precipitate and further incubated for over three weeks until foci of transformed cells appeared. Once a week the medium was replaced by fresh medium. Other transfection agents like, but not limited to, LipofectAmine (LTI) or PEI (Polyethylenimine, high molecular weight, water-free, Aldrich) were used. Of these three agents, PEI reached the best transfection efficiency on primary human amniocytes: ~1% blue cells 48 hrs.

Following Transfection of pAdApt35. LacZ.

Foci are isolated as follows. The medium is removed and replaced by PBS after which foci are isolated by gently scraping the cells using a 50-200 µl Gilson pipette with a disposable filter tip. Cells contained in ~10 µml PBS were brought in a 96 well plate containing 15 µl trypsin/EDTA (LTI) and a single cell suspension was obtained by pipetting up and down and a short incubation at room temperature. After addition of 200 µl of the above described 1:1 mixture of AmnioMax complete medium and DMEM with supplements and 10% FBS, cells were further incubated. Clones that continued to grow were expanded and analyzed for their ability to complement growth of E1-deleted adenoviral vectors of different sub-groups, specifically ones derived from B-group viruses and, more specifically, from Ad35 or Ad11.

Generation of New Packaging Cell Lines from HER Cells

HER cells are isolated and cultured in DMEM medium supplemented with 10% FBS (LTI). The day before transfection, ~5×10$^5$ cells are plated in 6 cm dishes and cultured overnight at 37° C. and 10% $CO_2$. Transfection is done using the $CaPO_4$ precipitation kit (LTI) according to the manufacturer's instructions. Each dish is transfected with 8-10 µmgr pIG270 DNA, either as a circular plasmid or as a purified fragment. To obtain the purified fragment, pIG270 was digested with AvrII and XbaI and the 4 kb fragment corresponding to the Ad35-E1 expression cassette was isolated from gel by agarase treatment (Roche). The following day, the precipitate is washed away carefully by four washes with sterile PBS. Then fresh medium is added and transfected cells are further cultured until foci of transformed cells appear. When large enough (>100 cells), foci are picked and brought into 96-wells as described above. Clones of transformed HER cells that continue to grow are expanded and tested for their ability to complement growth of E1-deleted adenoviral vectors of different sub-groups, specifically ones derived from B-group viruses and, more specifically, from Ad35 or Ad11.

New Packaging Cell Lines Derived from PER.C6

As described in Example 5, it is possible to generate and grow Ad35-E1-deleted viruses on PER.C6 cells with cotransfection of an Ad35-E1 expression construct, e.g., pRSV.Ad35.E1. However, large-scale production of recombinant adenoviruses using this method is cumbersome because, for each amplification step, a transfection of the Ad35-E1 construct is needed. In addition, this method increases the risk of non-homologous recombination between the plasmid and the virus genome with high chances of generation of recombinant viruses that incorporate E1 sequences resulting in replication-competent viruses. To avoid this, the expression of Ad35-E1 proteins in PER.C6 has to be mediated by integrated copies of the expression plasmid in the genome. Since PER.C6 cells are already transformed and express Ad5-E1 proteins, addition of extra Ad35-E1 expression may be toxic for the cells. However, it is not impossible to stably transfect transformed cells with E1 proteins since Ad5-E1-expressing A549 cells have been generated.

Figure 15:
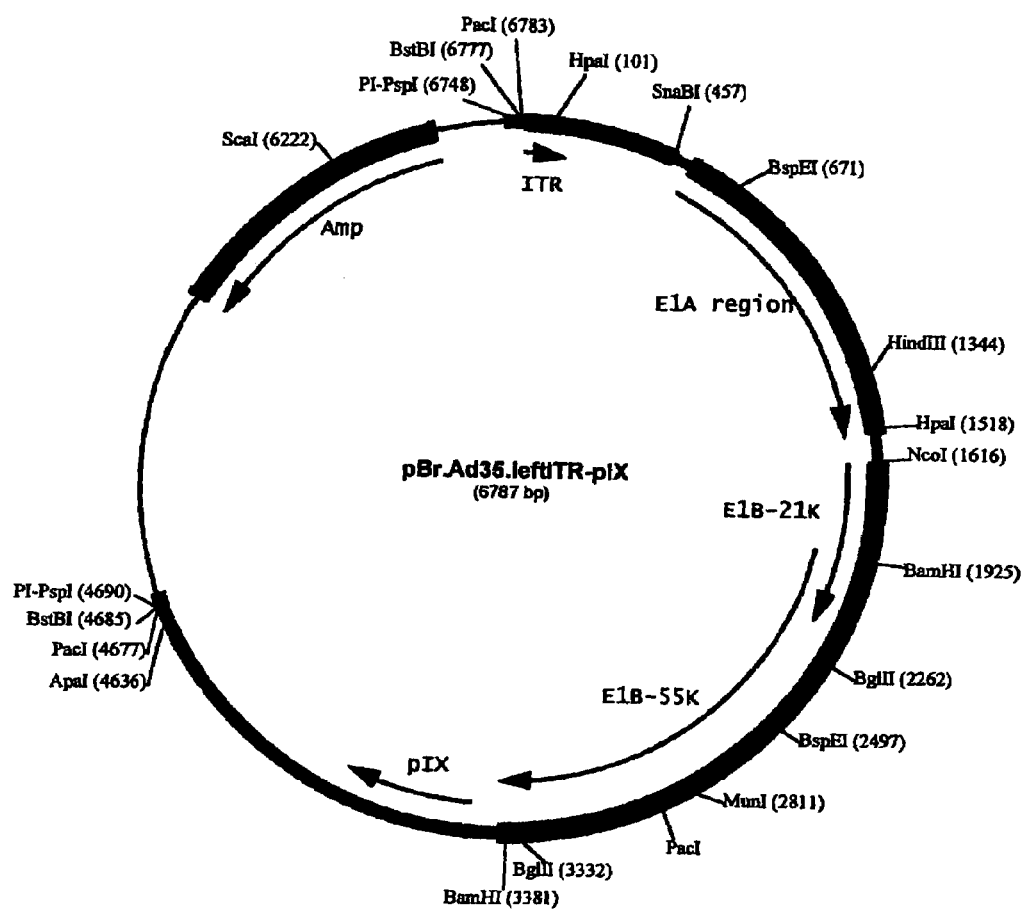
FIG. 15: Map of pBr.Ad35.leftITR-pIX.
Figure 16:
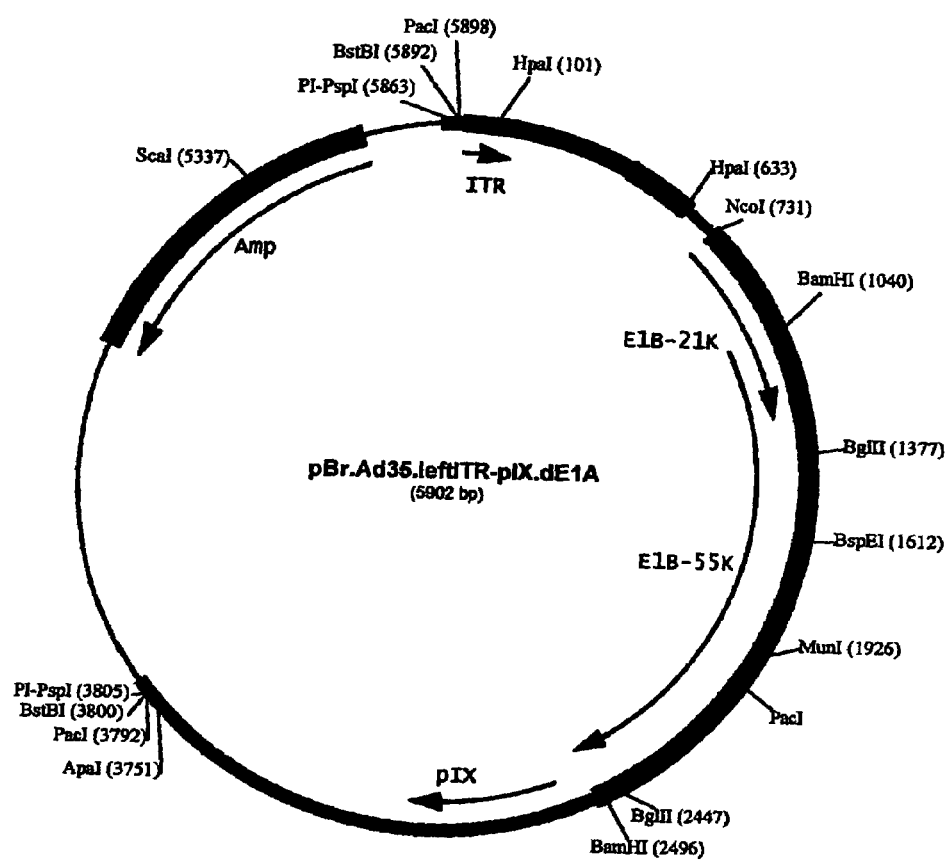
FIG. 16: Map of pBr.Ad35.leftITR-pIXdE1A.

In an attempt to generate recombinant adenoviruses derived from subgroup B virus Ad7, Abrahamsen et al. (1997) were not able to generate E1-deleted viruses on 293 cells without contamination of wt Ad7. Viruses that were picked after plaque purification on 293-ORF6 cells (Brough et al., 1996) were shown to have incorporated Ad7-E1B sequences by nonhomologous recombination. Thus, efficient propagation of Ad7 recombinant viruses proved possible only in the presence of Ad7-E1B expression and Ad5-E4-ORF6 expression. The E1B proteins are known to interact with cellular as well as viral proteins (Bridge et al., 1993; White, 1995). Possibly, the complex formed between the E1B-55K protein and E4-ORF6 which is necessary to increase mRNA export of viral proteins and to inhibit export of most cellular mRNAs is critical and, in some way, serotype-specific. The above experiments suggest that the E1A proteins of Ad5 are capable of complementing an Ad7-E1A deletion and that Ad7-E1B expression in adenovirus packaging cells on itself is not enough to generate a stable complementing cell line. To test whether one or both of the Ad35-E1B proteins is/are the limiting factor in efficient Ad35 vector propagation on PER.C6 cells, we have generated an Ad35 adapter plasmid that does contain the E1B promoter and E1B sequences but lacks the promoter and the coding region for E1A. Hereto, the left end of wt Ad35 DNA was amplified using the primers 35F1 and 35R4 (both described in Example 4) with Pwo DNA polymerase (Roche) according to the manufacturer's instructions. The 4.6 kb PCR product was purified using the PCR purification kit (LTI) and digested with SnaBI and ApaI enzymes. The resulting 4.2 kb fragment was then purified from gel using the QIAExII kit (Qiagen). Next, pAdApt35IP1 (Example 4) was digested with SnaBI and ApaI and the 2.6 kb vector-containing fragment was isolated from gel using the GENECLEAN kit (BIO 101, Inc). Both isolated fragments were ligated to give pBr/Ad35.leftITR-pIX (FIG. 15). Correct amplification during PCR was verified by a functionality test as follows: The DNA was digested with BstBI to liberate the Ad35 insert from vector sequences and 4 µg of this DNA was cotransfected with 4 µg of NotI digested pWE/Ad35.pIX-rITR (Example 4) into PER.C6 cells. The transfected cells were passaged to T80 flasks at day 2 and again two days later CPE had formed showing that the new pBr/Ad35.leftITR-pIX construct contains functional E1 sequences. The pBr/Ad35.leftITR-pIX construct was then further modified as follows. The DNA was digested with SnaBI and HindIII and the 5' HindII overhang was filled in using Klenow enzyme. Religation of the digested DNA and transformation into competent cells (LTI) gave construct pBr/Ad35leftITR-pIXΔE1A (FIG. 16). This latter construct contains the left end 4.6 kb of Ad35 except for E1A sequences between bp 450 and 1341 (numbering according to wt Ad35) and thus lacks the E1A promoter and most of the E1A coding sequences. pBr/Ad35.leftITR-pIXΔE1A was then digested with BstBI and 2 mg of this construct was cotransfected with 6 mmgr of NotI digested pWE/Ad35.pIX-rITR (Example 4) into PER.C6 cells. One week following transfection, full CPE had formed in the transfected flasks.

This experiment shows that the Ad35-E1A proteins are functionally complemented by Ad5-E1A expression in PER.C6 cells and that at least one of the Ad35-E1B proteins cannot be complemented by Ad5-E1 expression in PER.C6. It further shows that it is possible to make a complementing cell line for Ad35-E1-deleted viruses by expressing Ad35-E1B proteins in PER.C6. Stable expression of Ad35-E1B sequences from integrated copies in the genome of PER.C6 cells may be driven by the E1B promoter and terminated by a heterologous poly-adenylation signal like, but not limited to, the HBVpA. The heterologous pA signal is necessary to avoid overlap between the E1B insert and the recombinant vector, since the natural E1B termination is located in the pIX transcription unit that has to be present on the adenoviral vector. Alternatively, the E1B sequences may be driven by a heterologous promoter like, but not limited to, the human PGK promoter or by an inducible promoter like, but not limited to the 7xtetO promoter (Gossen and Bujard, 1992). Also, in these cases, the transcription termination is mediated by a heterologous pA sequence, e.g., the HBV pA. The Ad35-E1B sequences at least comprise one of the coding regions of the E1B-21K and the E1B-55K proteins located between nucleotides 1611 and 3400 of the wt Ad35 sequence. The insert may also include part of the Ad35-E1B sequences between nucleotides 1550 and 1611 of the wt Ad35 sequence.

Example 7

Ad35-Based Viruses Deleted for E1A and E1B-21K Genes Efficiently Propagate on Ad5 Complementing Cell Lines.

The generation of Ad35-based viruses that are deleted for E1A and retain the full E1B region is described in Example 6 of this application. Such viruses can be generated and propagated on the Ad5 complementing cell line PER.C6. The E1B region comprises partially overlapping coding sequences for the two major proteins 21K and 55K (Bos et al., 1981). Whereas, during productive wt adenoviral infection, both 21K and 55K are involved in counteracting the apoptose-inducing effects of E1A proteins, the E1B-55K protein has been suggested to have additional functions during the late phase of virus infection. These include the accumulation of viral mRNAs, the control of late viral gene expression and the shutoff of most host mRNAs at the level of mRNA transport (Babiss et al., 1984, 1985; Pilder et al., 1986). A complex formed between E1B-55K and the ORF6 protein encoded by the adenovirus early region 4 (Leppard and Shenk, 1989; Bridge and Ketner, 1990) exerts at least part of these functions.

To analyze which of the E1B proteins is required for propagation of Ad35-E1A-deleted recombinant viruses on PER.C6 packaging cells, the E1B region in construct pBr.Ad35.leftITR-pIXΔE1A (see Example 6 and FIG. 16) was further deleted. A first construct, pBr.Ad35Δ21K, retains the full E1B-55K sequence and is deleted for E1A and E1B-21K. Hereto, pBr.Ad35.leftITR-pIXΔE1A was digested with NcoI and BspE1 and the 5 KB vector fragment was isolated from agarose gel using the GENECLEAN kit (BIO 101, Inc.) according to the manufacturer's instructions. Then a PCR fragment was generated with pBr.Ad35.leftITR-pIXΔE1A as template DNA using the following primers:

```
                                              (SEQ ID NO:28)
35D21: 5'-TTA GAT CCA TGG ATC CCG CAG ACT C-3' and (SEQ ID NO:29)
35B3: 5'-CCT CAG CCC CAT TTC CAG-3'.
```

Amplification was done using Pwo DNA polymerase (Roche) according to manufacturer's recommendations with the addition of DMSO (final concentration 3%) in the reaction mixture. The PCR program was as follows: 94° C. for 2', then 30 cycles of 94° C. for 30", 58° C. for 30" and 72° C. for 45" and a final step at 68° C. for 8' to ensure blunt ends.

Figure 17:
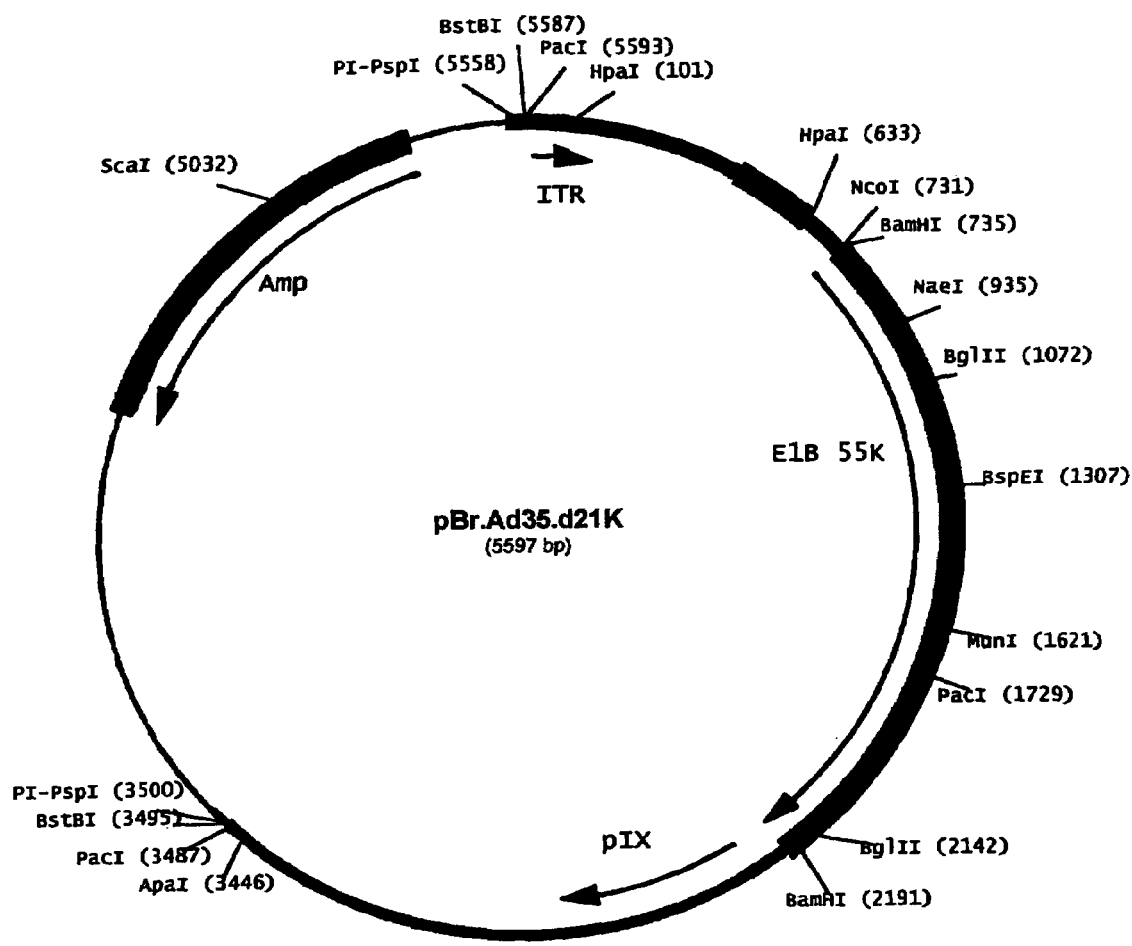
FIG. 17: Map of pBr.Ad35.d21K.

This PCR amplifies Ad35-E1B sequences from nucl. 1908 to 2528 (sequence Ad35 SEQ ID NO:39) and introduces an NcoI site at the start codon of the E1B-55K coding sequence (bold in primer 35D21). The 620 bp PCR fragment was purified using the PCR purification kit (Qiagen) and then digested with NcoI and BspEI, purified from agarose gel as above and ligated to the above-described NcoI/BspE1 digested vector fragment to give pBr.Ad35Δ21K (FIG. 17).

Figure 18:
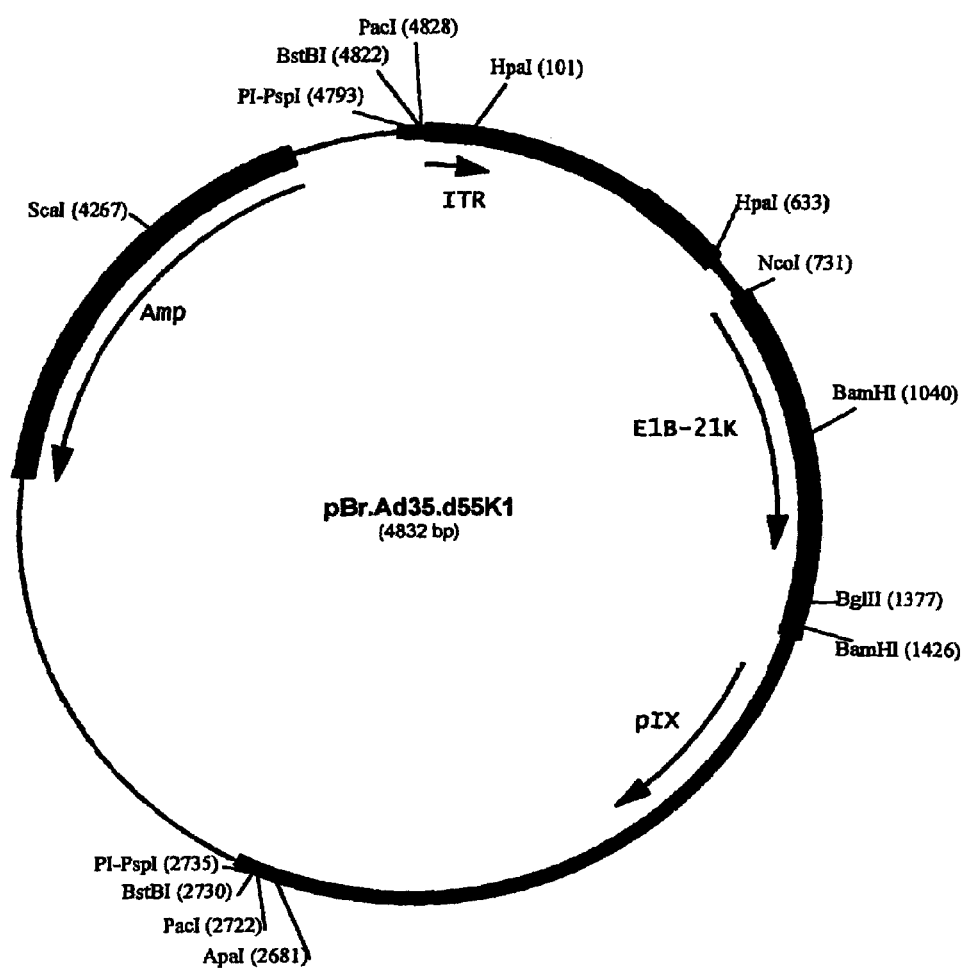
FIG. 18: Map of pBr.Ad35.d55K1.

Since the coding regions of the 21K and 55K proteins overlap, it is only possible to delete part of the 55K coding sequences while retaining 21K. Hereto, pBr.Ad35.leftITR-pIXΔE1A was digested with BglII and the vector fragment was religated to give pBr.Ad35Δ55K1 (FIG. 18). This deletion removes E1B coding sequences from nucl. 2261 to 3330 (Ad35 sequence SEQ ID NO:39). In this construct the N-terminal 115 amino acids are retained and become fused to 21 additional amino acids out of the proper reading frame before a stop codon is encountered. The 21K coding region is intact in construct pBr.Ad35Δ55K1.

Figure 19:
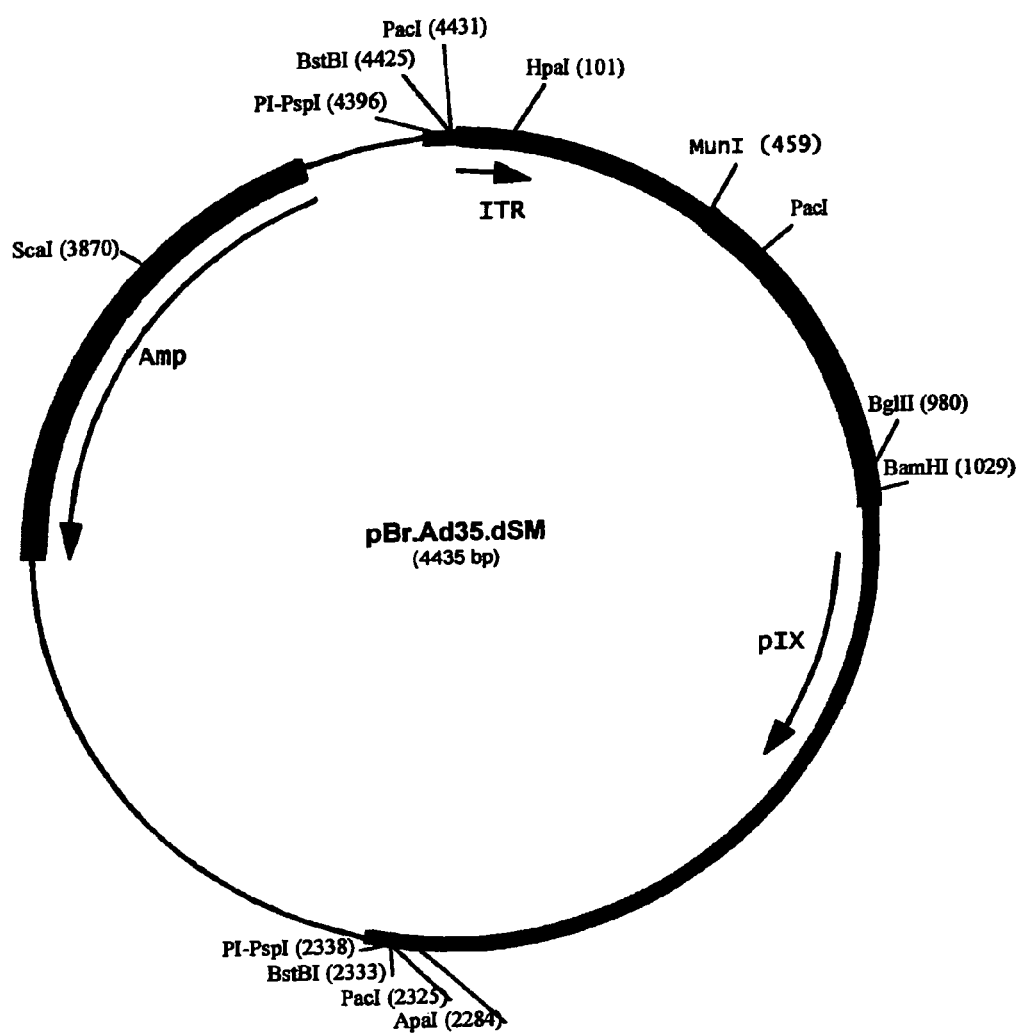
FIG. 19: Map of pBr.Ad35.dSM.
Figure 20:
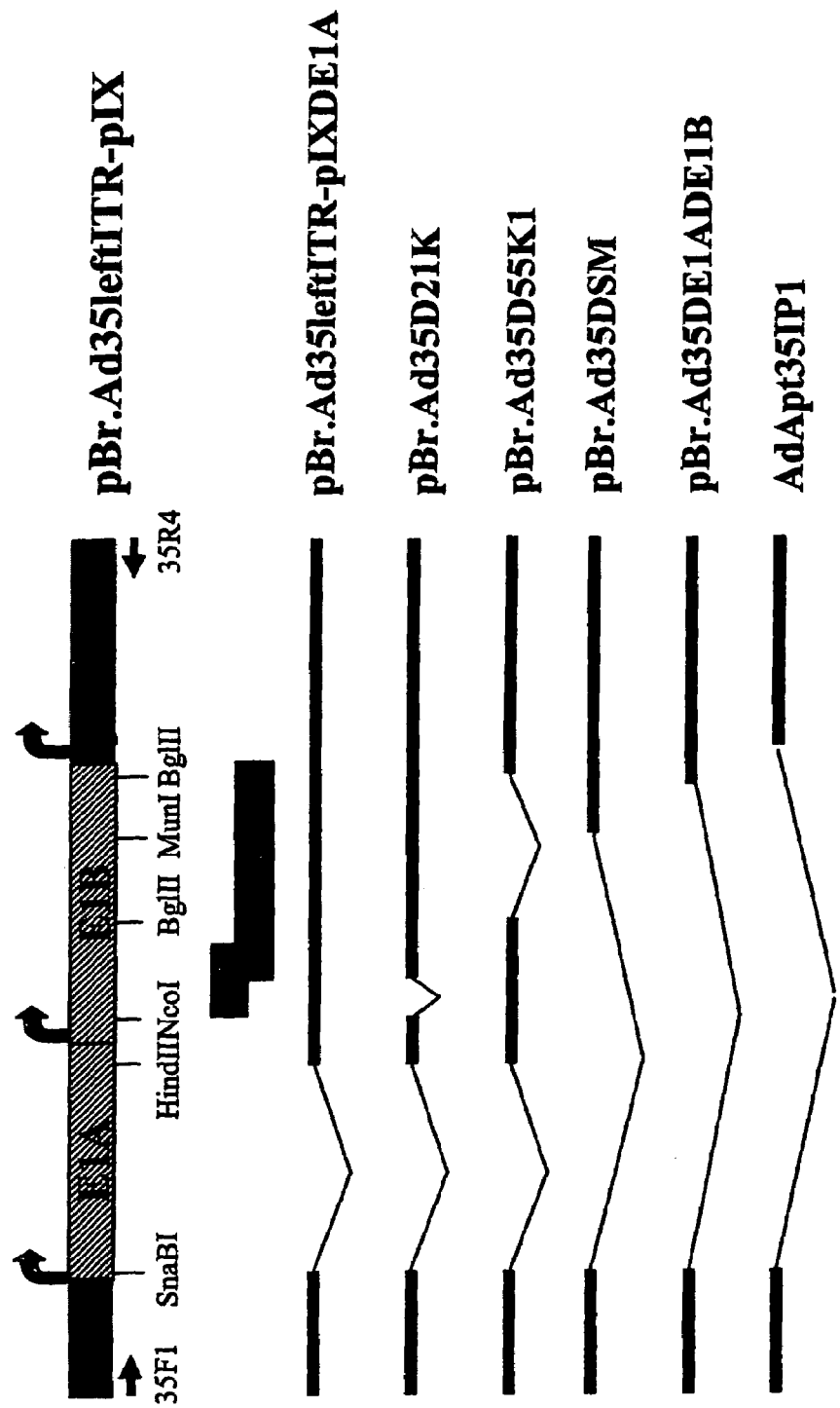
FIG. 20: Schematic representation of Ad35-E1A/E1B deletion constructs.

A third construct that has a deletion of E1A, 21K and most of the 55K sequences was generated as follows. pBr.Ad35.leftITR-pIX (FIG. 15) was digested with SnaBI and MfeI (isoschizomer of MunI) and the 5' overhang resulting from the MfeI digestion was filled in using Klenow enzyme. The 4.4 kb vector fragment was isolated from gel using the GENECLEAN kit (Bio 101, Inc.) according to the manufacturer's instructions and religated to give construct pBr.Ad35ΔSM (FIG. 19). In this construct, the Ad35 sequences between nucl. 453 and 2804 are deleted. Thus, 596 nucl. of the 3' end of E1b-55K are retained. A further deletion of 55K sequences was made in construct pBr.Ad35ΔE1A.ΔE1B by digestion of pBr.Ad35.leftITR-pIX with SnaBI and BglII, Klenow treatment to fill in the BglII cohesive ends, and religation. FIG. 20 shows a schematic representation of the above-mentioned constructs.

To test whether Ad35-based viruses can be generated with these constructs, each of the constructs was cotransfected with NotI digested pWE.Ad35pIX-rITR (see Example 4) onto PER.C6 cells. Hereto, the respective fragments were PCR amplified using primers 35F1 and 35R4 (see, Example 4). This PCR amplification was done since some of the constructs were difficult to isolate in large enough quantities. In this way, equal quality of the different adapter fragments was ensured. For the amplification, Pwo DNA polymerase (Roche) was used according to the manufacturer's instructions but with DMSO (3% final concentration) added to the PCR mixture. Of each template ~50 ng DNA was used. The conditions for the PCR were as follows: 94° C. for 2', then 5 cycles of 94° C. for 30", 48° C. for 45" and 72° C. for 4' followed by 25 cycles of 94° C. for 30", 60° C. for 30" and 72° C. for 4' and a final step at 68° C. for 8'. PCR fragments were generated from pBr.Ad35leftITR-pIX, pBr.Ad35.leftITR-pIXΔE1A, pBr.Ad35Δ21K, pBr.Ad35Δ55K1, pBr.Ad35ΔSM and pBr.Ad35ΔE1AΔE1B. All fragments were using the PCR purification kit (Qiagen) according to manufacturer's instructions and final concentrations were estimated on EtBr stained agarose gel using the Eagle Eye II Still Video system and EagleSight software (Stratagene) with the SmartLadder molecular weight marker (Eurogentec) as reference.

PER.C6 cells were seeded at a density of 2.5×10⁶ cells in a T25 culturing flask in DMEM containing 10% fetal calf serum (FCS) and 10 mM MgSO$_4$ and cultured in a humidified stove at 37° C., 10% CO$_2$. The next day, 3 mg of each of the PCR fragments was cotransfected with 5 μgr NotI digested pWE.Ad35pIX-rITR using LipofectAmine (GIBCO, Life Technologies Inc.) according to the manufacturer's instructions. Two days after the transfection, all cells were passed to a T80 flask and further cultured. Cultures were then monitored for the appearance of CPE. In line with the outcome of previous experiments described in Examples 4 and 6, pBr.Ad35.leftITR-pIX and pBr.Ad35.leftITR-pIXΔE1A showed almost full CPE within one week following transfection. Of the fragments with different E1B deletions, only pBr.Ad35Δ21K showed CPE at the same time as the above two fragments. Constructs pBr.Ad35Δ55K1, pBr.Ad35ΔSM and pBr.Ad35ΔE1AΔE1 B did not give CPE at all, not even after harvesting by freeze-thawing and re-infection of the crude lysate onto fresh PER.C6 cells.

From these experiments, it can be concluded that Ad35-E1B-55K, and not E1B-21K, is necessary for generation and propagation of Ad35-based viruses on Ad5 complementing cell lines. Therefore, Ad35-based viruses having a deletion of the E1A and E1B-21K genes and having the E1B-55K gene, or a functional fragment thereof, can be grown on Ad5 complementing cell lines. Alternatively, Ad35-based viruses can be grown on PER.C6 cells that stably express the full E1B region or the E1B-55K gene, or a functional fragment thereof. The Ad35-E1B-55K gene, or functional parts thereof, may be expressed from a heterologous promoter like, but not limited to, the human PGK promoter, the human cytomegalovirus immediate early promoter (CMV), Rous sarcoma virus promoter, etc., and terminated by a heterologous poly adenylation sequence (pA) like, but not limited to, the hepatitis B virus poly adenylation sequence (HBVpA) and the Simian Virus 40 poly adenylation sequence (SV40pA), etc. As nonlimiting examples, PER.C6 cells that express the Ad35-E1B region driven by the E1B promoter and HBVpA, PER.C6 cells that express the Ad35-E1B region driven by the human PGK promoter and HBVpA and PER.C6 cells that express a functional fragment of Ad35-E1B-55K driven by the human PGK promoter and HBVpA are described below.

Generation of pIG35BL and pIG35BS

Figure 21:
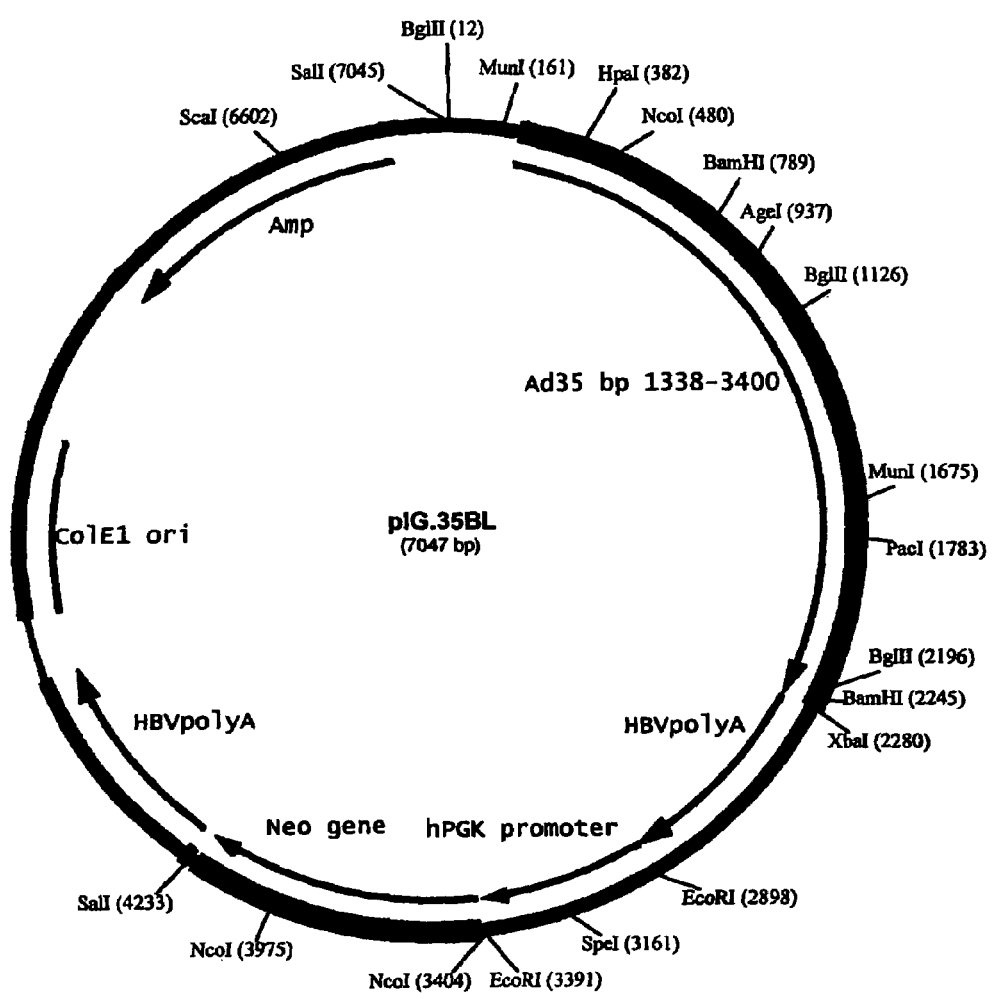
FIG. 21: Map of pIG.35BL.

We describe the generation of two expression constructs, pIG.35BS and pIG.35BL, that both carry the Ad35-E1B genes and a neomycin selection marker. The two constructs differ in the length of the fragment containing the E1B promoter. In 35BL, the promoter fragment is longer and includes the 3' end of the E1A region (103 nucl. coding sequence and pA). The E1B region is terminated by the HBVpolyA and the neo$^r$ gene is driven by a hPGK promoter/HBVpA cassette.

pIG.35BL was made as follows. Construct pRSV.Ad35E1 (described in Example 5, FIG. 8) was digested with NruI and HindIII and the protruding ends were filled in by Klenow treatment. The 7 kb vector fragment was separated from the smaller fragment on gel and isolated using the GENECLEAN kit (BIO 101, Inc.). After religation of the DNA and transformation into competent STBL2 cells (Gibco, LTI), correct clones were isolated. pIG.35BL (FIG. 21) contains 273 nucl. upstream of the start site of the E1B-21K coding region.

pIG.35BS was made in the same way as pIG.35BL except that pRSV.Ad35E1 was digested with NruI and HpaI (both enzymes leave blunt ends), resulting in a shorter fragment upstream of the coding region of E1B-21K: 97 nucleotides.

To generate Ad35-E1B expressing cells, PER.C6 cells were seeded in 10 cm dishes at 1×10$^6$ cells/dish. Two days later, cells were transfected with ScaI linearized constructs. Four dishes were transfected with 1 and four with 2 μg DNA (total of 16 dishes; Lipofectamine (Gibco, LTI), no carrier DNA used) according to the manufacturer's instructions. The next day, transfected cells received G418-containing medium (0.75 mg/ml). Control transfections using LacZ expression constructs (2 μg) were stained after 48 hrs and showed a transfection efficiency of ~25%. Four days following addition of selection medium, untransfected cells started to die and again, three days later, clones were becoming visible. A week later, the first clones were picked. Transfection with 1 μg resulted in less and also, initially, smaller clones (total ~20 clones/dish against >50 clones/dish for the transfection with 2 μg DNA). The positive control transfection using 2 μg pcDNA3 (Invitrogen) resulted in ~50 clones.

In total, 120 clones were picked and 107 were successfully established (55 from pIG35BS and 52 from pIG35BL).

Figure 22:
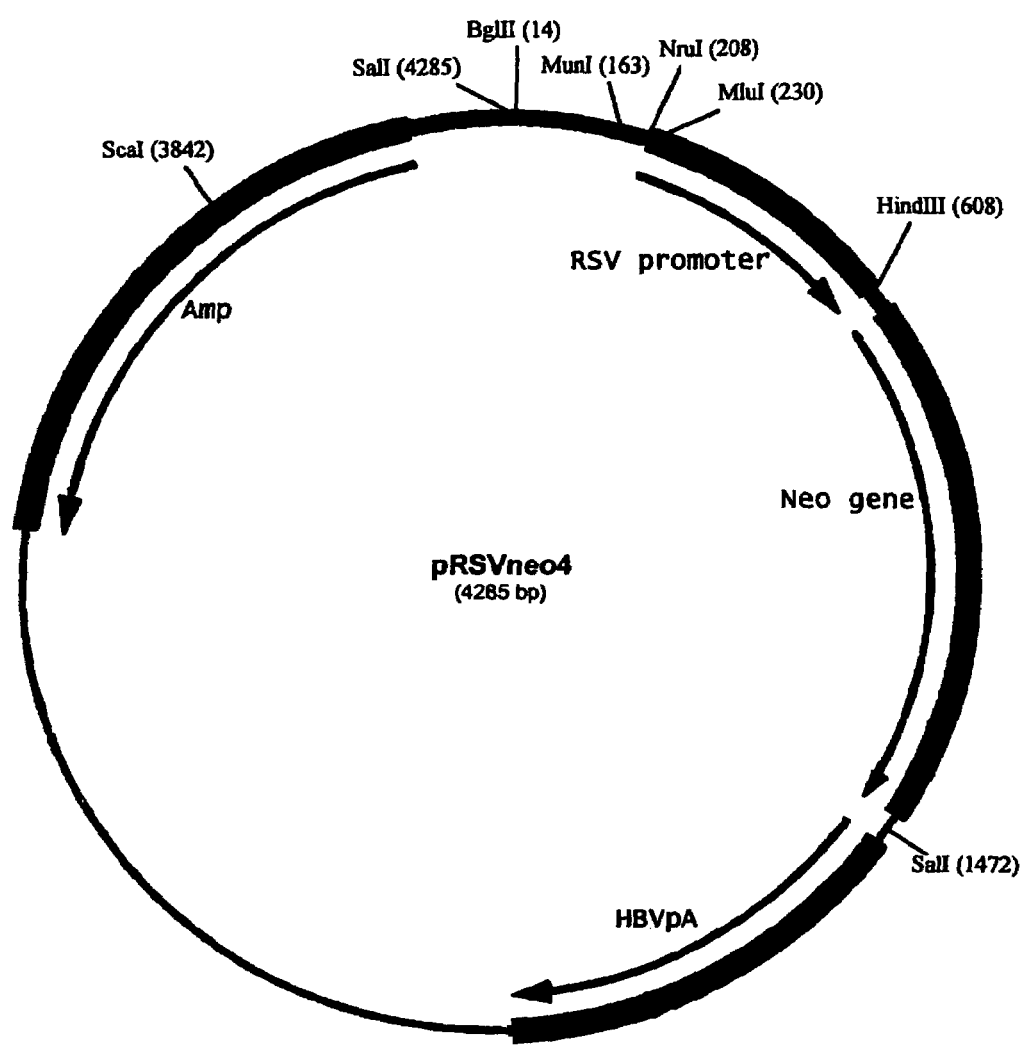
FIG. 22: Map of pRSVneo4.
Figure 23:
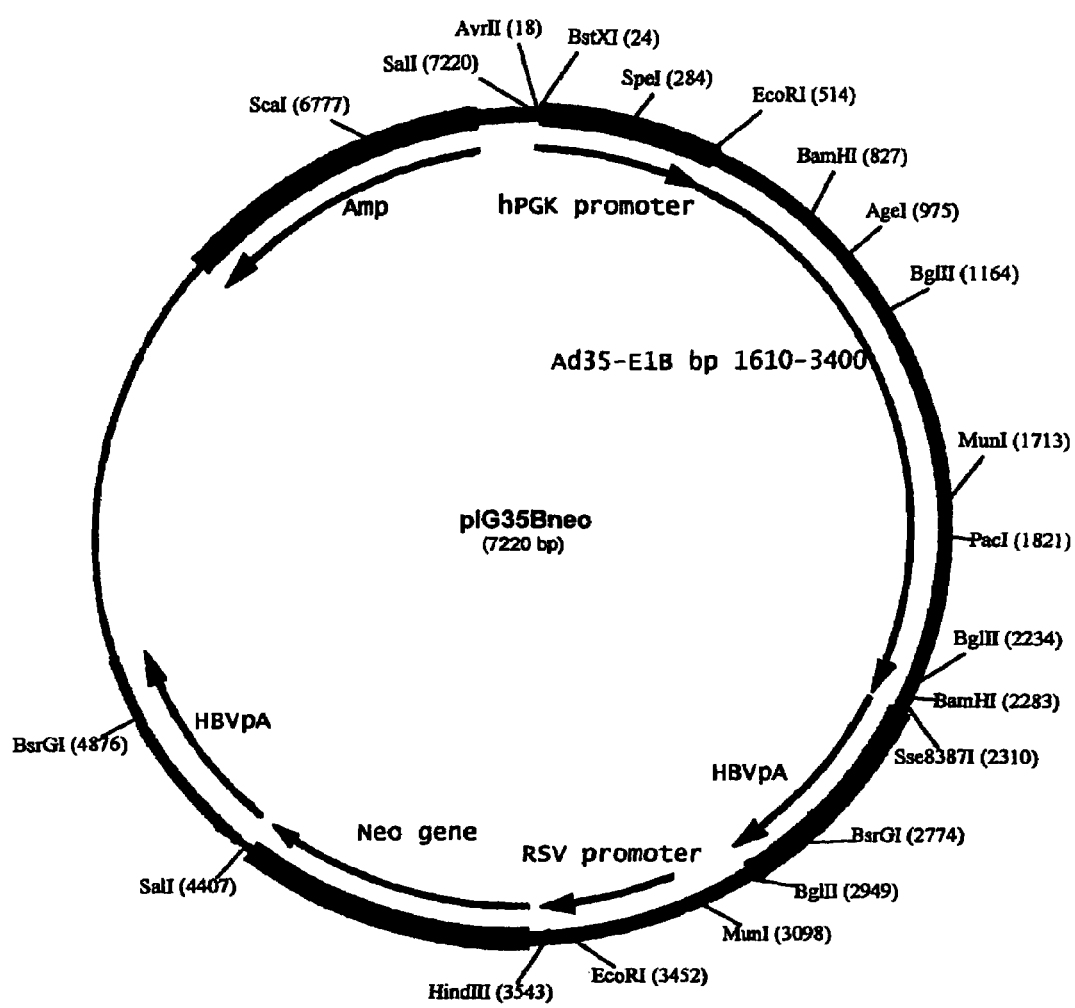
FIG. 23: Map of pIG35Bneo.

Generation of pIG35Bneo pIG35Bneo is an Ad35-E1B expression plasmid from which the E1B genes are expressed from a heterologous promoter (hPGK) and that also contains a neomycin resistance expression cassette. To avoid instability of the plasmid due to recombination events on homologous sequences, the RSV promoter drives the neo$^r$ gene. To achieve this, construct pRSVhbv.Neo (described in Example 5, FIG. 11) was digested with ScaI and BamHI and protruding ends were filled in using Klenow enzyme. The 1070 bp fragment containing part of the Ampicilin gene and the RSV promoter was isolated from gel using the GENECLEAN kit (BIO 101, Inc.). Next, pRSVhbvNeo was digested with ScaI and EcoRI, blunted with Klenow and the 3.2 kb fragment containing the neo gene, HBVpA, vector and part of the Ampicillin gene was isolated as above. The two fragments were then ligated to give pRSVneo4 (FIG. 22). Construct pIG270 (FIG. 14, described in Example 6) was then digested with EcoRI and NcoI and sticky ends were blunted with Klenow enzyme. The vector-containing fragment was isolated from gel as described above and religated to give pIG270ΔE1A. This construct was digested with AvrII and XbaI and protruding ends were filled in using Klenow enzyme. The 2.9 kb fragment containing the hPGK promoter and Ad35-E1B sequences was isolated from gel as above. Next, pRSVneo4 was digested with BglII, blunted with Klenow enzyme, dephosphorylated and isolated from gel. The blunted AvrII/XbaI Ad35-E1B fragment was then ligated with the above prepared pRSVneo4 vector fragment and resulting clones were analyzed. One clone that contained both expression cassettes in the same orientation was chosen and named pIG35Bneo (FIG. 23). Detailed analysis of this clone revealed that an extra BglII site was present, probably due to an incomplete Klenow reaction (BglII site at nucl 2949 in FIG. 23).

Generation of pIG35.55K

Construct pIG35.55K is similar to pIG35Bneo, however, it lacks the coding region of Ad35-E1B-21K. Hereto, both the E1A and E1B-21K sequences are first deleted from pIG270 as follows:

Construct pIG270 is digested with EcoRI, treated with Klenow enzyme and purified using a PCR purification kit (Qiagen) according to the manufacturer's instructions. The recovered DNA is then digested with AgeI and the 5 kb vector fragment was isolated from gel as above. Next, Ad35-E1B-55K sequences are amplified by PCR on pIG270 template DNA using the following primers:

```
35D21: 5'-TTA GAT CCA TGG ATC CCG CAG ACT C-3'   (SEQ ID NO:30)
and

35B3: 5'-CCT CAG CCC CAT TTC CAG-3'.             (SEQ ID NO:31)
```

Figure 24:
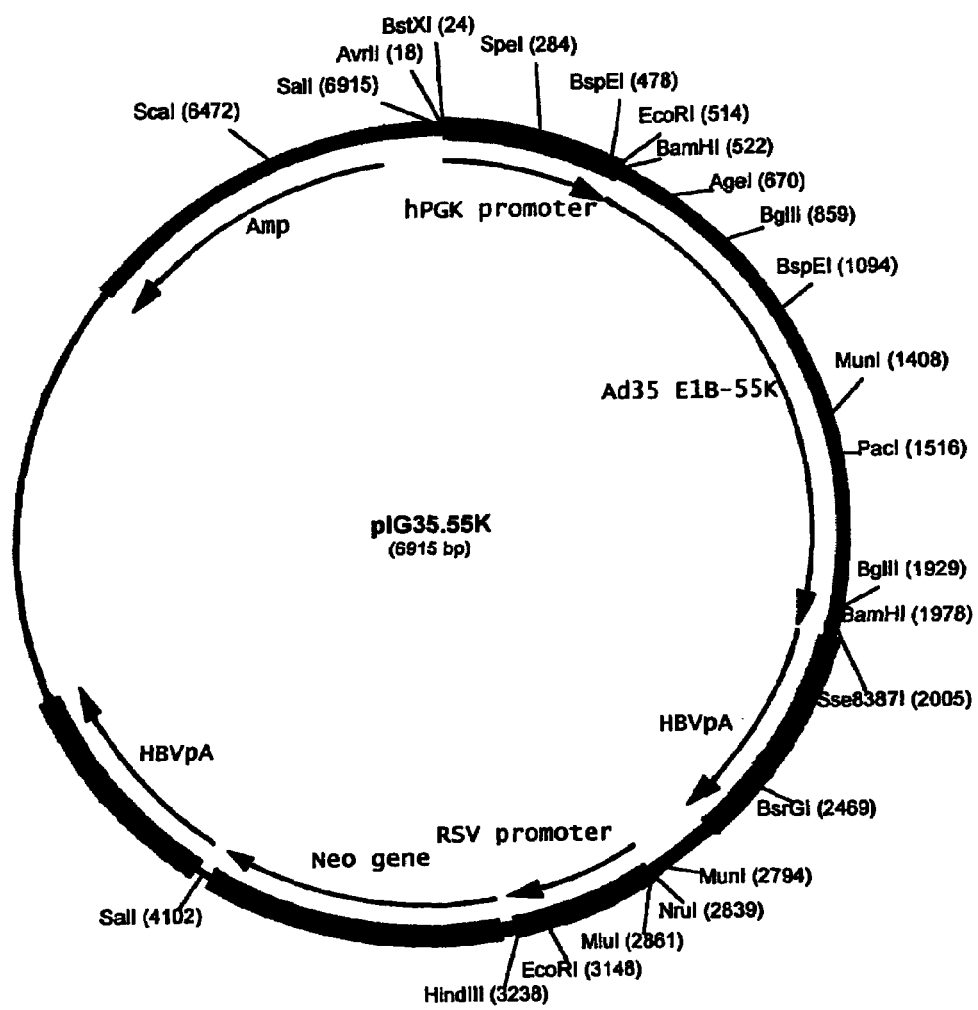
FIG. 24: Map of pIG35.55K.

The conditions used for the amplification are as previously described. The PCR fragment is purified using the PCR purification kit (Qiagen) and digested with NcoI. Following Klenow treatment to fill in the protruding ends, the DNA is further digested with AgeI and again column purified. The thus treated PCR fragment is then cloned into the above prepared EcoRI/AgeI digested vector fragment to give pIG270.ΔE1AΔ21K. The last steps to obtain pIG35.55K (FIG. 24) are equivalent to the last steps described above for the generation of pIG35Bneo, starting with pIG270.ΔE1AΔ21K instead of pIG270.ΔE1A.

pIG35.55K is then linearized with ScaI and used to transfect PER.C6 cells as described above. Clones that are resistant to G418 selection are picked and analyzed for their ability to complement the propagation of E1-deleted Ad35 viruses.

Example 8

New Packaging Cell Lines for the Generation and Propagation of E1-Deleted Ad35-Based Vectors Derived from Primary Human Cells.

The complete morphological transformation of primary cells by adenovirus E1 genes is the result of the combined activities of the proteins encoded by the E1A and E1B regions. The roles of the different E1 proteins in lytic infection and in transformation have been studied extensively (reviewed in Zantema and van der Eb, 1995; White, 1995, 1996). The adenovirus E1A proteins are essential for transformation of primary cells. The E1A proteins exert this effect through direct interaction with a number of cellular proteins that are involved in regulation of transcription. These include the pRB family of proteins, p300/CBP and TATA binding protein. In addition to this, E1A increases the level of p53 protein in the cells. In the absence of adenovirus E1B activity, the rise in p53 levels leads to the induction of apoptosis. Both proteins encoded by the E1B region counteract the induction of apoptosis, although by different mechanisms. E1B-21K seems to counteract apoptosis in a manner similar to Bcl-2 via interaction with the effector proteins downstream in the apoptosis pathway (Han et al., 1996), whereas E1B -55K functions through direct interaction with p53. Importantly, the molecular mechanism by which the E1B-55K proteins of Ad2 and 5 (subgroup C) and Ad12 (subgroup A) function in the ability to neutralize p53 may differ. Whereas Ad5 E1B-55K binds p53 strongly and the complex localizes to the cytoplasm, Ad12-E1B-55K binds p53 weakly and both proteins are localized in the nucleus (Zantema et al., 1985; Grand et al., 1999). Both proteins, however, inhibit the transactivation of other genes by p53 (Yew and Berk, 1992).

In rodent cells, the activity of E1A, together with either E1B-21K or 55K, is sufficient for full transformation, although expression of both E1B proteins together is twice as efficient (Rao et al., 1992;). In human cells, however, the activity of the E1B-55K protein seems to be more important, given the observation that E1B-55K is indispensable for the establishment of transformed cells (Gallimore, 1986).

Example 6 hereof describes the generation of pIG270. In this construct, the Ad35-E1 genes are expressed from the hPGK promoter and transcription is terminated by the HBVpA. The hPGK promoter constitutes a HincII-EcoRI fragment of the promoter sequence described by Singer-Sam et al. (1984). The HBVpA is located in a BamHI-BglII fragment of the Hepatitis B virus genome (Simonsen and Levinson, 1983; see also Genbank HBV-AF090841). As mentioned before, the promoter and polyadenylation sequences of the E1 expression constructs described in this invention may be derived from other sources without departing from the invention. Also, other functional fragments of the hPGK and HBVpA sequences mentioned above may be used.

The functionality of pIG270 was shown by transformation of primary Baby Rat Kidney cells (BRK). Comparison with an equivalent Ad5-E1 expression construct learned that Ad35-E1 genes were less efficient in transforming these cells. The same has been found for the E1 genes of Ad12 (Bernards et al., 1982).

It is unclear which E1 protein(s) determine(s) the difference in transformation efficiency of E1 sequences observed for adenoviruses from different subgroups. In the case of Ad12, transfection studies with chimeric E1A/E1B genes suggested that the efficiency of transformation of BRK cells was determined by the E1A proteins (Bernards et al., 1982). The E1B-55K protein is shown infra to contain serotype-specific functions necessary for complementation of E1-deleted adenoviruses. If these functions are related to the regulation of mRNA distribution or another late viral function, it is unlikely that these are involved in the transformation efficiency.

Analysis of functional domains in the Ad2 or Ad5-E1B-55K proteins using insertion mutants have revealed that functions related to viral replication, late protein synthesis and host protein shut-off are not confined to specific domains but are distributed along the protein (Yew et al., 1990). Using the same set of mutants, the domains important for interaction with p53 and E4-Orf6 were found to be more restricted. In addition to one common binding region (amino acids 262 to 326), p53 binding was affected by mutations at aa 180 and E4-Orf6 binding was affected by mutations at aa 143 (Yew and Berk, 1992; Rubenwolf et al., 1997).

Altogether, these results indicate that it is difficult to separate the E1B-55K functions related to transformation (p53 binding) and late protein synthesis (Orf6 binding).

Here is described new E1 constructs that combine the high efficiency of transformation of one serotype with the serotype-specific complementation function of another serotype. These new constructs are used to transform primary human embryonic retinoblast cells and human amniocytes.

The Generation of pIG535, pIG635 and pIG735

Construct pIG535 contains the Ad5-E1A region and E1B promoter sequences linked to the Ad35-E1B sequences. Hereto, pIG270 (FIG. 14; see example 6) was digested with EcoRI and NcoI. The 5.3 kb vector fragment was then isolated from gel using the GENECLEAN kit (BIO Inc. 101) according to the instructions of the manufacturer. Next, construct pIG.E1A.E1B (FIG. 12; see example 6) was digested with EcoRI and XbaI and the resulting 890 bp fragment was isolated as above. A third fragment was generated by PCR amplification on pIG.E1A.E1B using the following primers:

```
5E1A-F: 5'-GAG ACG CCC GAC ATC ACC TG-3'         (SEQ ID NO:32)
and

5E1B-R: 5'-CAA GCC TCC ATG GGG TCA GAT GTA AC-3'. (SEQ ID NO:33)
```

The following PCR program was used: 94° C. for 2' followed by 30 cycles of 94° C. for 30", 60° C. for 30" and 72° C. for 1', and a final step at 72° C. for 10' to ensure blunt ends.

Figure 25:
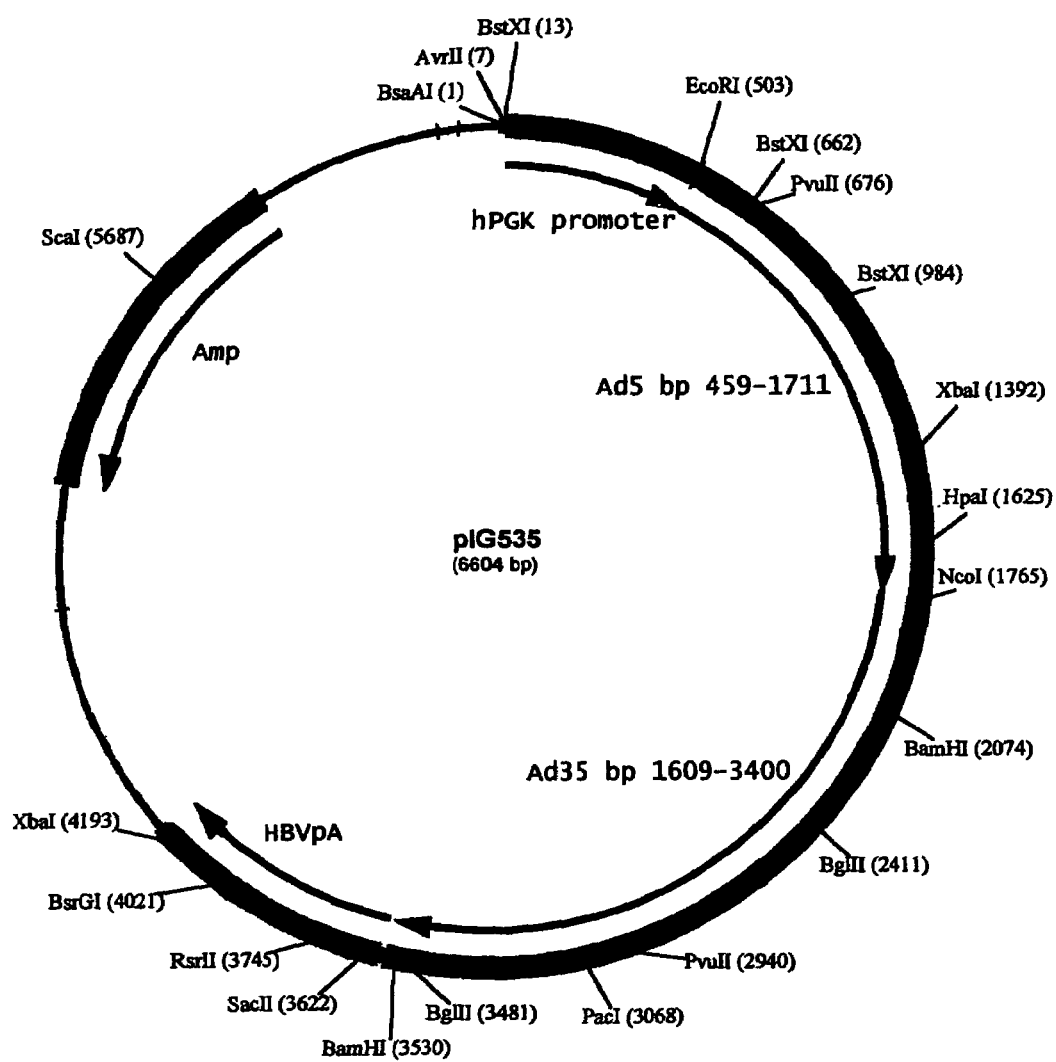
FIG. 25: Map of pIG535.

The resulting 400 bp PCR fragment was digested with XbaI and NcoI. After gel isolation as above, the three fragments were ligated and transformed into STBL-2 bacteria. One colony containing all three fragments in the correct order was selected and designated pIG535 (FIG. 25).

Construct pIG635 contains the Ad5-E1A and a chimeric Ad5-Ad35-E1B region such that the 21K sequence is essentially from Ad5 and linked to the Ad35-E1B-55K sequences as far as not overlapping with the 21K sequences. First, part of the Ad5-E1 sequences are amplified by PCR using pIG.E1A.E1B as template and the following primers:

(SEQ ID NO:34)
5AK: 5'-GAG CGA AGA AAC CCA TCT GAG-3' and (SEQ ID NO:35)
2155R: 5'-GGT CCA GGC CGG CTC TCG G-3'.

Amplification is accomplished with Pwo DNA polymerase (Roche) according to manufacturer's instructions. The 210 bp fragments is then purified from the primer sequences using the PCR purification kit (Qiagen).

A second PCR fragment is amplified from pIG270 DNA as described above but with the following primers:

(SEQ ID NO:36)
2155F: 5'-CCG AGA GCC GGC CTG GAC-3' and (SEQ ID NO:37)
35F10: 5'-GCT CTA GAC CTG CAG GTT AGT CAG TTT CTT CTC CAC TG-3'.

Figure 26:
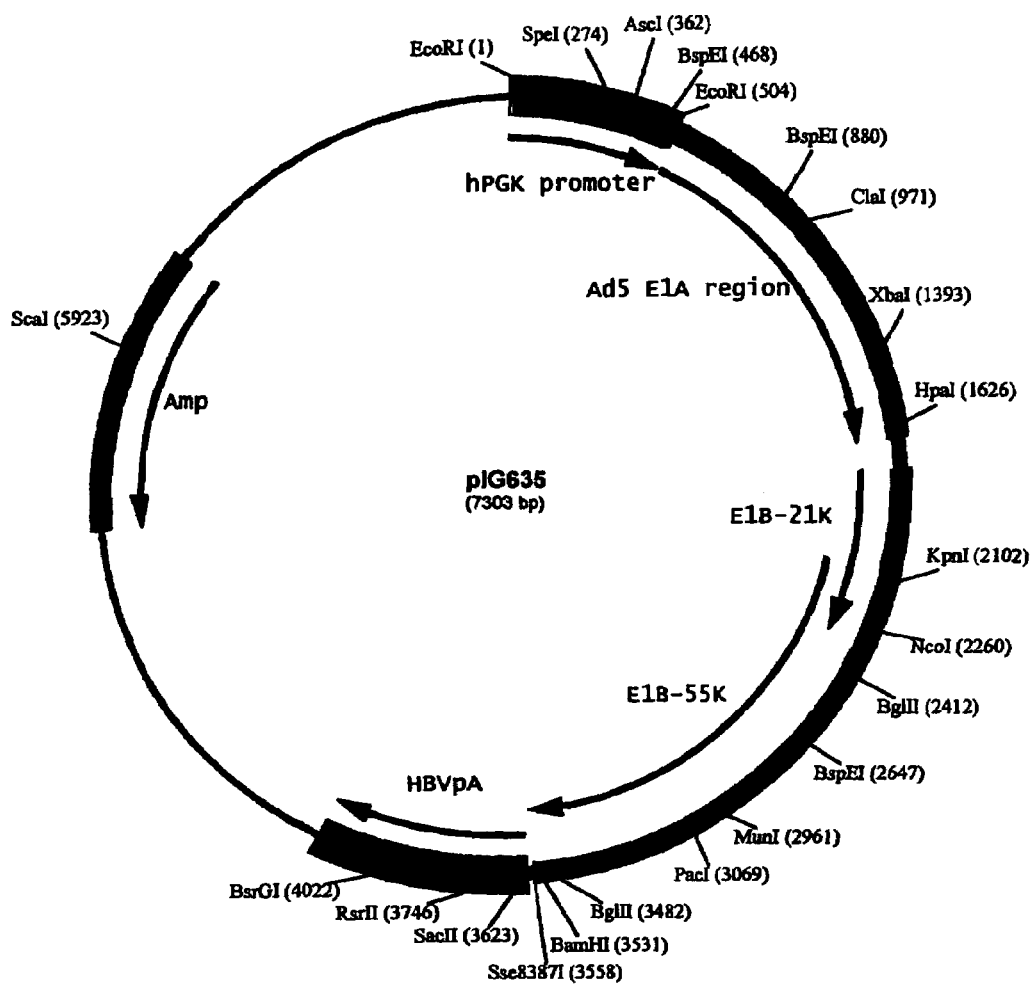
FIG. 26: Map of pIG635.

The 1.3 kb amplified fragment is purified as above and mixed in a 1:1 molar ratio with the first PCR fragment. The mixture is then first subjected to a PCR reaction without the addition of primers using Pwo DNA polymerase and the following program: 94° C. for 2' and then 5 cycles of 94° C. for 30", 60° C. for 30", 72° C. for 90". Subsequently, primers 5AK and 35F10 are added at 0.6 µM concentration after which a last PCR amplifies a 1.5 kb fragment. Hereto, temperature was set as follows: 94° C. for 2', then 30 cycles of 94° C. for 30", 60° C. for 30" and 72° C. for 90", followed by a final step at 72° C. for 10' to ensure blunt ends. The resulting product is purified using the PCR purification kit (Qiagen) as above and digested with KpnI and SbfI (isoschizomer of Sse83871). The digested DNA is then isolated from gel using the GENECLEAN kit (BIO Inc., 101). Construct pIG.E1A.E1B is digested with KpnI and SbfI and the vector-containing fragment is isolated from gel as above. This fragment is ligated to the above prepared final PCR product and the ligation mixture is transformed into STBL-2 cells (Gibco, LTI) according to manufacturer's instructions. This gives construct pIG635 (FIG. 26).

In construct pIG735, the border between Ad5 derived sequences and Ad35 derived sequences is located more 3' than in construct pIG635. First, a BspEI site is introduced in the Ad5 sequence of construct pIG.E1A.E1B without changing the amino acid sequence. Hereto, Ad5 sequences from pIG.E1A.E1B are amplified using the following PCR primers: 5AK: (SEQ ID NO:34) see above, and Bsp-R: 5'-GCT CTA GAC CTG CAG GGT AGC AAC AAT TCC GGA TAT TTA CAA G-3' (SEQ ID NO:38).

Amplification is accomplished using Pwo DNA polymerase (Roche) according to the manufacturer's instruction. The following PCR program is used: 94° C. for 2' followed by 30 cycles of 94° C. for 30", 60° C. for 30" and 72° C. for 30", and a final step at 72° C. for 10' to ensure blunt ends.

Figure 27:
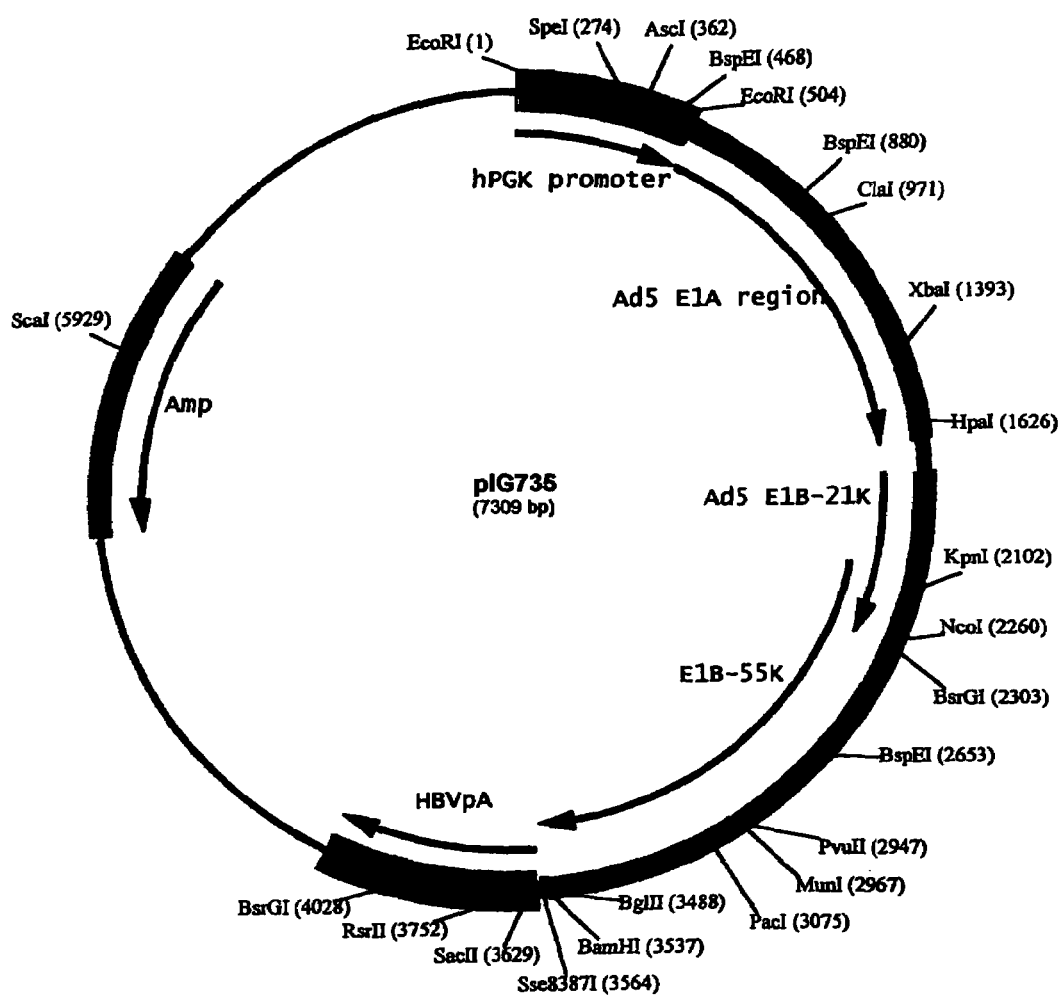
FIG. 27: Map of pIG735.

The resulting 0.6 kb fragment is purified as above and digested with KpnI and SbfI and ligated to the above described KpnI/SbfI digested pIG.E1A.E1 B vector fragment. Selection of colonies after transformation of STBL-2 bacteria (Life Techn. Inc.) gives construct pIG.E1D55K. pIG.E1D55K is then digested with SbfI and partially with BspEI. The 6.4 kb SbfI-partial BspEI digested vector fragment is then isolated from gel using the GENECLEAN kit (BIO 101, Inc.). Next, pIG270 is digested with BspEI and SbfI and the resulting 915 bp fragment is isolated from gel as above. This fragment is then ligated to the above prepared SbfI/partial BspEI digested pIG.E1D55K vector fragment and transformed into STBL-2 competent cells. This gives construct pIG735 (FIG. 27). Clones are analyzed by restriction enzyme digestion and sequencing to ensure correct ligation of the fragments. Constructs pIG535, pIG635 and pIG735 can be used to generate complementing cell lines from primary human cells as described in Example 6.

TABLE I

| Serotype # | Elution [NaCl] mM | VP/ml | CCID50 | $\log_{10}$ VP/CCID50 ratio |
|---|---|---|---|---|
| 1 | 597 | $8.66 \times 10^{10}$ | $5.00 \times 10^{7}$ | 3.2 |
| 2 | 574 | $1.04 \times 10^{12}$ | $3.66 \times 10^{11}$ | 0.4 |
| 3 | 131 | $1.19 \times 10^{11}$ | $1.28 \times 10^{7}$ | 4.0 |
| 4 | 260 | $4.84 \times 10^{11}$ | $2.50 \times 10^{8}$ | 3.3 |
| 5 | 533 | $5.40 \times 10^{11}$ | $1.12 \times 10^{10}$ | 1.7 |
| 6 | 477 | $1.05 \times 10^{12}$ | $2.14 \times 10^{10}$ | 1.7 |
| 7 | 328 | $1.68 \times 10^{12}$ | $2.73 \times 10^{9}$ | 2.4 |
| 9 | 379 | $4.99 \times 10^{11}$ | $3.75 \times 10^{7}$ | 4.1 |
| 10 | 387 | $8.32 \times 10^{12}$ | $1.12 \times 10^{9}$ | 3.9 |
| 12 | 305 | $3.64 \times 10^{11}$ | $1.46 \times 10^{7}$ | 4.4 |
| 13 | 231 | $4.37 \times 10^{12}$ | $7.31 \times 10^{8}$ | 3.8 |
| 15 | 443 | $5.33 \times 10^{12}$ | $1.25 \times 10^{9}$ | 3.6 |
| 16 | 312 | $1.75 \times 10^{12}$ | $5.59 \times 10^{8}$ | 3.5 |
| 17 | 478 | $1.39 \times 10^{12}$ | $1.45 \times 10^{9}$ | 3.0 |
| 19 | 430 | $8.44 \times 10^{11}$ | $8.55 \times 10^{7}$ | 4.0 |
| 20 | 156 | $1.41 \times 10^{11}$ | $1.68 \times 10^{7}$ | 3.9 |
| 21 | 437 | $3.21 \times 10^{11}$ | $1.12 \times 10^{8}$ | 3.5 |
| 22 | 365 | $1.43 \times 10^{12}$ | $5.59 \times 10^{7}$ | 3.4 |
| 23 | 132 | $2.33 \times 10^{11}$ | $1.57 \times 10^{7}$ | 4.2 |
| 24 | 405 | $5.12 \times 10^{12}$ | $4.27 \times 10^{8}$ | 4.1 |
| 25 | 405 | $7.24 \times 10^{11}$ | $5.59 \times 10^{7}$ | 4.1 |
| 26 | 356 | $1.13 \times 10^{12}$ | $1.12 \times 10^{8}$ | 4.0 |
| 27 | 342 | $2.00 \times 10^{12}$ | $1.28 \times 10^{8}$ | 4.2 |
| 28 | 347 | $2.77 \times 10^{12}$ | $5.00 \times 10^{7}$ | 4.7 |
| 29 | 386 | $2.78 \times 10^{11}$ | $2.00 \times 10^{7}$ | 4.1 |
| 30 | 409 | $1.33 \times 10^{12}$ | $5.59 \times 10^{8}$ | 3.4 |
| 31 | 303 | $8.48 \times 10^{10}$ | $2.19 \times 10^{7}$ | 3.6 |
| 33 | 302 | $1.02 \times 10^{12}$ | $1.12 \times 10^{7}$ | 5.0 |
| 34 | 425 | $1.08 \times 10^{12}$ | $1.63 \times 10^{11}$ | 0.8 |
| 35 | 446 | $3.26 \times 10^{12}$ | $1.25 \times 10^{11}$ | 1.4 |
| 36 | 325 | $9.26 \times 10^{12}$ | $3.62 \times 10^{9}$ | 3.4 |
| 37 | 257 | $5.86 \times 10^{12}$ | $2.8 \times 10^{9}$ | 3.3 |
| 38 | 337 | $3.61 \times 10^{12}$ | $5.59 \times 10^{7}$ | 4.8 |
| 39 | 241 | $3.34 \times 10^{11}$ | $1.17 \times 10^{7}$ | 4.5 |
| 42 | 370 | $1.95 \times 10^{12}$ | $1.12 \times 10^{8}$ | 4.2 |
| 43 | 284 | $2.42 \times 10^{12}$ | $1.81 \times 10^{8}$ | 4.1 |
| 44 | 295 | $8.45 \times 10^{11}$ | $2.00 \times 10^{7}$ | 4.6 |
| 45 | 283 | $5.20 \times 10^{11}$ | $2.99 \times 10^{7}$ | 4.2 |
| 46 | 282 | $9.73 \times 10^{12}$ | $2.50 \times 10^{8}$ | 4.6 |
| 47 | 271 | $5.69 \times 10^{11}$ | $3.42 \times 10^{7}$ | 4.2 |
| 48 | 264 | $1.68 \times 10^{12}$ | $9.56 \times 10^{8}$ | 3.3 |
| 49 | 332 | $2.20 \times 10^{12}$ | $8.55 \times 10^{7}$ | 4.4 |
| 50 | 459 | $7.38 \times 10^{12}$ | $2.80 \times 10^{9}$ | 3.4 |
| 51 | 450 | $8.41 \times 10^{11}$ | $1.88 \times 10^{8}$ | 3.7 |

Legend to Table I:

All human adenoviruses used in the neutralization experiments were produced on PER.C6 cells (Fallaux et al., 1998) and purified on CsCl as described in example 1. The NaCl concentration at which the different serotypes eluted from the HPLC column is shown. Virus particles/ml (VP/ml) were calculated from an Ad5 standard. The titer in the experiment (CCID50) was determined on PER.C6 cells as described in Example 1 by titrations performed in parallel with the neutralization experiment. The CCID50 is shown for the 44 viruses used in this study and reflects the dilution of the virus needed to obtain CPE in 50% of the wells after 5 days. The ratio of VP/CCID50 is depicted in $\log_{10}$ and is a measurement of the infectivity of the different batches on PER.C6 cells.

TABLE II

AdApt35.LacZ viruses escape neutralization by human serum.

| Virus | Human serum dilution | | | | | |
|---|---|---|---|---|---|---|
| | no serum | 10x | 50x | 250x | 1250x | 6250x |
| AdApt5.LacZ moi: 5 VP/cell | 100% | 0% | 0% | 1% | 40% | 80% |
| AdApt35.LacZ 250 µl crude lysate | 100% | 100% | 100% | 100% | 100% | 100% |

TABLE III

The numbers of foci obtained with the different E1 expression constructs in BRK transformation experiments.
Average # of foci/dish:

| | Construct | 1 µgr | 5 µgr |
|---|---|---|---|
| Experiment 1 | pIG.E1A.E1B | nd | 60 |
| | pIG.E1A.E1B | nd | 35 |
| | pRSVAd35E1 | 0 | 3 |
| | pIG.Ad35.E1 | 3 | 7 |
| Experiment 2 | pIG.E1A.E1B | 37 | nd |
| | pIG.Ad35.E1 | nd | 2 |
| Experiment 3 | pIG.E1A.E1B | nd | 140 |
| | pIG.Ad35.E1 | nd | 20 |
| | pIG270 | nd | 30 |

REFERENCES

Abrahamsen, K., Kong, H-L., Mastrangeli, A., Brough, D., Lizonova, A., Crystal, R. G. and Falck-Pedersen, E. (1997). Construction of an adenovirus type 7a E1A⁻ vector. J. Virol. 71, 11, p8946-8951.

Babiss, L. E. and Ginsberg, H. S. (1984). Adenovirus type 5 early region 1b gene product is required for efficient shutoff of host protein synthesis. J. Virol. 50, p202-2122.

Babiss, L. E., Ginsberg, H. S. and Darnell, J. J. (1985). Adenovirus E1B proteins are required for accumulation of late viral mRNA and for effects on cellular mRNA translation and transport. Mol. Cell. Biol. 5, p2552-2558.

Bernards, R., Houweling, A. Schrier, P. I., Bos, J. L. and van der Eb, A. J. (1982). Characterization of cells transformed by Ad5/Ad12 hybrid early region 1 plasmids. Virology 120, p422-432.

Bos, J. L., Polder, L. J., Bernards, R., Schrier, P., van den Elsen, P. J., van der Eb, A. J. and van Ormondt, H. (1981). The 2.2 kb mRNA of the E1B region of human adenovirus type 12 and 5 directs the synthesis of two major tumor antigens from different AUG triplets. Cell 12, p721-732.

Bridge, E. and Ketner, G. (1990). Interaction of adenoviral E4 and E1b products in late gene expression. Virology 174, p345-353.

Bridge, E., Medghalchi, S., Ubol, S., Leesong, M. and Ketner, G. (1993). Adenovirus early region 4 and viral DNA synthesis. Virology 193, p794-801.

Brough, D. E., Lizonova, A., Hsu, C., Kulesa, V. A. and Kovesdi, I. (1996). A gene transfer vector-cell line system for complete functional complementation of adenovirus early regions 1 and 4. J. Virol. 70, p6497-6501.

Fallaux, F. J., Kranenburg, O., Cramer, S. J., Houweling, A., van Ormondt, H., Hoeben, R. C. and van der Eb, A. J. (1996). Characterization of 911: a new helper cell line for the titration and propagation of early region 1-deleted adenoviral vectors. Hum. Gene Ther. 7 (2), p215-222.

Fallaux, F. J., Bout, A., van der Velde, I., van den Wollenberg, D. J., Hehir, K. M., Keegan, J., Auger, C., Cramer, S. J., van Ormondt, H., van der Eb, A. J., Valerio, D. and Hoeben, R. C. (1998). New helper cells and matched early region 1-deleted adenovirus vectors prevent generation of replication competent adenoviruses. Hum. Gene Ther. 9, 1909-1917.

Gallimore, P. H., Grand, R. J. A. and Byrd, P. J. (1986). Transformation of human embryo retinoblasts with simian virus 40, adenovirus and ras oncogenes. AntiCancer Res. 6, p499-508.

Gossen, M., and H. Bujard (1992). Tight control of gene expression in mammalian cells by tetracycline-responsive promoters. Proc. Natl. Acad. Sci. USA 89; 5547-5551.

Graham, F. O., Smiley, J., Russell, W. and Nairn, R. (19770. Characteristics of a human cell line transformed by DNA from human adenovirus type 5. J. Gen. Virol. 36, p59-72.

Grand, R. J. A., Parkhill, J., Szestak, T., Rookes, S. M., Roberts, S. and Gallimore, P. H. (1999). Definition of a major p53 binding site on Ad2-E1B-58K protein and a possible nuclear localization signal on the Ad12-E1B-54K protein. Oncogene 18, p955-965.

Han, J., Sabbatini, P., Perez, D., Rao, L., Modha, D. and White, E. (1996). The E1B-19K protein blocks apoptosis by interacting with and inhibiting the p53-inducible and death-promoting Bax protein. Genes Dev. 10 (4), p461-477.

Jochemsen, A. G., Peltenburg L. T., te Pas, M. F., de Wit, C. M., Bos, J. L. and van der Eb, A. J. (1987). Activation of adenovirus 5 E1A transcription by region E1B in trans-formed primary rat cells. EMBO J. 6 (11), p3399-3405.

Leppard, K. N. and Shenk, T. (1989). The adenovirus E1B-55 kd protein influences mRNA tranport via an intra-nuclear effect on RNA metabolism. EMBO J. 8, p2329-2336.

Pilder, S., Moore, M., Logan, J. and Shenk, T. (1986). The adenovirus E1B-55K transforming polypeptide modulates transport or cytoplasmic stabilization of viral and host cell mRNAs. Mol. Cell. Biol. 6, p470-476.

Rao, L., Debbas, M., Sabbatini, P., Hockenbery, D., Korsmeyer, S. and White, E. (1992). The adenovirus E1A proteins induce apoptosis, which is inhibited by the E1B-19-kDa and Bcl-2 proteins. Proc. Natl. Acad. Sci. USA 89, p7742-7746.

Rubenwolf, S., Schütt, H., Nevels, M., Wolf, H. and Dobner, T. (1997). Structural analysis of the adenovirus type 5 E1B-55-kilodalton-E4orf6 protein complex. J. Virol. 71, p1115-1123.

Simonsen, C. C. and Levinson, A. D. (1983). Analysis of processing and polyadenylation signals of the hepatitis B virus surface antigen gene by using simian virus 40-hepatitis B virus chimeric plasmids. Mol. and Cell. Biol. 3 (12), p2250-2258.

Singer-Sam, J., Keith, D. H., Tani, K., Simmer, R. L., Shively, L., Lindsay, S., Yoshida, A. and Riggs, A. D. (1984). Sequence of the promoter region of the gene for human X-linked 3-phosphoglycerate kinase. Gene 32 (3), p409-417.

White, E. and Cipriani, R. (1990). Role of adenovirus E1B proteins in transformation: Altered organization of intermediate filaments in transformed cells that express the 19-kilodalton protein. Mol. Cell. Biol. 10, p120-130.

White, E. (1995). Regulation of p53-dependent apoptosis by E1A and E1B. In: The molecular repertoire of adenoviruses III. Eds. Doerfler, W. and Böhm, P. Springer-Verlag Berlin Heidelberg 1995, p33-58.

White, E. (1996). Life, death, and the pursuit of apoptosis. Genes Dev. 10 (1), p1-15.

Yew, P. R., Kao, C. C. and Berk, A. J. (1990). Dissection of functional domains in the adenovirus 2 early region 1B-55K polypeptide by suppressor-linker insertional mutagenesis. Virology 179, p795-805.

Yew, P. R. and Berk, A. J. (1992). Inhibition of p53 transactivation required for transformation by adenovirus early region TB protein. Nature 357, p82-85.

Zantema, A., Fransen, J. A., Davis, O. A., Ramackers, F. C., Vooijs, G. P., DeLeys, B. and van der Eb, A. J. (1985). Localization of the E1B proteins of adenovirus 5 in transformed cells, as revealed by interaction with monoclonal antibodies. Virology 142, p44-58.

Zantema, A. and van der Eb, A. J. (1995). Modulation of gene expression by adenovirus transformation. In: The molecular repertoire of adenoviruses III. Eds. Doerfler, W. and Böhm, P.Springer-Verlag Berlin Heidelberg 1995, p1-23.

---

What is claimed is:

1. A packaging cell line capable of generating recombinant replication-competent adenovirus free (RCA-free) adenovirus of subgroup B, said packaging cell line expressing Ad5-E1A or a fragment thereof, and at least an E1B-55K sequence from an adenovirus of subgroup B, wherein said E1B-55K sequence is operably linked to a heterologous promoter.

2. The packaging cell line of claim 1 wherein said E1B-55K sequence is terminated by a heterologous polyadenylation signal.

3. A packaging cell line capable of generating a recombinant replication-competent adenovirus free (RCA-free) adenovirus of subgroup B, said cell line expressing an Ad5-E1A sequence or a fragment thereof, and at least an Ad35-E1B-55K sequence, wherein said cell line comprises transformed primary, diploid human cells selected from the group consisting of primary human retinoblasts, primary human embryonic kidney cells and primary human amniocytes, said primary diploid human cells being transformed by adenovirus E1 sequences either operatively linked on one DNA molecule or located on two separate DNA molecules, said sequences being operatively linked to heterologous regulatory sequences enabling transcription and translation of encoded proteins.

4. A process for producing a packaging cell line capable of generating recombinant replication-competent adenovirus free (RCA-free) subgroup B adenovirus comprising:
  transforming a cell with at least one nucleic acid molecule comprising at least a part of an E1 sequence;
  expressing in said transformed cell an Ad5-E1A sequence or a fragment thereof having Ad5-E1A complementing activity; and
  expressing in said transformed cell at least an Ad35-E1B-55K sequence, wherein expression of said Ad35-E1B-55K sequence is driven by a heterologous regulatory sequence, to produce a cell line capable of generating recombinant adenovirus.

5. The process of claim 4, wherein expression of said Ad35-E1B-55K sequence is terminated by a heterologous poly-adenylation signal.

6. A process of producing a packaging cell line capable of generating recombinant replication-competent adenovirus free (RCA-free) subgroup B adenovirus comprising:
  transforming primary, diploid human cells with an E1A sequence or a fragment thereof having E1A complementing activity and an E1B-55K sequence having E1B-55K complementing activity, wherein the E1B-55K sequence is from an adenovirus of subgroup B, and wherein expression of said E1B-55K sequence is driven by a heterologous promoter;
  enabling transcription of said E1A sequence or fragment thereof and said ELB-55K sequence to produce E1A and E1B-55K transcription products; and
  enabling translation of the E1A transcription product or fragment thereof and said E1B-55K transcription product, thus, producing a packaging cell line.

7. The process of claim 6, wherein the primary, diploid human cells are selected from the group consisting of primary human retinoblasts, primary human embryonic kidney cells and primary human amniocytes.

8. The process of claim 6, wherein said E1A sequence or fragment thereof and the E1B-55K sequence are located on two separate nucleic acid molecules.

9. A process of producing a recombinant replication-competent adenovirus free (RCA-free) subgroup B adenovirus, said process comprising:
  expressing in a cell an E1A sequence or a fragment thereof having E1A complementing activity of a serotype different from said recombinant subgroup B adenovirus, and an E1B-55K sequence from an adenovirus of subgroup B, wherein expression of said E1B-55K sequence is driven by a heterologous promoter;
  introducing a genome sequence of said recombinant subgroup B adenovirus into said cell, wherein said genome sequence lacks a functional E1 sequence;
  allowing replication of said genome sequence;
  allowing expression of proteins encoded by said genome sequence; and
  allowing packaging of the replicated genome sequences to produce a recombinant RCA-free adenovirus.

10. The process of claim 9, further comprising:
  harvesting said produced recombinant adenovirus.

11. The process of claim 9, wherein the recombinant RCA-free adenovirus contains a heterologous nucleic acid sequence of interest.

12. The process of claim 9, wherein said E1A sequence is operably linked to a heterologous poly-adenylation signal and/or a heterologous promoter.

13. A process of producing a recombinant replication-competent adenovirus free (RCA-free) subgroup B adenovirus, said process comprising:
  expressing in a cell an E1A sequence or a fragment thereof having E1A complementing activity, of a serotype different from said recombinant subgroup B adenovirus;
  expressing in said cell an E1B-55K sequence from a serotype of subgroup B, wherein expression of the E1B-55K sequence is driven by a heterologous regulatory sequence;
  introducing a genome sequence of said recombinant RCA-free subgroup B adenovirus into said cell, wherein said genome sequence lacks a functional E1 sequence;
  allowing replication of said genome sequence;
  allowing expression of proteins encoded by said genome sequence; and
  allowing packaging of the replicated genome sequences thus, producing a recombinant RCA-free subgroup B adenovirus.

14. The process of claim 13, wherein said recombinant subgroup B adenovinis is Ad35 or Ad11.

15. The packaging cell line of claim 1, wherein said E1B-55K is of adenovirus serotype 35.

16. The process according to claim 6, wherein said E1B-55K is of adenovirus serotype 35.

17. The process according to claim 9, wherein said E1B-55K is of adenovirus serotype 35.

* * * * *

UNITED STATES PATENT AND TRADEMARK OFFICE
CERTIFICATE OF CORRECTION

PATENT NO. : 7,250,293 B2
APPLICATION NO. : 10/272041
DATED : July 31, 2007
INVENTOR(S) : Ronald Vogels, Menzo Havenga and Majid Mehtali Page 1 of 1

It is certified that error appears in the above-identified patent and that said Letters Patent is hereby corrected as shown below:

On the title page:
In ITEM (56) References Cited,           FOREIGN PATENT DOCUMENTS
    In the "Bai, et al." reference, page 4,           change "After" to --Alter--
    In the "Ball-Goodrich et al." reference, page 5,  change "Murine" to --Minute--
    In the "Lee et al." reference, page 4,           after "constitutive" and before "of" insert --expression--

In the "Stewart et al." reference, page 4,       change "bringing" to --bridging--

In the specification:
    COLUMN 4, LINE 43, starting its own line following "Example 1" insert --A high throughput assay for the detection of neutralizing activity in human serum--
    COLUMN 42, LINE 3, change "TB" to --1B--
    COLUMN 42, LINE 4, change "Ramackers" to --Ramaekers--

In the claims:
CLAIM 6, COLUMN 73, LINE 28, change "ELB" to --E1B--
CLAIM 14, COLUMN 74, LINE 40, change "adenovinis" to --adenovirus--

Signed and Sealed this

Sixteenth Day of December, 2008

JON W. DUDAS
*Director of the United States Patent and Trademark Office*

SEQUENCE LISTING

<160> NUMBER OF SEQ ID NOS: 39

<210> SEQ ID NO 1
<211> LENGTH: 14
<212> TYPE: DNA
<213> ORGANISM: human adenovirus type 35

<400> SEQUENCE: 1
ccaataatat acct                                                        14

<210> SEQ ID NO 2
<211> LENGTH: 21
<212> TYPE: DNA
<213> ORGANISM: human adenovirus type 35

<400> SEQUENCE: 2
aggtatatta ttgatgatgg g                                                21

<210> SEQ ID NO 3
<211> LENGTH: 18
<212> TYPE: DNA
<213> ORGANISM: human adenovirus

<400> SEQUENCE: 3
catcatcaat aaatatacc                                                   18

<210> SEQ ID NO 4
<211> LENGTH: 47
<212> TYPE: DNA
<213> ORGANISM: Artificial Sequence
<220> FEATURE:
<223> OTHER INFORMATION: Linker

<400> SEQUENCE: 4
tcgatggcaa acagctatta tgggtattat gggttcgaat taattaa                    47

<210> SEQ ID NO 5
<211> LENGTH: 47
<212> TYPE: DNA
<213> ORGANISM: Artificial Sequence
<220> FEATURE:
<223> OTHER INFORMATION: Linker

<400> SEQUENCE: 5
tcgattaatt aattcgaacc cataataccc ataatagctg tttgcca                    47

<210> SEQ ID NO 6
<211> LENGTH: 41
<212> TYPE: DNA
<213> ORGANISM: Artificial Sequence
<220> FEATURE:
<223> OTHER INFORMATION: PCR Primer

<400> SEQUENCE: 6
ccccaattgg tcgaccatca tcaataatat accttatttg g                    41

<210> SEQ ID NO 7
<211> LENGTH: 22
<212> TYPE: DNA
<213> ORGANISM: Artificial Sequence
<220> FEATURE:
<223> OTHER INFORMATION: PCR Primer

<400> SEQUENCE: 7
gcgaaaattg tcacttcctg tg                                         22

<210> SEQ ID NO 8
<211> LENGTH: 37
<212> TYPE: DNA
<213> ORGANISM: Artificial Sequence
<220> FEATURE:
<223> OTHER INFORMATION: Linker

<400> SEQUENCE: 8
aattcggcgc gccgtcgacg atatcgatag cggccgc                         37

<210> SEQ ID NO 9
<211> LENGTH: 37
<212> TYPE: DNA
<213> ORGANISM: Artificial Sequence
<220> FEATURE:
<223> OTHER INFORMATION: Linker

<400> SEQUENCE: 9
aattgcggcc gctatcgata tcgtcgacgg cgcgccg                         37

<210> SEQ ID NO 10
<211> LENGTH: 49
<212> TYPE: DNA
<213> ORGANISM: Artificial Sequence
<220> FEATURE:
<223> OTHER INFORMATION: Linker

<400> SEQUENCE: 10
agctctagag gatccgttaa cgctagcgaa ttcaccggta ccaagctta            49

<210> SEQ ID NO 11
<211> LENGTH: 49
<212> TYPE: DNA
<213> ORGANISM: Artificial Sequence
<220> FEATURE:
<223> OTHER INFORMATION: Linker

<400> SEQUENCE: 11
ctagtaagct tggtaccggt gaattcgcta gcgttaacgg atcctctag            49

<210> SEQ ID NO 12
<211> LENGTH: 44
<212> TYPE: DNA
<213> ORGANISM: Artificial Sequence
<220> FEATURE:
<223> OTHER INFORMATION: PCR Primer

```
<400> SEQUENCE: 12
cggaattctt aattaatcga catcatcaat aatataccTt atag          44

<210> SEQ ID NO 13
<211> LENGTH: 33
<212> TYPE: DNA
<213> ORGANISM: Artificial Sequence
<220> FEATURE:
<223> OTHER INFORMATION: PCR Primer

<400> SEQUENCE: 13
ggtggtccta ggctgacacc tacgtaaaaa cag                      33

<210> SEQ ID NO 14
<211> LENGTH: 30
<212> TYPE: DNA
<213> ORGANISM: Artificial Sequence
<220> FEATURE:
<223> OTHER INFORMATION: PCR Primer

<400> SEQUENCE: 14
tggtggagat ctggtgagta ttgggaaaac                          30

<210> SEQ ID NO 15
<211> LENGTH: 37
<212> TYPE: DNA
<213> ORGANISM: Artificial Sequence
<220> FEATURE:
<223> OTHER INFORMATION: PCR Primer

<400> SEQUENCE: 15
cggaattctt aattaaggga aatgcaaatc tgtgagg                  37

<210> SEQ ID NO 16
<211> LENGTH: 34
<212> TYPE: DNA
<213> ORGANISM: Artificial Sequence
<220> FEATURE:
<223> OTHER INFORMATION: PCR Primer

<400> SEQUENCE: 16
cggaattcgc ggccgcggtg agtattggga aaac                     34

<210> SEQ ID NO 17
<211> LENGTH: 21
<212> TYPE: DNA
<213> ORGANISM: Artificial Sequence
<220> FEATURE:
<223> OTHER INFORMATION: PCR Primer

<400> SEQUENCE: 17
cgccagatcg tctacagaac a                                   21

<210> SEQ ID NO 18
<211> LENGTH: 23
<212> TYPE: DNA
<213> ORGANISM: Artificial Sequence
<220> FEATURE:
<223> OTHER INFORMATION: PCR Primer

<400> SEQUENCE: 18
gaatgctggc ttcagttgta atc                                 23

<210> SEQ ID NO 19
<211> LENGTH: 42
```

```
<212> TYPE: DNA
<213> ORGANISM: Artificial Sequence
<220> FEATURE:
<223> OTHER INFORMATION: PCR Primer

<400> SEQUENCE: 19
cggaattcgc ggccgcattt aaatcatcat caataatata cc                    42

<210> SEQ ID NO 20
<211> LENGTH: 33
<212> TYPE: DNA
<213> ORGANISM: Artificial Sequence
<220> FEATURE:
<223> OTHER INFORMATION: PCR Primer

<400> SEQUENCE: 20
ggggtaccga attctcgcta gggtatttat acc                              33

<210> SEQ ID NO 21
<211> LENGTH: 38
<212> TYPE: DNA
<213> ORGANISM: Artificial Sequence
<220> FEATURE:
<223> OTHER INFORMATION: PCr Primer

<400> SEQUENCE: 21
gctctagacc tgcaggttag tcagtttctt ctccactg                         38

<210> SEQ ID NO 22
<211> LENGTH: 27
<212> TYPE: DNA
<213> ORGANISM: Artificial Sequence
<220> FEATURE:
<223> OTHER INFORMATION: PCR Primer

<400> SEQUENCE: 22
ggctctagag atccttcgcg ggacgtc                                     27

<210> SEQ ID NO 23
<211> LENGTH: 26
<212> TYPE: DNA
<213> ORGANISM: Artificial Sequence
<220> FEATURE:
<223> OTHER INFORMATION: PCR Primer

<400> SEQUENCE: 23
ggcgaattca ctgccttcca ccaagc                                      26

<210> SEQ ID NO 24
<211> LENGTH: 17
<212> TYPE: DNA
<213> ORGANISM: Artificial Sequence
<220> FEATURE:
<223> OTHER INFORMATION: Linker

<400> SEQUENCE: 24
gtgcctaggc cacgggg                                                17

<210> SEQ ID NO 25
<211> LENGTH: 13
<212> TYPE: DNA
<213> ORGANISM: Artificial Sequence
<220> FEATURE:
<223> OTHER INFORMATION: Linker

<400> SEQUENCE: 25
```

```
gtggcctagg cac                                                        13

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
cacctctgcc taatcatctc                                                 20

<210> SEQ ID NO 27
<211> LENGTH: 27
<212> TYPE: DNA
<213> ORGANISM: Artificial Sequence
<220> FEATURE:
<223> OTHER INFORMATION: PCR Primer

<400> SEQUENCE: 27
gctctagaaa ttccactgcc ttccacc                                         27

<210> SEQ ID NO 28
<211> LENGTH: 25
<212> TYPE: DNA
<213> ORGANISM: Artificial Sequence
<220> FEATURE:
<223> OTHER INFORMATION: PCR Primer

<400> SEQUENCE: 28
ttagatccat ggatcccgca gactc                                           25

<210> SEQ ID NO 29
<211> LENGTH: 18
<212> TYPE: DNA
<213> ORGANISM: Artificial Sequence
<220> FEATURE:
<223> OTHER INFORMATION: PCR Primer

<400> SEQUENCE: 29
cctcagcccc atttccag                                                   18

<210> SEQ ID NO 30
<211> LENGTH: 25
<212> TYPE: DNA
<213> ORGANISM: Artificial Sequence
<220> FEATURE:
<223> OTHER INFORMATION: PCR Primer

<400> SEQUENCE: 30
ttagatccat ggatcccgca gactc                                           25

<210> SEQ ID NO 31
<211> LENGTH: 18
<212> TYPE: DNA
<213> ORGANISM: Artificial Sequence
<220> FEATURE:
<223> OTHER INFORMATION: PCR Primer

<400> SEQUENCE: 31
cctcagcccc atttccag                                                   18

<210> SEQ ID NO 32
<211> LENGTH: 20
<212> TYPE: DNA
<213> ORGANISM: Artificial Sequence
```

```
<220> FEATURE:
<223> OTHER INFORMATION: PCR Primer

<400> SEQUENCE: 32
gagacgcccg acatcacctg                                                    20

<210> SEQ ID NO 33
<211> LENGTH: 26
<212> TYPE: DNA
<213> ORGANISM: Artificial Sequence
<220> FEATURE:
<223> OTHER INFORMATION: PCr Primer

<400> SEQUENCE: 33
caagcctcca tggggtcaga tgtaac                                             26

<210> SEQ ID NO 34
<211> LENGTH: 21
<212> TYPE: DNA
<213> ORGANISM: Artificial Sequence
<220> FEATURE:
<223> OTHER INFORMATION: PCR Primer

<400> SEQUENCE: 34
gagcgaagaa acccatctga g                                                  21

<210> SEQ ID NO 35
<211> LENGTH: 19
<212> TYPE: DNA
<213> ORGANISM: Artificial Sequence
<220> FEATURE:
<223> OTHER INFORMATION: PCR Primer

<400> SEQUENCE: 35
ggtccaggcc ggctctcgg                                                     19

<210> SEQ ID NO 36
<211> LENGTH: 18
<212> TYPE: DNA
<213> ORGANISM: Artificial Sequence
<220> FEATURE:
<223> OTHER INFORMATION: PCR Primer

<400> SEQUENCE: 36
ccgagagccg gcctggac                                                      18

<210> SEQ ID NO 37
<211> LENGTH: 38
<212> TYPE: DNA
<213> ORGANISM: Artificial Sequence
<220> FEATURE:
<223> OTHER INFORMATION: PCR Primer

<400> SEQUENCE: 37
gctctagacc tgcaggttag tcagtttctt ctccactg                                38

<210> SEQ ID NO 38
<211> LENGTH: 43
<212> TYPE: DNA
<213> ORGANISM: Artificial Sequence
<220> FEATURE:
<223> OTHER INFORMATION: PCR Primer

<400> SEQUENCE: 38
gctctagacc tgcagggtag caacaattcc ggatatttac aag                          43
```

<210> SEQ ID NO 39
<211> LENGTH: 34794
<212> TYPE: DNA
<213> ORGANISM: Human Adenovirus Type 35

<400> SEQUENCE: 39

| | | | | | |
|---|---|---|---|---|---:|
| catcatcaat | aatatacctt | atagatggaa | tggtgccaat | atgtaaatga | ggtgatttta | 60 |
| aaaagtgtgg | gccgtgtggt | gattggctgt | ggggttaacg | gttaaaaggg | gcggcgcggc | 120 |
| cgtgggaaaa | tgacgtttta | tggggtggga | gttttttttgc | aagttgtcgc | gggaaatgtt | 180 |
| acgcataaaa | aggcttcttt | tctcacggaa | ctacttagtt | tcccacggt | atttaacagg | 240 |
| aaatgaggta | gttttgaccg | gatgcaagtg | aaaattgctg | attttcgcgc | gaaaactgaa | 300 |
| tgaggaagtg | ttttctgaa | taatgtggta | tttatggcag | ggtggagtat | ttgttcaggg | 360 |
| ccaggtagac | tttgacccat | tacgtggagg | tttcgattac | cgtgttttt | acctgaattt | 420 |
| ccgcgtaccg | tgtcaaagtc | ttctgttttt | acgtaggtgt | cagctgatcg | ctagggtatt | 480 |
| tatacctcag | ggtttgtgtc | aagaggccac | tcttgagtgc | cagcgagaag | agttttctcc | 540 |
| tctgcgccgg | cagtttaata | ataaaaaaat | gagagatttg | cgatttctgc | ctcaggaaat | 600 |
| aatctctgct | gagactggaa | atgaaatatt | ggagcttgtg | gtgcacgccc | tgatgggaga | 660 |
| cgatccggga | ccacctgtgc | agcttttttga | gcctcctacg | cttcaggaac | tgtatgattt | 720 |
| agaggtagag | ggatcggagg | attctaatga | ggaagctgtg | aatggctttt | ttaccgattc | 780 |
| tatgcttttta | gctgctaatg | aaggattaga | attagatccg | cctttggaca | ctttcaatac | 840 |
| tccagggtg | attgtggaaa | gcggtacagg | tgtaagaaaa | ttacctgatt | tgagttccgt | 900 |
| ggactgtgat | ttgcactgct | atgaagacgg | gtttcctccg | agtgatgagg | aggaccatga | 960 |
| aaaggagcag | tccatgcaga | ctgcagcggg | tgagggagtg | aaggctgcca | atgttggttt | 1020 |
| tcagttggat | tgcccggagc | ttcctggaca | tggctgtaag | tcttgtgaat | tcacaggaa | 1080 |
| aaatactgga | gtaaaggaac | tgttatgttc | gctttgttat | atgagaacgc | actgccactt | 1140 |
| tatttacagt | aagtgtgttt | aagttaaaat | ttaaaggaat | atgctgtttt | tcacatgtat | 1200 |
| attgagtgtg | agttttgtgc | ttcttattat | aggtcctgtg | tctgatgctg | atgaatcacc | 1260 |
| atctcctgat | tctactacct | cacctcctga | tattcaagca | cctgttcctg | tggacgtgcg | 1320 |
| caagcccatt | cctgtgaagc | ttaagcctgg | gaaacgtcca | gcagtggaga | aacttgagga | 1380 |
| cttgttacag | ggtgggggacg | gaccctttgga | cttgagtaca | cggaaacgtc | caagacaata | 1440 |
| agtgttccat | atccgtgttt | acttaaggtg | acgtcaatat | ttgtgtgaga | gtgcaatgta | 1500 |
| ataaaaatat | gttaactgtt | cactggtttt | tattgctttt | tgggcgggga | ctcaggtata | 1560 |
| taagtagaag | cagacctgtg | tggttagctc | ataggagctg | gctttcatcc | atggaggttt | 1620 |
| gggccatttt | ggaagacctt | aggaagacta | ggcaactgtt | agagagcgct | tcggacggag | 1680 |
| tctccggttt | ttggagattc | tggttcgcta | gtgaattagc | tagggtagtt | tttaggataa | 1740 |
| aacaggacta | taaacaagaa | tttgaaaagt | tgttggtaga | ttgcccagga | cttttttgaag | 1800 |
| ctcttaattt | gggccatcag | gttcacttta | aagaaaagt | tttatcagtt | ttagactttt | 1860 |
| caaccccagg | tagaactgct | gctgctgtgg | cttttcttac | ttttatatta | gataaatgga | 1920 |
| tcccgcagac | tcatttcagc | aggggatacg | ttttggattt | catagccaca | gcattgtgga | 1980 |
| gaacatggaa | ggttcgcaag | atgaggacaa | tcttaggtta | ctggccagtg | cagcctttgg | 2040 |
| gtgtagcggg | aatcctgagg | catccaccgg | tcatgccagc | ggttctggag | gaggaacagc | 2100 |
| aagaggacaa | cccgagagcc | ggcctggacc | ctccagtgga | ggaggcggag | tagctgactt | 2160 |

-continued

```
gtctcctgaa ctgcaacggg tgcttactgg atctacgtcc actggacggg ataggggcgt    2220
taagagggag agggcatcca gtggtactga tgctagatct gagttggctt aagtttaat     2280 gagtcgcaga cgtcctgaaa ccatttggtg gcatgaggtt cagaaagagg gaagggatga    2340
agtttctgta ttgcaggaga aatattcact ggaacaggtg aaaacatgtt ggttggagcc    2400
agaggatgat tgggcggtgg ccattaaaaa ttatgccaag atagctttga ggcctgataa    2460
acagtataag atcagtagac ggattaatat ccggaatgct tgttacatat ctggaaatgg    2520
ggctgaggtg gtaatagata ctcaagacaa gacagttatt agatgctgca tgatggatat    2580
gtggcctgga gtagtcggta tggaagcagt cacttttgta aatgttaagt ttaggggaga    2640
tggttataat ggaatagtgt ttatggccaa taccaaactt atattgcatg gttgtagctt    2700
ttttggtttc aacaatacct gtgtagatgc ctggggacag gttagtgtac gggggtgtag    2760
tttctatgcg tgttggattg ccacagctgg cagaaccaag agtcaattgt ctctgaagaa    2820
atgcatattc caaagatgta acctgggcat tctgaatgaa ggcgaagcaa gggtccgtca    2880
ctgcgcttct acagatactg gatgttttat tttaattaag ggaaatgcca gcgtaaagca    2940
taacatgatt tgtggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgttga ccaagtgcac catgcatgca ggtgggcgta gaggaatgtt    3120
tatgccttac cagtgtaaca tgaatcatgt gaaagtgttg ttggaaccag atgccttttc    3180
cagaatgagc ctaacaggaa tctttgacat gaacacgcaa atctggaaga tcctgaggta    3240
tgatgatacg agatcgaggg tgcgcgcatg cgaatgcgga ggcaagcatg ccaggttcca    3300
gccggtgtgt gtagatgtga ccgaagatct cagaccggat catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gacatgagtg gaaatgcttc ttttaagggg ggagtcttca gcccttatct gacagggcgt    3540
ctcccatcct gggcaggagt tcgtcagaat gttatgggat ctactgtgga tggaagaccc    3600
gttcaacccg ccaattcttc aacgctgacc tatgctactt taagttcttc acctttggac    3660
gcagctgcag ccgctgccgc cgcctctgtc gccgctaaca ctgtgcttgg aatgggttac    3720
tatggaagca tcgtggctaa ttccacttcc tctaataacc cttctacact gactcaggac    3780
aagttacttg tccttttggc ccagctggag gctttgaccc aacgtctggg tgaacttttct   3840 cagcaggtgg ccgagttgcg agtacaaact gagtctgctg tcggcacggc aaagtctaaa    3900
taaaaaaaat tccagaatca atgaataaat aaacgagctt gttgttgatt taaaatcaag    3960
tgtttttatt tcattttttcg cgcacggtat gccctggacc accgatctcg atcattgaga    4020
actcggtgga ttttttccag aatcctatag aggtgggatt gaatgtttag atacatgggc    4080
attaggccgt ctttggggtg gagatagctc cattgaaggg attcatgctc cggggtagtg    4140
ttgtaaatca cccagtcata acaaggtcgc agtgcatggt gttgcacaat atcttttaga    4200
agtaggctga ttgccacaga taagcccttg gtgtaggtgt ttacaaaccg gttgagctgg    4260 gagggggtgca ttcgaggtga aattatgtgc attttggatt ggattttaa gttggcaata    4320 ttgccgccaa gatcccgtct tgggttcatg ttatgaagga ctaccaagac ggtgtatccg    4380
gtacatttag gaaatttatc gtgcagcttg atggaaaag cgtggaaaaa tttggagaca    4440
cccttgtgtc ctccgagatt ttccatgcac tcatccatga taatagcaat ggggccgtgg    4500
```

-continued

```
gcagcggcgc gggcaaacac gttccgtggg tctgacacat catagttatg ttcctgagtt    4560
aaatcatcat aagccatttt aatgaatttg gggcggagcg taccagattg gggtatgaat    4620
gttccttcgg gccccggagc atagttcccc tcacagattt gcatttccca agctttcagt    4680
tctgagggtg gaatcatgtc cacctggggg gctatgaaga acaccgtttc ggggcgggg    4740
gtgattagtt gggatgatag caagtttctg agcaattgag atttgccaca tccggtgggg    4800
ccataaataa ttccgattac aggttgcagg tggtagttta gggaacggca actgccgtct    4860
tctcgaagca aggggccac ctcgttcatc atttcccctta catgcatatt ttcccgcacc    4920
aaatccatta ggaggcgctc tcctcctagt gatagaagtt cttgtagtga ggaaaagttt    4980
ttcagcggtt ttagaccgtc agccatgggc attttggaaa agtttgctg caaaagttct    5040
agtctgttcc acagttcagt gatgtgttct atggcatctc gatccagcag acctcctcgt    5100
ttcgcgggtt tggacggctc ctggagtagg gtatgagacg atgggcgtcc agcgctgcca    5160
gggttcggtc cttccaggg tcagtgttc gagtcagggt tgtttccgtc acagtgaagg    5220
ggtgtgcgcc tgcttgggcg cttgccaggg tgcgcttcag actcattctg ctggtggaga    5280
acttctgtcg cttggcgccc tgtatgtcgg ccaagtagca gtttaccatg agttcgtagt    5340
tgagcgcctc ggctgcgtgg cctttggcgc ggagcttacc tttggaagtt tccttgcata    5400
ccgggcagta taggcatttc agcgcataca gcttgggcgc aaggaaaatg gattctgggg    5460
agtatgcatc cgcgccgcag gaggcgcaaa cagtttcaca ttccaccagc caggttaaat    5520
ccggttcatt ggggtcaaaa acaagttttc cgccatattt tttgatgcgt ttcttacctt    5580
tggtctccat aagttcgtgt cctcgttgag tgacaaacag gctgtccgta tctccgtaga    5640
ctgattttac aggcctcttc tccagtggag tgcctcggtc ttcttcgtac aggaactctg    5700
accactctga tacaaaggcg cgcgtccagg ccagcacaaa ggaggctatg tgggagggt    5760
agcgatcgtt gtcaaccagg gggtccacct tttccaaagt atgcaaacac atgtcaccct    5820
cttcaacatc caggaatgtg attggcttgt aggtgtattt cacgtgacct ggggtccccg    5880
ctgggggggt ataaaagggg gcggttcttt gctcttcctc actgtcttcc ggatcgctgt    5940
ccaggaacgt cagctgttgg ggtaggtatt ccctctcgaa ggcgggcatg acctctgcac    6000
tcaggttgtc agtttctaag aacgaggagg atttgatatt gacagtgccg gttgagatgc    6060
cttttcatgag gttttcgtcc atttggtcag aaaacacaat tttttttattg tcaagtttgg    6120
tggcaaatga tccatacagg gcgttggata aagtttggc aatggatcgc atggtttggt    6180
tcttttcctt gtccgcgcgc tctttggcgg cgatgttgag ttggacatac tcgcgtgcca    6240
ggcacttcca ttcggggaag atagttgtta attcatctgg cacgattctc acttgccacc    6300
ctcgattatg caaggtaatt aaatccacac tggtggccac ctcgcctcga aggggttcat    6360
tggtccaaca gagcctacct cctttcctag aacagaaagg gggaagtggg tctagcataa    6420
gttcatcggg agggtctgca tccatggtaa agattcccgg aagtaaatcc ttatcaaaat    6480
agctgatggg agtggggtca tctaaggcca tttgccattc tcgagctgcc agtgcgcgct    6540
catatgggtt aaggggactg ccccagggca tgggatgggt gagagcagag gcatacatgc    6600
cacagatgtc atagacgtag atgggatcct caaagatgcc tatgtaggtt ggatagcatc    6660
gcccccctct gatacttgct cgcacatagt catatagttc atgtgatggc gctagcagcc    6720
ccggacccaa gttggtgcga ttgggttttt ctgttctgta gacgatctgg cgaaagatgg    6780
cgtgagaatt ggaagagatg gtgggtcttt gaaaaatgtt gaaatgggca tgaggtagac    6840
ctacagagtc tctgacaaag tgggcataag attcttgaag cttggttacc agttcggcgg    6900
```

```
tgacaagtac gtctagggcg cagtagtcaa gtgtttcttg aatgatgtca taacctggtt    6960
ggttttcctt ttcccacagt tcgcggttga gaaggtattc ttcgcgatcc ttccagtact    7020
cttctagcgg aaacccgtct ttgtctgcac ggtaagatcc tagcatgtag aactgattaa    7080
ctgccttgta agggcagcag cccttctcta cgggtagaga gtatgcttga gcagcttttc    7140
gtagcgaagc gtgagtaagg gcaaaggtgt ctctgaccat gactttgaga aattggtatt    7200
tgaagtccat gtcgtcacag gctccctgtt cccagagttg gaagtctacc cgtttcttgt    7260
aggcgggggtt gggcaaagcg aaagtaacat cattgaagag aatcttaccg gctctgggca    7320
taaaattgcg agtgatgcgg aaaggctgtg gtacttccgc tcgattgttg atcacctggg    7380
cagctaggac gatttcgtcg aaaccgttga tgttgtgtcc tacgatgtat aattctatga    7440
aacgcggcgt gcctctgacg tgaggtagct tactgagctc atcaaaggtt aggtctgtgg    7500
ggtcagataa ggcgtagtgt tcgagagccc attcgtgcag gtgaggattt gcatgtagga    7560
atgatgacca aagatctacc gccagtgctg tttgtaactg gtcccgatac tgacgaaaat    7620
gccggccaat tgccattttt tctggagtga cacagtagaa ggttctgggg tcttgttgcc    7680
atcgatccca cttgagttta atggctagat cgtgggccat gttgacgaga cgctcttctc    7740
ctgagagttt catgaccagc atgaaaggaa ctagttgttt gccaaaggat cccatccagg    7800
tgtaagtttc cacatcgtag gtcaggaaga gtctttctgt gcgaggatga gagccgatcg    7860
ggaagaactg gatttcctgc caccagttgg aggattggct gttgatgtga tggaagtaga    7920
agtttctgcg gcgcgccgag cattcgtgtt tgtgcttgta cagacggccg cagtagtcgc    7980
agcgttgcac gggttgtatc tcgtgaatga gctgtacctg gcttcccttg acgagaaatt    8040
tcagtgggaa gccgaggcct ggcgattgta tctcgtgctc ttctatattc gctgtatcgg    8100
cctgttcatc ttctgtttcg atggtggtca tgctgacgag ccccgcgggg aggcaagtcc    8160
agacctcggc gcgggagggg cggagctgaa ggacgagagc gcgcaggctg gagctgtcca    8220
gagtcctgag acgctgcgga ctcaggttag taggtaggga cagaagatta acttgcatga    8280
tcttttccag ggcgtgcggg aggttcgagat ggtacttgat ttccacaggt tcgtttgtag    8340
agacgtcaat ggcttgcagg gttccgtgtc ctttgggcgc cactaccgta cctttgtttt    8400
ttcttttgat cggtggtggc tctcttgctt cttgcatgct cagaagcggt gacggggacg    8460
cgcgccgggc ggcagcggtt gttccggacc cgggggcatg gctggtagtg gcacgtcggc    8520
gccgcgcacg ggcaggttct ggtattgcgc tctgagaaga cttgcgtgcg ccaccacgcg    8580
tcgattgacg tcttgtatct gacgtctctg ggtgaaagct accggccccg tgagcttgaa    8640
cctgaaagag agttcaacag aatcaatttc ggtatcgtta acggcagctt gtctcagtat    8700
ttcttgtacg tcaccagagt tgtcctggta ggcgatctcc gccatgaact gctcgatttc    8760
ttcctcctga agatctccgc gacccgctct ttcgacggtg gccgcgaggt cattggagat    8820
acggcccatg agttgggaga atgcattcat gcccgcctcg ttccagacgc ggctgtaaac    8880
cacggccccc tcggagtctc ttgcgcgcat caccacctga gcgaggttaa gctccacgtg    8940
tctggtgaag accgcatagt tgcataggcg ctgaaaaagg tagttgagtg tggtggcaat    9000
gtgttcggcg acgaagaaat acatgatcca tcgtctcagc ggcatttcgc taacatcgcc    9060
cagagcttcc aagcgctcca tggcctcgta gaagtccacg gcaaaattaa aaaactggga    9120
gtttcgcgcg gacacggtca attcctcctc gagaagacgg atgagttcgg ctatggtggc    9180
ccgtacttcg cgttcgaagg ctcccgggat ctcttcttcc tcttctatct cttcttccac    9240
```

```
taacatctct tcttcgtctt caggcggggg cggaggggc acgcggcgac gtcgacggcg      9300
cacgggcaaa cggtcgatga atcgttcaat gacctctccg cggcggcggc gcatggtttc      9360
agtgacggcg cggccgttct cgcgcggtcg cagagtaaaa acaccgccgc gcatctcctt      9420
aaagtggtga ctgggaggtt ctccgtttgg gagggagagg gcgctgatta tacattttat      9480
taattggccc gtagggactg cgcgcagaga tctgatcgtg tcaagatcca cgggatctga      9540
aaacctttcg acgaaagcgt ctaaccagtc acagtcacaa ggtaggctga gtacggcttc      9600
ttgtgggcgg gggtggttat gtgttcggtc tgggtcttct gtttcttctt catctcggga      9660
aggtgagacg atgctgctgg tgatgaaatt aaagtaggca gttctaagac ggcggatggt      9720
ggcgaggagc accaggtctt tgggtccggc ttgctggata cgcaggcgat tggccattcc      9780
ccaagcatta tcctgacatc tagcaagatc tttgtagtag tcttgcatga gccgttctac      9840
gggcacttct tcctcacccg ttctgccatg catacgtgtg agtccaaatc cgcgcattgg      9900
ttgtaccagt gccaagtcag ctacgactct ttcggcgagg atggcttgct gtacttgggt      9960
aagggtggct tgaaagtcat caaaatccac aaagcggtgg taagcccctg tattaatggt     10020
gtaagcacag ttggccatga ctgaccagtt aactgtctgg tgaccagggc gcacgagctc     10080
ggtgtattta aggcgcgaat aggcgcgggt gtcaaagatg taatcgttgc aggtgcgcac     10140
cagatactgg tacctataa gaaaatgcgg cggtggttgg cggtagagag gccatcgttc     10200
tgtagctgga gcgccagggg cgaggtcttc aacataagg cggtgatagc cgtagatgta     10260
cctggacatc caggtgattc ctgcggcggt agtagaagcc cgaggaaact cgcgtacgcg     10320
gttccaaatg ttgcgtagcg gcatgaagta gttcattgta ggcacggttt gaccagtgag     10380
gcgcgcgcag tcattgatgc tctatagaca cggagaaaat gaaagcgttc agcgactcga     10440
ctccgtagcc tggaggaacg tgaacgggtt gggtcgcggt gtaccccggt tcgagacttg     10500
tactcgagcc ggccggagcc gcggctaacg tggtattggc actcccgtct cgacccagcc     10560
tacaaaaatc caggatacgg aatcgagtcg ttttgctggt ttccgaatgg cagggaagtg     10620
agtcctattt ttttttttt tttgccgctc agatgcatcc cgtgctgcga cagatgcgcc     10680
cccaacaaca gccccctcg cagcagcagc agcagcaacc acaaaaggct gtccctgcaa     10740
ctactgcaac tgccgccgtg agcggtgcgg gacagcccgc ctatgatctg gacttggaag     10800
agggcgaagg actggcacgt ctaggtgcgc cttcgcccga gcggcatccg cgagttcaac     10860
tgaaaaagga ttctcgcgag gcgtatgtgc cccaacagaa cctatttaga gacagaagcg     10920
gcgaggagcc ggaggagatg cgagcttccc gctttaacgc gggtcgtgag ctgcgtcacg     10980
gtttggaccg aagacgagtg ttgcgagacg aggatttcga agttgatgaa gtgacaggga     11040
tcagtcctgc caggcacac gtggctgcag ccaaccttgt atcggcttac gagcagacag     11100
taaggaaga gcgtaacttc caaaagtctt ttaataatca tgtgcgaacc ctgattgccc     11160
gcgaagaagt tacccttggt ttgatgcatt tgtgggattt gatggaagct atcattcaga     11220
accctactag caaacctctg accgcccagc tgtttctggt ggtgcaacac agcagagaca     11280
atgaggcttt cagagaggcg ctgctgaaca tcaccgaacc cgaggggaga tggttgtatg     11340
atcttatcaa cattctacag agtatcatag tgcaggagcg gagcctgggc ctggccgaga     11400
aggtagctgc catcaattac tcggttttga gcttgggaaa atattacgct cgcaaaatct     11460
acaagactcc atacgttccc atagacaagg aggtgaagat agatgggttc tacatgcgca     11520
tgacgctcaa ggtcttgacc ctgagcgatg atcttgggt gtatcgcaat gacagaatgc     11580
atcgcgcggt tagcgccagc aggaggcgcg agttaagcga cagggaactg atgcacagtt     11640
```

-continued

```
tgcaaagagc tctgactgga gctggaaccg agggtgagaa ttacttcgac atgggagctg   11700
acttgcagtg gcagcctagt cgcagggctc tgagcgccgc gacggcagga tgtgagcttc   11760
cttacataga agaggcggat gaaggcgagg aggaagaggg cgagtacttg aagagactgat  11820 ggcacaaccc gtgttttttg ctagatggaa cagcaagcac cggatcccgc aatgcgggcg   11880
gcgctgcaga gccagccgtc cggcattaac tcctcggacg attggaccca ggccatgcaa   11940
cgtatcatgg cgttgacgac tcgcaacccc gaagccttta gacagcaacc ccaggccaac   12000
cgtctatcgg ccatcatgga agctgtagtg ccttcccgat ctaatcccac tcatgagaag   12060
gtcctggcca tcgtgaacgc gttggtggag aacaaagcta ttcgtccaga tgaggccgga   12120
ctggtataca acgctctctt agaacgcgtg gctcgctaca acagtagcaa tgtgcaaacc   12180
aatttggacc gtatgataac agatgtacgc gaagccgtgt ctcagcgcga aaggttccag   12240
cgtgatgcca acctgggttc gctggtggcg ttaaatgctt tcttgagtac tcagcctgct   12300
aatgtgccgc gtggtcaaca ggattatact aacttttaa gtgctttgag actgatggta    12360
tcagaagtac ctcagagcga agtgtatcag tccggtcctg attacttctt tcagactagc   12420
agacagggct tgcagacggt aaatctgagc caagctttta aaaaccttaa aggtttgtgg   12480
ggagtgcatg ccccggtagg agaaagagca accgtgtcta gcttgttaac tccgaactcc   12540
cgcctgttat tactgttggt agctcctttc accgacagcg gtagcatcga ccgtaattcc   12600
tatttgggtt acctactaaa cctgtatcgc gaagccatag ggcaaagtca ggtggacgag   12660
cagacctatc aagaaattac ccaagtcagt cgcgctttgg gacaggaaga cactggcagt   12720
ttggaagcca ctctgaactt cttgcttacc aatcggtctc aaaagatccc tcctcaatat   12780
gctcttactg cggaggagga gaggatcctt agatatgtgc agcagagcgt gggattgttt   12840
ctgatgcaag aggggcaac tccgactgca gcactggaca tgacagcgcg aaatatggag    12900
cccagcatgt atgccagtaa ccgaccttc attaacaaac tgctggacta cttgcacaga    12960
gctgccgcta tgaactctga ttatttcacc aatgccatct taaacccgca ctggctgccc   13020
ccacctggtt tctacacggg cgaatatgac atgcccgacc ctaatgacgg atttctgtgg   13080
gacgacgtgg acagcgatgt tttttcacct ctttctgatc atcgcacgtg gaaaaaggaa   13140
ggcggtgata gaatgcattc ttctgcatcg ctgtccgggg tcatgggtgc taccgcggct   13200
gagcccgagt ctgcaagtcc ttttcctagt ctacccttt ctctacacag tgtacgtagc    13260
agcgaagtgg gtagaataag tcgcccgagt ttaatgggcg aagaggagta cctaaacgat   13320
tccttgctca gaccggcaag agaaaaaat ttcccaaaca atggaataga aagtttggtg    13380
gataaaatga gtagatggaa gacttatgct caggatcaca gagacgagcc tgggatcatg   13440
gggactacaa gtagagcgag ccgtagacgc cagcgccatg acagacagag gggtcttgtg   13500
tgggacgatg aggattcggc cgatgatagc agcgtgttgg acttgggtgg agaggaagg    13560 ggcaacccgt ttgctcattt gcgccctcgc ttgggtggta tgttgtgaaa aaaaataaaa   13620
aagaaaaact caccaaggcc atggcgacga gcgtacgttc gttcttcttt attatctgtg   13680
tctagtataa tgaggcgagt cgtgctaggc ggagcggtgg tgtatccgga gggtcctcct   13740
ccttcgtacg agagcgtgat gcagcagcag caggcgacgg cggtgatgca atccccactg   13800
gaggctccct ttgtgcctcc gcgataccgt gcacctacgg agggcagaaa cagcattcgt   13860
tactcggaac tggcacctca gtacgatacc accaggttgt atctggtgga caacaagtcg   13920
gcggacattg cttctctgaa ctatcagaat gaccacagca acttcttgac cacggtggtg   13980
```

-continued

```
cagaacaatg actttacccc tacggaagcc agcacccaga ccattaactt tgatgaacga    14040
tcgcggtggg gcggtcagct aaagaccatc atgcatacta acatgccaaa cgtgaacgag    14100
tatatgttta gtaacaagtt caaagcgcgt gtgatggtgt ccagaaaacc tcccgacggt    14160
gctgcagttg gggatactta tgatcacaag caggatattt tggaatatga gtggttcgag    14220
tttactttgc cagaaggcaa cttttcagtt actatgacta ttgatttgat gaacaatgcc    14280
atcatagata attacttgaa agtgggtaga cagaatggag tgcttgaaag tgacattggt    14340
gttaagttcg acaccaggaa cttcaagctg ggatgggatc ccgaaaccaa gttgatcatg    14400
cctggagtgt atacgtatga agccttccat cctgacattg tcttactgcc tggctgcgga    14460
gtggatttta ccgagagtcg tttgagcaac cttcttggta tcagaaaaaa acagccattt    14520
caagagggtt ttaagatttt gtatgaagat ttagaaggtg gtaatattcc ggccctcttg    14580
gatgtagatg cctatgagaa cagtaagaaa gaacaaaaag ccaaaataga agctgctaca    14640
gctgctgcag aagctaaggc aaacatagtt gccagcgact ctacaagggt tgctaacgct    14700
ggagaggtca gaggagacaa ttttgcgcca cacctgttcc cgactgcaga atcattattg    14760
gccgatgtgt ctgaaggaac ggacgtgaaa ctcactattc aacctgtaga aaagatagt    14820 aagaatagaa gctataatgt gttggaagac aaaatcaaca cagcctatcg cagttggtat    14880
cttccgtaca attatggcga tcccgaaaaa ggagtgcgtt cctggacatt gctcaccacc    14940
tcagatgtca cctgcggagc agagcaggtt tactggtcgc ttccagacat gatgaaggat    15000
cctgtcactt tccgctccac tagacaagtc agtaactacc ctgtggtggg tgcagagctt    15060
atgcccgtct tctcaaagag cttctacaac gaacaagctg tgtactccca gcagctccgc    15120
cagtccacct cgcttacgca cgtcttcaac cgctttcctg agaaccagat tttaatccgt    15180
ccgccggcgc ccaccattac caccgtcagt gaaaacgttc ctgctctcac agatcacggg    15240
accctgccgt tgcgcagcag tatccgggga gtccaacgtg tgaccgttac tgacgccaga    15300
cgccgcacct gtccctacgt gtacaaggca ctgggcatag tcgcaccgcg cgtcctttca    15360
agccgcactt tctaaaaaaa aaaaatgtcc attcttatct cgcccagtaa taacaccggt    15420
tggggtctgc gcgctccaag caagatgtac ggaggcgcac gcaaacgttc tacccaacat    15480
cccgtgcgtg ttcgcggaca ttttcgcgct ccatggggtg ccctcaaggg ccgcactcgc    15540
gttcgaacca ccgtcgatga tgtaatcgat caggtggttg ccgacgcccg taattatact    15600
cctactgcgc ctacatctac tgtggatgca gttattgaca gtgtagtggc tgacgctcgc    15660
aactatgctc gacgtaagag ccggcgaagg cgcattgcca gacgccaccg agctaccact    15720
gccatgcgag ccgcaagagc tctgctacga agagctagac gcgtggggcg aagagccatg    15780
cttagggcgg ccagacgtgc agcttcgggc gccagcgccg gcaggtcccg caggcaagca    15840
gccgctgtcg cagcggcgac tattgccgac atggcccaat cgcgaagagg caatgtatac    15900
tgggtgcgta cgctgccacc ggtcaacgt gtacccgtgc gcaccccgtcc ccctcgcact    15960 tagaagatac tgagcagtct ccgatgttgt gtcccagcgg cgaggatgtc caagcgcaaa    16020
tacaaggaag aaatgctgca ggttatcgca cctgaagtct acggccaacc gttgaaggat    16080
gaaaaaaaac cccgcaaaat caagcgggtt aaaaaggaca aaaagaaga ggaagatggc    16140 gatgatgggc tggcggagtt tgtgcgcgag tttgccccac ggcgacgcgt gcaatggcgt    16200
gggcgcaaag ttcgacatgt gttgagacct ggaacttcgg tggtctttac acccggcgag    16260
cgttcaagcg ctacttttaa gcgttcctat gatgaggtgt acgggatga tgatattctt    16320 gagcaggcgg ctgaccgatt aggcgagttt gcttatggca agcgtagtag aataacttcc    16380
```

-continued

```
aaggatgaga cagtgtcaat acccttggat catggaaatc ccaccectag tcttaaaccg   16440
gtcactttgc agcaagtgtt acccgtaact ccgcgaacag gtgttaaacg cgaaggtgaa   16500
gatttgtatc ccactatgca actgatggta cccaaacgcc agaagttgga ggacgttttg   16560
gagaaagtaa aagtggatcc agatattcaa cctgaggtta aagtgagacc cattaagcag   16620
gtagcgcctg gtctgggggt acaaactgta gacattaaga ttcccactga agtatggaa    16680
gtgcaaactg aacccgcaaa gcctactgcc acctccactg aagtgcaaac ggatccatgg   16740
atgcccatgc ctattacaac tgacgccgcc ggtcccactc aagatcccg acgaaagtac    16800
ggtccagcaa gtctgttgat gcccaattat gttgtacacc catctattat tcctactcct   16860
ggttaccgag gcactcgcta ctatcgcagc cgaaacagta cctcccgccg tcgccgcaag   16920
acacctgcaa atcgcagtcg tcgccgtaga cgcacaagca aaccgactcc cggcgccctg   16980
gtgcggcaag tgtaccgcaa tggtagtgcg gaacctttga cactgccgcg tgcgcgttac    17040
catccgagta tcatcactta atcaatgttg ccgctgcctc cttgcagata tggccctcac    17100
ttgtcgcctt cgcgttccca tcactggtta ccgaggaaga aactcgcgcc gtagaagagg   17160
gatgttggga cgcggaatgc gacgctacag gcgacggcgt gctatccgca agcaattgcg   17220
gggtggtttt ttaccagcct taattccaat tatcgctgct gcaattggcg cgataccagg   17280
catagcttcc gtggcggttc aggcctcgca acgacattga cattggaaaa aaaacgtata   17340
aataaaaaaa aatacaatgg actctgacac tcctggtcct gtgactatgt tttcttagag   17400
atggaagaca tcaattttttc atccttggct ccgcgacacg gcacgaagcc gtacatgggc    17460
acctggagcg acatcggcac gagccaactg aacgggggcg ccttcaattg gagcagtatc   17520
tggagcgggc ttaaaaattt tggctcaacc ataaaaacat acgggaacaa agcttggaac   17580
agcagtacag gacaggcgct tagaaataaa cttaaagacc agaacttcca acaaaaagta   17640
gtcgatggga tagcttccgg catcaatgga gtggtagatt tggctaacca ggctgtgcag   17700
aaaaagataa acagtcgttt ggacccgccg ccagcaaccc caggtgaaat gcaagtggag   17760
gaagaaattc ctccgccaga aaacgaggc gacaagcgtc cgcgtcccga tttggaagag    17820
acgctggtga cgcgcgtaga tgaaccgcct tcttatgagg aagcaacgaa gcttggaatg   17880
cccaccacta gaccgatagc cccaatggcc accggggtga tgaaaccttc tcagttgcat   17940
cgacccgtca ccttggattt gccccctccc cctgctgcta ctgctgtacc cgcttctaag   18000
cctgtcgctg ccccgaaacc agtcgccgta gccaggtcac gtcccggggg cgctcctcgt   18060
ccaaatgcgc actggcaaaa tactctgaac agcatcgtgg gtctaggcgt gcaaagtgta   18120
aaacgccgtc gctgcttta attaaatatg gagtagcgct taacttgcct atctgtgtat    18180
atgtgtcatt acacgccgtc acagcagcag aggaaaaaag gaagaggtcg tgcgtcgacg   18240
ctgagttact ttcaagatgg ccaccccatc gatgctgccc caatgggcat acatgcacat   18300
cgccggacag gatgcttcgg agtacctgag tccgggtctg gtgcagttcg cccgcgccac   18360
agacacctac ttcaatctgg gaaataagtt tagaaatccc accgtagcgc cgacccacga   18420
tgtgaccacc gaccgtagcc agcggctcat gttgcgcttc gtgcccgttg accgggagga   18480
caatacatac tcttacaaag tgcggtacac cctggccgtg gcgacaaca gagtgctgga   18540
tatggccagc acgttctttg acattagggg cgtgttggac agaggtccca gtttcaaacc   18600
ctattctggt acggcttaca actctctggc tcctaaaggc gctccaaatg catctcaatg   18660
gattgcaaaa ggcgtaccaa ctgcagcagc cgcaggcaat ggtgaagaag aacatgaaac   18720
```

-continued

```
agaggagaaa actgctactt acactttgc caatgctcct gtaaaagccg aggctcaaat    18780
tacaaaagag ggcttaccaa taggtttgga gatttcagct gaaaacgaat ctaaacccat    18840
ctatgcagat aaactttatc agccagaacc tcaagtggga gatgaaactt ggactgacct    18900
agacggaaaa accgaagagt atggaggcag ggctctaaag cctactacta acatgaaacc    18960
ctgttacggg tcctatgcga agcctactaa tttaaaaggt ggtcaggcaa aaccgaaaaa    19020
ctcggaaccg tcgagtgaaa aaattgaata tgatattgac atggaatttt ttgataactc    19080
atcgcaaaga acaaacttca gtcctaaaat tgtcatgtat gcagaaaatg taggtttgga    19140
aacgccagac actcatgtag tgtacaaacc tggaacagaa gacacaagtt ccgaagctaa    19200
tttgggacaa cagtctatgc ccaacagacc caactacatt ggcttcagag ataactttat    19260
tggactcatg tactataaca gtactggtaa catgggggtg ctggctggtc aagcgtctca    19320
gttaaatgca gtggttgact tgcaggacag aaacacagaa cttttcttacc aactcttgct    19380 tgactctctg ggcgacagaa ccagatactt agcatgtgg aatcaggctg tggacagtta    19440
tgatcctgat gtacgtgtta ttgaaaatca tggtgtggaa gatgaacttc ccaactattg    19500
ttttccactg gacggcatag gtgttccaac aaccagttac aaatcaatag ttccaaatgg    19560
agaagataat aataattgga agaacctga agtaaatgga acaagtgaga tcggacaggg    19620
taatttgttt gccatggaaa ttaaccttca agccaatcta tggcgaagtt tcctttattc    19680
caatgtggct ctgtatctcc cagactcgta caaatacacc ccgtccaatg tcactcttcc    19740
agaaaacaaa aacacctacg actacatgaa cgggcgggtg gtgccgccat ctctagtaga    19800
cacctatgtg aacattggtg ccaggtggtc tctggatgcc atggacaatg tcaacccatt    19860
caaccaccac cgtaacgctg gcttgcgtta ccgatctatg cttctgggta acggacgtta    19920
tgtgcctttc cacatacaag tgcctcaaaa attcttcgct gttaaaaacc tgctgcttct    19980
cccaggctcc tacacttatg agtggaactt taggaaggat gtgaacatgg ttctacagag    20040
ttccctcggt aacgacctgc gggtagatgg cgccagcatc agtttcacga gcatcaacct    20100
ctatgctact ttttttcccca tggctcacaa caccgcttcc acccttgaag ccatgctgcg    20160
gaatgacacc aatgatcagt cattcaacga ctacctatct gcagctaaca tgctctaccc    20220
cattcctgcc aatgcaacca atattccat ttccattcct tctcgcaact gggcggcttt    20280
cagaggctgg tcatttacca gactgaaaac caaagaaact ccctcttgg ggtctggatt    20340 tgacccctac tttgtctatt ctggttctat tccctacctg gatggtaccct tctacctgaa    20400 ccacactttt aagaaggttt ccatcatgtt tgactcttca gtgagctggc ctggaaatga    20460
caggttacta tctcctaacg aatttgaaat aaagcgcact gtggatggcg aaggctacaa    20520
cgtagcccaa tgcaacatga ccaaagactg gttcttggta cagatgctcg ccaactacaa    20580
catcggctat cagggcttct acattccaga aggatacaaa gatcgcatgt attcattttt    20640
cagaaacttc cagcccatga gcaggcaggt ggttgatgag gtcaattaca aagacttcaa    20700
ggccgtcgcc ataccctacc aacacaacaa ctctggcttt gtgggttaca tggctccgac    20760
catgcgccaa ggtcaaccct atcccgctaa ctatccctat ccactcattg aacaactgc    20820 cgtaaatagt gttacgcaga aaagttctt gtgtgacaga accatgtggc gcataccgtt    20880
ctcgagcaac ttcatgtcta tgggggccct tacagacttg ggacagaata tgctctatgc    20940
caactcagct catgctctgg acatgacctt tgaggtggat cccatggatg agcccaccct    21000
gctttatctc ctcttcgaag ttttcgacgt ggtcagagtg catcagccac accgcggcat    21060
catcgaggca gtctacctgc gtacaccgtt ctcggccggt aacgctacca cgtaagaagc    21120
```

```
ttcttgcttc ttgcaaatag cagctgcaac catggcctgc ggatcccaaa acggctccag    21180
cgagcaagag ctcagagcca ttgtccaaga cctgggttgc ggaccctatt ttttgggaac    21240
ctacgataag cgcttcccgg ggttcatggc ccccgataag ctcgcctgtg ccattgtaaa    21300
tacggccgga cgtgagacgg ggggagagca ctggttggct ttcggttgga acccacgttc    21360
taacacctgc taccttttg atccttttgg attctcggat gatcgtctca aacagattta    21420
ccagtttgaa tatgagggtc tcctgcgccg cagcgctctt gctaccaagg accgctgtat    21480
tacgctggaa aaatctaccc agaccgtgca gggcccccgt tctgccgcct gcggactttt    21540
ctgctgcatg ttccttcacg cctttgtgca ctggcctgac cgtcccatgg acggaaaccc    21600
caccatgaaa ttgctaactg gagtgccaaa caacatgctt cattctccta agtccagcc    21660 caccctgtgt gacaatcaaa aagcactcta ccattttctt aatacccatt cgccttattt    21720
tcgctctcat cgtacacaca tcgaaagggc cactgcgttc gaccgtatgg atgttcaata    21780
atgactcatg taaacaacgt gttcaataaa catcacttta ttttttaca tgtatcaagg    21840 ctctggatta cttatttatt tacaagtcga atgggttctg acgagaatca gaatgacccg    21900
caggcagtga tacgttgcgg aactgatact tgggttgcca cttgaattcg ggaatcacca    21960
acttgggaac cggtatatcg ggcaggatgt cactccacag ctttctggtc agctgcaaag    22020
ctccaagcag gtcaggagcc gaaatcttga atcacaatt aggaccagtg ctctgagcgc    22080
gagagttgcg gtacaccgga ttgcagcact gaaacaccat cagcgacgga tgtctcacgc    22140
ttgccagcac ggtgggatct gcaatcatgc ccacatccag atcttcagca ttggcaatgc    22200
tgaacggggt catcttgcag gtctgcctac ccatggcggg cacccaatta ggcttgtggt    22260
tgcaatcgca gtgcagggg atcagtatca tcttggcctg atcctgtctg attcctggat    22320
acacggctct catgaaagca tcatattgct tgaaagcctg ctgggcttta ctaccctcgg    22380
tataaaacat cccgcaggac ctgctcgaaa actggttagc tgcacagccg gcatcattca    22440
cacagcagcg ggcgtcattg ttggctattt gcaccacact tctgccccag cggttttggg    22500
tgattttggt tcgctcggga ttctccttta aggctcgttg tccgttctcg ctggccacat    22560
ccatctcgat aatctgctcc ttctgaatca taatattgcc atgcaggcac ttcagcttgc    22620
cctcataatc attgcagcca tgaggccaca acgcacagcc tgtacattcc caattatggt    22680
gggcgatctg agaaaaagaa tgtatcattc cctgcagaaa tcttcccatc atcgtgctca    22740
gtgtcttgtg actagtgaaa gttaactgga tgcctcggtg ctcttcgttt acgtactggt    22800
gacagatgcg cttgtattgt tcgtgttgct caggcattag tttaaaacag gttctaagtt    22860
cgttatccag cctgtacttc tccatcagca gacacatcac ttccatgcct ttctcccaag    22920
cagacaccag gggcaagcta atcggattct taacagtgca ggcagcagct cctttagcca    22980
gagggtcatc tttagcgatc ttctcaatgc ttcttttgcc atccttctca acgatgcgca    23040
cgggcgggta gctgaaaccc actgctacaa gttgcgcctc ttctctttct tcttcgctgt    23100
cttgactgat gtcttgcatg gggatatgtt tggtcttcct tggcttcttt ttgggggta    23160 tcggaggagg aggactgtcg ctccgttccg gagacaggga ggattgtgac gtttcgctca    23220
ccattaccaa ctgactgtcg gtagaagaac ctgaccccac acggcgacag gtgttttct    23280 tcggggcag aggtggaggc gattgcgaag ggctgcggtc cgacctggaa ggcggatgac    23340
tggcagaacc cctccgcgt tcgggggtgt gctccctgtg gcggtcgctt aactgatttc    23400
cttcgcggct ggccattgtg ttctcctagg cagagaaaca acagacatgg aaactcagcc    23460
```

```
attgctgtca acatcgccac gagtgccatc acatctcgtc ctcagcgacg aggaaaagga   23520
gcagagctta agcattccac cgcccagtcc tgccaccacc tctaccctag aagataagga   23580
ggtcgacgca tctcatgaca tgcagaataa aaaagcgaaa gagtctgaga cagacatcga   23640
gcaagacccg ggctatgtga caccggtgga acacgaggaa gagttgaaac gctttctaga   23700
gagagaggat gaaaactgcc caaaacagcg agcagataac tatcaccaag atgctggaaa   23760
tagggatcag aacaccgact acctcatagg gcttgacggg gaagacgcgc tccttaaaca   23820
tctagcaaga cagtcgctca tagtcaagga tgcattattg gacagaactg aagtgcccat   23880
cagtgtggaa gagctcagct gcgcctacga gcttaacctt ttttcacctc gtactccccc   23940
caaacgtcag ccaaacggca cctgcgagcc aaatcctcgc ttaaacttttt atccagcttt   24000 tgctgtgcca gaagtactgg ctacctatca catcttttttt aaaaatcaaa aaattccagt   24060
ctcctgccgc gctaatcgca cccgcgccga tgccctactc aatctgggac ctggttcacg   24120
cttacctgat atagcttcct tggaagaggt tccaaagatc ttcgagggtc tgggcaataa   24180
tgagactcgg gccgcaaatg ctctgcaaaa gggagaaaat ggcatggatg agcatcacag   24240
cgttctggtg gaattggaag gcgataatgc cagactcgca gtactcaagc gaagcgtcga   24300
ggtcacacac ttcgcatatc ccgctgtcaa cctgcccccct aaagtcatga cggcggtcat   24360
ggaccagtta ctcattaagc gcgcaagtcc cctttcagaa gacatgcatg acccagatgc   24420
ctgtgatgag ggtaaaccag tggtcagtga tgagcagcta acccgatggc tgggcaccga   24480
ctctccccgg gatttggaag agcgtcgcaa gcttatgatg gccgtggtgc tggttaccgt   24540
agaactagag tgtctccgac gtttctttac cgattcagaa accttgcgca aactcgaaga   24600
gaatctgcac tacactttta gacacggctt tgtgcggcag gcatgcaaga tatctaacgt   24660
ggaactcacc aacctggttt cctacatggg tattctgcat gagaatcgcc taggacaaag   24720
cgtgctgcac agcaccctta aggggaagc ccgccgtgat tacatccgcg attgtgtcta   24780
tctctacctg tgccacacgt ggcaaaccgg catgggtgta tggcagcaat gtttagaaga   24840
acagaacttg aaagagcttg acaagctctt acagaaatct cttaaggttc tgtggacagg   24900
gttcgacgag cgcaccgtcg cttccgacct ggcagacctc atcttcccag agcgtctcag   24960
ggttactttg cgaaacggat tgcctgactt tatgagccag agcatgctta acaattttcg   25020
ctctttcatc ctggaacgct ccggtatcct gcccgccacc tgctgcgcac tgccctccga   25080 cttttgtgcct ctcacctacc gcgagtgccc ccgccgcta tggagtcact gctacctgtt   25140
ccgtctggcc aactatctct cctaccactc ggatgtgatc gaggatgtga gcggagacgg   25200
cttgctggag tgccactgcc gctgcaatct gtgcacgccc caccggtccc tagcttgcaa   25260
cccccagttg atgagcgaaa cccagataat aggcacccttt gaattgcaag gccccagcag   25320
ccaaggcgat gggtcttctc ctgggcaaag tttaaaactg accccgggac tgtggacctc   25380
cgcctacttg cgcaagtttg ctccggaaga ttaccacccc tatgaaatca gttctatga   25440 ggaccaatca cagcctccaa aggccgaact ttcggcttgc gtcatcaccc agggggcaat   25500 tctgcccaa ttgcaagcca tccaaaaatc ccgccaagaa tttctactga aaagggtaa   25560 gggggtctac cttgaccccc agaccggcga ggaactcaac acaaggttcc ctcaggatgt   25620
cccaacgacg agaaaacaag aagttgaagg tgcagccgcc gccccagaa gatatgagg   25680 aagattggga cagtcaggca gaggagcgg aggaggacag tctggaggac agtctggagg   25740
aagacagttt ggaggaggaa aacgaggagg cagaggaggt ggaagaagta accgccgaca   25800
aacagttatc ctcggctgcg gagacaagca acagcgctac catctccgct ccgagtcgag   25860
```

```
gaacccggcg gcgtcccagc agtagatggg acgagaccgg acgcttcccg aacccaacca   25920
gcgcttccaa gaccggtaag aaggatcggc agggatacaa gtcctggcgg gggcataaga   25980
atgccatcat ctcctgcttg catgagtgcg ggggcaacat atccttcacg cggcgctact   26040
tgctattcca ccatggggtg aactttccgc gcaatgtttt gcattactac cgtcacctcc   26100
acagccccta ctatagccag caaatcccga cagtctcgac agataaagac agcggcggcg   26160
acctccaaca gaaaccagc agcggcagtt agaaaataca caacaagtgc agcaacagga    26220
ggattaaaga ttacagccaa cgagccacgcg caaacccgag agttaagaaa tcggatcttt   26280
ccaaccctgt atgccatctt ccagcagagt cggggtcaag agcaggaact gaaaataaaa   26340
aaccgatctc tgcgttcgct caccagaagt tgtttgtatc acaagagcga agatcaactt   26400
cagcgcactc tcgaggacgc cgaggctctc ttcaacaagt actgcgcgct gactcttaaa   26460
gagtaggcag cgaccgcgct tattcaaaaa aggcgggaat tacatcatcc tcgacatgag   26520
taaagaaatt cccacgcctt acatgtggag ttatcaaccc caaatgggat tggcagcagg   26580
cgcctcccag gactactcca cccgcatgaa ttggctcagc gccgggcctt ctatgatttc   26640
tcgagttaat gatatacgcg cctaccgaaa ccaaatactt ttggaacagt cagctcttac   26700
caccacgccc cgccaacacc ttaatcccag aaattggccc gccgcctag tgtaccagga    26760 aagtcccgct cccaccactg tattacttcc tcgagacgcc caggccgaag tccaaatgac   26820
taatgcaggt gcgcagttag ctggcggctc caccctatgt cgtcacaggc ctcggcataa   26880
tataaaacgc ctgatgatca gaggccgagg tatccagctc aacgacgagt cggtgagctc   26940
tccgcttggt ctacgaccag acggaatctt tcagattgcc ggctgcggga gatcttcctt   27000
cacccctcgt caggctgttc tgactttgga agttcgtct tcgcaacccc gctcgggcgg    27060
aatcgggacc gttcaatttg tagaggagtt tactccctct gtctacttca accccttctc   27120
cggatctcct gggcactacc cggacgagtt cataccgaac ttcgacgcga ttagcgagtc   27180
agtggacggc tacgattgat gtctggtgac gcggctgagc tatctcggct gcgacatcta   27240
gaccactgcc gccgctttcg ctgctttgcc cgggaactta ttgagttcat ctacttcgaa   27300
ctccccaagg atcaccctca aggtccggcc cacggagtgc ggattactat cgaaggcaaa   27360
atagactctc gcctgcaacg aattttctcc cagcggcccg tgctgatcga gcgagaccag   27420
ggaaacacca cggtttccat ctactgcatt tgtaatcacc ccggattgca tgaaagcctt   27480
tgctgtctta tgtgtactga gtttaataaa aactgaatta agactctcct acggactgcc   27540
gcttcttcaa cccggatttt acaaccagaa gaacaaaact tttcctgtcg tccaggactc   27600
tgttaacttc acctttccta ctcacaaact agaagctcaa cgactacacc gcttttccag   27660
aagcattttc cctactaata ctactttcaa aaccggaggt gagctccacg gtctccctac   27720
agaaaaccct tgggtggaag cgggcccttgt agtactagga attcttgcgg gtgggcttgt   27780
gattattctt tgctacctat acacaccttg cttcactttc ctagtggtgt tgtggtattg   27840
gtttaaaaaa tggggcccat actagtcttg cttgttttac tttcgctttt ggaaccgggt   27900
tctgccaatt acgatccatg tctagacttt gacccagaaa actgcacact tacttttgca   27960
cccgacacaa gccgcatctg tggagttctt attaagtgcg gatgggaatg caggtccgtt   28020
gaaattacac acaataacaa aacctggaac aataccttat ccaccacatg ggagccagga   28080
gttcccgagt ggtacactgt ctctgtccga ggtcctgacg gttccatccg cattagtaac   28140
aacactttca ttttttctga aatgtgcgat ctggccatgt tcatgagcaa acagtattct   28200
```

```
ctatggcctc ctagcaagga caacatcgta acgttctcca ttgcttattg cttgtgcgct   28260
tgccttctta ctgctttact gtgcgtatgc atacacctgc ttgtaaccac tcgcatcaaa   28320
aacgccaata acaaagaaaa aatgccttaa cctctttctg tttacagaca tggcttctct   28380
tacatctctc atatttgtca gcattgtcac tgccgctcac ggacaaacag tcgtctctat   28440
cccactagga cataattaca ctctcatagg accccaatc acttcagagg tcatctggac    28500
caaactggga agcgttgatt actttgatat aatctgtaac aaaacaaaac caataatagt   28560
aacttgcaac atacaaaatc ttacattgat taatgttagc aaagtttaca gcggttacta   28620
ttatggttat gacagataca gtagtcaata tagaaattac ttggttcgtg ttacccagtt   28680
gaaaaccacg aaaatgccaa atatggcaaa gattcgatcc gatgacaatt ctctagaaac   28740
ttttacatct cccaccacac ccgacgaaaa aaacatccca gattcaatga ttgcaattgt   28800
tgcagcggtg gcagtggtga tggcactaat aataatatgc atgcttttat atgcttgtcg   28860
ctacaaaaag tttcatccta aaaacaaga tctcctacta aggcttaaca tttaatttct    28920 tttatacag ccatggtttc cactaccaca ttccttatgc ttactagtct cgcaactctg     28980
acttctgctc gctcacacct cactgtaact ataggctcaa actgcacact aaaaggacct   29040
caaggtggtc atgtcttttg gtggagaata tatgacaatg gatggtttac aaaaccatgt   29100
gaccaacctg gtagattttt ctgcaacggc agagacctaa ccattatcaa cgtgacagca   29160
aatgacaaag gcttctatta tggaaccgac tataaaagta gtttagatta taacattatt   29220
gtactgccat ctaccactcc agcacccccgc acaactactt tctctagcag cagtgtcgct   29280
aacaatacaa tttccaatcc aaccttccc gcgctttaa aacgcactgt gaataattct    29340
acaacttcac atacaacaat ttccacttca acaatcagca tcatcgctgc agtgacaatt   29400
ggaatatcta ttcttgtttt taccataacc tactacgcct gctgctatag aaaagacaaa   29460
cataaaggtg atccattact tagatttgat attaatttg ttctttttt ttatttacag     29520 tatggtgaac accaatcatg gtacctagaa atttcttctt caccatactc atctgtgctt   29580
ttaatgtttg cgctactttc acagcagtag ccacagcaac cccagactgt ataggagcat   29640
ttgcttccta tgcactttt gcttttgtta cttgcatctg cgtatgtagc atagtctgcc    29700
tggttattaa ttttttccaa cttctagact ggatccttgt gcgaattgcc tacctgcgcc   29760
accatcccga ataccgcaac caaaatatcg cggcactttc tagactcatc taaaaccatg   29820
caggctatac taccaatatt tttgcttcta ttgcttccct acgctgtctc aacccccagct 29880 gcctatagta ctccaccaga acaccttaga aaatgcaaat tccaacaacc gtggtcattt   29940
cttgcttgct atcgagaaaa atcagaaatc cccccaaatt taataatgat tgctggaata   30000
attaatataa tctgttgcac cataatttca ttttgatat accccctatt tgattttggc    30060
tggaatgctc ccaatgcaca tgatcatcca caagacccag aggaacacat tcccccacaa   30120
aacatgcaac atccaatagc gctaatagat tacgaaagtg aaccacaacc cccactctc    30180 cctgctatta gttacttcaa cctaaccggc ggagatgact gaaacactca ccacctccaa   30240
ttccgccgag gatctgctcg atatggacgg ccgcgtctca gaacaacgac ttgcccaact   30300
acgcatccgc cagcagcagg aacgcgtggc caaagagctc agagatgtca tccaaattca   30360
ccaatgcaaa aaaggcatat tctgtttggt aaaacaagcc aagatatcct acgagatcac   30420
cgctactgac catcgcctct cttacgaact tggccccaa cgacaaaat ttacctgcat     30480 ggtgggaatc aaccccatag ttatcaccca acaaagtgga gatactaagg gttgcattca   30540
ctgctcctgc gattccatcg agtgcaccta caccctgctg aagaccctat gcggcctaag   30600
```

```
agacctgcta ccaatgaatt aaaaaaaaat gattaataaa aaatcactta cttgaaatca    30660
gcaataaggt ctctgttgaa attttctccc agcagcacct cacttccctc ttcccaactc    30720
tggtattcta aaccccgttc agcggcatac tttctccata cttaaagggg atgtcaaat    30780 tttagctcct ctcctgtacc cacaatcttc atgtctttct tcccagatga ccaagagagt    30840
ccggctcagt gactccttca accctgtcta cccctatgaa gatgaaagca cctcccaaca    30900 ccccttata aacccagggt ttatttcccc aaatggcttc acacaaagcc cagacggagt    30960
tcttacttta aaatgtttaa ccccactaac aaccacaggc ggatctctac agctaaaagt    31020
gggaggggga cttacagtgg atgacactga tggtaccttga caagaaaaca tacgtgctac    31080
agcacccatt actaaaaata atcactctgt agaactatcc attggaaatg gattagaaac    31140
tcaaaacaat aaactatgtg ccaaattggg aaatggggtta aaatttaaca acggtgacat    31200
ttgtataaag gatagtatta acaccttatg gactggaata aaccctccac ctaactgtca    31260
aattgtggaa aacactaata caaatgatgg caaacttact ttagtattag taaaaaatgg    31320
agggcttgtt aatggctacg tgtctctagt tggtgtatca gacactgtga accaaatgtt    31380
cacacaaaag acagcaaaca tccaattaag attatatttt gactcttctg gaaatctatt    31440
aactgaggaa tcagacttaa aaattccact taaaaataaa tcttctacag cgaccagtga    31500
aactgtagcc agcagcaaag cctttatgcc aagtactaca gcttatccct tcaacaccac    31560
tactagggat agtgaaaact acattcatgg aaatatgttac tacatgacta gttatgatag    31620
aagtctattt cccttgaaca tttctataat gctaaacagc cgtatgattt cttccaatgt    31680
tgcctatgcc atacaatttg aatggaatct aaatgcaagt gaatctccag aaagcaacat    31740
agctacgctg accacatccc ccttttttctt ttcttacatt acagaagacg acaactaaaa    31800
taaagtttaa gtgtttttat ttaaaatcac aaaattcgag tagttattt gcctccacct    31860 tcccatttga cagaatacac caatctctcc ccacgcacag ctttaaacat ttggatacca    31920
ttagagatag acattgtttt agattccaca ttccaaacag tttcagagcg agccaatctg    31980
gggtcagtga tagataaaaa tccatcgcga tagtcttta aagcgctttc acagtccaac    32040
tgctgcggat gcgactccgg agtttggatc acggtcatct ggaagaagaa cgatgggaat    32100
cataatccga aaacggtatc ggacgattgt gtctcatcaa acccacaagc agccgctgtc    32160
tgcgtcgctc cgtgcgactg ctgtttatgg gatcagggtc cacagttcc tgaagcatga    32220 ttttaatagc ccttaacatc aactttctgg tgcgatgcgc gcagcaacgc attctgattt    32280
cactcaaatc tttgcagtag gtacaacaca ttattacaat attgtttaat aaaccataat    32340
taaaagcgct ccagccaaaa ctcatatctg atataatcgc ccctgcatga ccatcatacc    32400
aaagtttaat ataattaaa tgacgttccc tcaaaaacac actacccaca tacatgatct    32460
cttttggcat gtgcatatta acaatctgtc tgtaccatgg acaacgttgg ttaatcatgc    32520
aacccaatat aaccttccgg aaccacactg ccaacaccgc tcccccagcc atgcattgaa    32580
gtgaaccctg ctgattacaa tgacaatgaa gaacccaatt ctctcgaccg tgaatcactt    32640
gagaatgaaa aatatctata gtggcacaac atagacataa atgcatgcat cttctcataa    32700
tttttaactc ctcaggattt agaaacatat cccagggaat aggaagctct tgcagaacag    32760
taaagctggc agaacaagga agaccacgaa cacaacttac actatgcata gtcatagtat    32820
cacaatctgg caacgcgggg tggtcttcag tcatagaagc tcgggtttca ttttcctcac    32880
aacgtggtaa ctgggctctg gtgtaagggt gatgtctggc gcatgatgtc gagcgtgcgc    32940
```

```
gcaaccttgt cataatggag ttgcttcctg acattctcgt attttgtata gcaaaacgcg    33000
gccctggcag aacacactct tcttcgcctt ctatcctgcc gcttagcgtg ttccgtgtga    33060
tagttcaagt acagccacac tcttaagttg gtcaaaagaa tgctggcttc agttgtaatc    33120
aaaactccat cgcatctaat tgttctgagg aaatcatcca cggtagcata tgcaaatccc    33180
aaccaagcaa tgcaactgga ttgcgtttca agcaggagag gagagggaag agacggaaga    33240
accatgttaa ttttttattcc aaacgatctc gcagtacttc aaattgtaga tcgcgcagat    33300
ggcatctctc gcccccactg tgttggtgaa aaagcacagc taaatcaaaa gaaatgcgat    33360
tttcaaggtg ctcaacggtg gcttccaaca aagcctccac gcgcacatcc aagaacaaaa    33420
gaataccaaa agaaggagca ttttctaact cctcaatcat catattacat tcctgcacca    33480
ttcccagata atttttcagct ttccagcctt gaattattcg tgtcagttct tgtggtaaat    33540
ccaatccaca cattacaaac aggtcccgga gggcgccctc caccaccatt cttaaacaca    33600
ccctcataat gacaaaatat cttgctcctg tgtcacctgt agcgaattga gaatggcaac    33660
atcaattgac atgcccttgg ctctaagttc ttctttaagt tctagttgta aaaactctct    33720
catattatca ccaaactgct tagccagaag ccccccggga acaagagcag gggacgctac    33780
agtgcagtac aagcgcagac ctccccaatt ggctccagca aaaacaagat tggaataagc    33840
atattgggaa ccaccagtaa tatcatcgaa gttgctggaa atataatcag gcagagtttc    33900
ttgtagaaat tgaataaaag aaaaatttgc caaaaaaaca ttcaaaacct ctgggatgca    33960
aatgcaatag gttaccgcgc tgcgctccaa cattgttagt tttgaattag tctgcaaaaa    34020
taaaaaaaaa acaagcgtca tatcatagta gcctgacgaa caggtggata aatcagtctt    34080
tccatcacaa gacaagccac agggtctcca gctcgaccct cgtaaaaacct gtcatcgtga    34140
ttaaacaaca gcaccgaaag ttcctcgcgg tgaccagcat gaataagtct tgatgaagca    34200
tacaatccag acatgttagc atcagttaag gagaaaaaac agccaacata gcctttgggt    34260
ataattatgc ttaatcgtaa gtatagcaaa gccacccctc gcggatacaa agtaaaaggc    34320
acaggagaat aaaaaatata attatttctc tgctgctgtt taggcaacgt cgccccggt    34380
ccctctaaat acacatacaa agcctcatca gccatggctt accagagaaa gtacagcggg    34440
cacacaaacc acaagctcta aagtcactct ccaacctstc cacaatatat atacacaagc    34500
cctaaactga cgtaatggga ctaaagtgta aaaaatcccg ccaaacccaa cacacacccc    34560
gaaactgcgt caccagggaa aagtacagtt tcacttccgc aatcccaaca agcgtcactt    34620
cctctttctc acggtacgtc acatcccatt aacttacaac gtcattttcc cacggccgcg    34680
ccgccccttt taaccgttaa ccccacagcc aatcaccaca cggcccacac tttttaaaat    34740
cacctcattt acatattggc accattccat ctataaggta tattattgat gatg          34794
```